United States Patent [19]

Lahm

[11] Patent Number: 4,960,784

[45] Date of Patent: Oct. 2, 1990

[54] INSECTICIDAL SUBSTITUTED INDAZOLES

[75] Inventor: George P. Lahm, Wilmington, Del.

[73] Assignee: E. I. Du Pont de Nemours and Company, Wilmington, Del.

[21] Appl. No.: 435,511

[22] PCT Filed: Apr. 5, 1988

[86] PCT No.: PCT/US88/01004

§ 371 Date: Oct. 2, 1989

§ 102(e) Date: Oct. 2, 1989

[87] PCT Pub. No.: WO88/07994

PCT Pub. Date: Oct. 20, 1988

Related U.S. Application Data

[63] Continuation of Ser. No. 159,763, Mar. 8, 1988, abandoned, which is a continuation-in-part of Ser. No. 36,480, Apr. 19, 1987, abandoned.

[51] Int. Cl.$^5$ .................... A01N 43/56; A01N 43/90; C07D 231/54; C07D 471/04

[52] U.S. Cl. .................... 514/403; 514/211; 514/215; 514/222.2; 514/232.8; 514/287; 514/293; 514/316; 514/322; 540/488; 540/521; 540/548; 540/578; 544/63; 544/80; 544/125; 544/130; 544/140; 546/64; 546/65; 546/82; 546/187; 546/199; 548/369; 548/370

[58] Field of Search .............. 540/488, 521, 548, 578; 544/80, 125, 63, 130, 140; 546/64, 65, 82, 187, 199; 548/369, 370; 514/211, 215, 222.2, 232.5, 232.8, 287, 293, 316, 322, 403

[56] References Cited

U.S. PATENT DOCUMENTS 4,070,365 1/1978 Daalen et al. .................. 548/379
4,663,341 5/1987 Jacobson .......................... 514/403

OTHER PUBLICATIONS

Lorand et al., *J. Chem. Soc. Perkin Trans. I* (1985), pp. 481–486.

Primary Examiner—Robert W. Ramsuer
Attorney, Agent, or Firm—James A. Costello

[57] ABSTRACT

Certain substituted indazoles, including all geometric and stereoisomers thereof, agricultural compositions containing the indazoles and use of the indazoles as insecticides.

13 Claims, No Drawings

INSECTICIDAL SUBSTITUTED INDAZOLES

CROSS-REFERENCE TO RELATED APPLICATION

This application is a continuation of U.S. Ser. No. 159,763 filed on Mar. 8, 1988, now abandoned, which in turn is a continuation-in-part of U.S. Ser. No. 036.480, filed on Apr. 9, 1987, now abandoned.

BACKGROUND OF THE INVENTION

1. Field of the Invention

This invention pertains to substituted agricultural compositions containing them and a method for using the indazoles to control insects.

2. State of the Art

U.S. Pat. No. 4,070,365 discloses insecticidal compounds of the formula

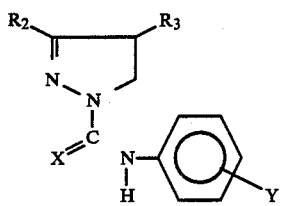

wherein
$R_2$ and $R_3$ are independently alkyl, cycloalkyl, pyridyl or thienyl optionally substituted with halogen, alkyl or nitro, or a phenyl group optionally substituted with 1 or 2 substituents selected from halogen, alkyl, haloalkyl, cycloalkyl, alkylthio, alkoxy, mono or dialkylamino, nitro, phenyl optionally substituted with halogen, or cyano;
Y is halogen, $NO_2$, alkyl, haloalkyl, cycloalkyl, alkylthio, alkoxy, dialkylamino alkylsulfonyl, acyl, acylamino, cyano, or a phenyl optionally substituted with halogen; and
X is O or S.

U.S. Pat. No. 4,663,341 discloses insecticidal compounds of the formula

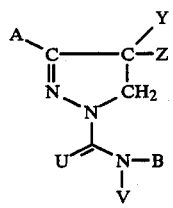

wherein
A is unsubstituted or substituted phenyl;
B is unsubstituted or substituted phenyl;
U is O, S or NR;
Y is alkyl, carbonyl or phenyl each of which may be optionally substituted; and
Z is an organic radical other than hydrogen.

SUMMARY OF THE INVENTION

This invention pertains to compounds of Formula I, including all geometric and stereoisomers, agriculturally suitable salts thereof, agricultural compositions containing them and their use as insecticides:

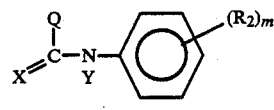

wherein

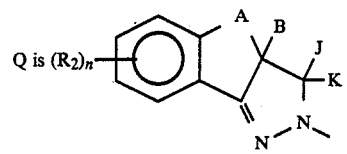

A is a 1. 2 or 3-atom bridge having 0 to 3 carbon atoms and 0 to 1 oxygen atom, $NR_6$ group, or $S(O)_q$ group, wherein each carbon individually can be substituted with 1 to 2 substituents selected from 1 to 2 halogen, $C_1$ to $C_6$ alkyl $C_2$ to $C_4$ alkoxycarbonyl or phenyl optionally substituted with 1 to 3 substituents selected from W and one of the carbon atoms can be C(O) or C(S);
B is H, $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $OR_7$, $C_2$ to $C_6$ alkoxyalkyl, $C_2$ to $C_6$ cyanoalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl, phenyl substituted by $(R_5)_p$, benzyl, or benzyl substituted with 1 to 3 substituents indePendently selected from W;
J is H, $C_1$ to $C_4$ alkyl or phenyl optionally substituted with W;
K is H or $CH_3$;
W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;
$R_1$, $R_2$ and $R_5$ are independently $R_3$, halogen, CN, $N_3$, SCN, $NO_2$, $OR_3$, $SR_3$, $SOR_3$, $SO_2R_3$, $OC(O)R_3$, $OSO_2R_3$, $CO_2R_3$, $C(O)R_3$, $C(O)NR_3R_4$, $SO_2NR_3R_4$, $NR_3R_4$, $NR_4C(O)R_3$, $OC(O)NHR_3$, $NR_4C(O)NHR_3$, $NR_4SO_2R_3$, or when m, n or p is 2, $R_1$, $R_2$ or $R_5$ can be taken together to form a 5 or 6 membered fused ring as $-OCH_2O-$, $-OCH_2CH_2O-$, or $-CH_2CH_2O-$, each of which can be substituted with 1 to 4 halogen atoms or 1 to 2 methyl groups;
$R_3$ is H, $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $C_2$ to $C_6$ haloalkynyl, $C_2$ to $C_6$ alkoxyalkyl, $C_2$ to $C_6$ alkylthioalkyl, $C_1$ to $C_6$ nitroalkyl, $C_2$ to $C_6$ cyanoalkyl, $C_3$ to $C_8$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;
$R_4$ is H, $C_1$ to $C_4$ alkyl or $R_3$ and $R_4$ can be taken together as $(CH_2)_4$, $(CH_2)_5$ or $(CH_2CH_2OCH_2CH_2)$;
$R_6$ is H, $C_1$ to $C_4$ alkyl, $C_1$ to $C_4$ haloalkyl, $C_2$ to $C_4$ alkenyl, $C_2$ to $C_4$ haloalkenyl, phenyl, benzyl, phenyl optionally substituted with W or benzyl optionally substituted with W;
$R_7$ is H, $C_1$ to $C_4$ alkyl, $C_2$ to $C_4$ alkenyl, $C_2$ to $C_4$ alkynyl, $C_2$ to $C_4$ alkylcarbonyl, $C_2$ to $C_4$ alkoxycarbonyl, $C_1$ to $C_4$ alkylsulfonyl;
X is O or S;
n is 1 to 4;
m is 1 to 5;
p is 1 to 3;

q is 0 to 2; and

Y is H, $C_1$ to $C_6$ alkyl, benzyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, or phenylthio substituted with 1 to 3 substituents independently selected from W.

Preferred compound (A) are those of Formula I wherein Q is

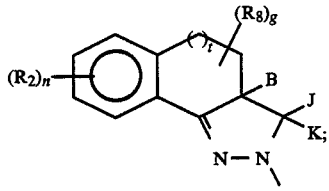
Q-1

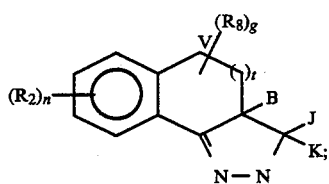
Q-2

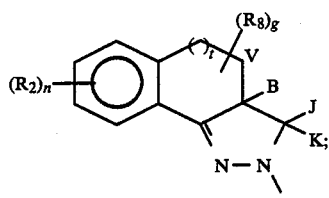
Q-3

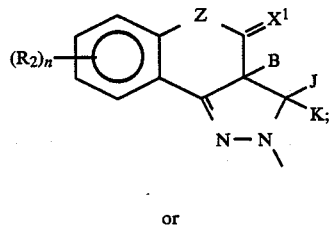
Q-4 or

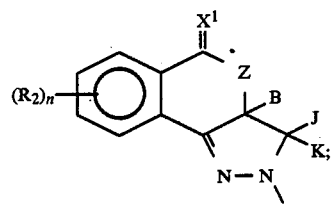
Q-5

X is O or S;
$X^1$ is O or S;
t is 0, 1 or 2;
V is O, $S(O)_q$, or $NR_6$;
Z is O or $NR_6$.
$R_8$ is H, halogen, $C_1$-$C_6$ alkyl, $C_2$-$C_4$ alkoxycarbonyl, phenyl or phenyl substituted by 1-3 substituents selected from W; and
g is 0, 1 or 2.

Preferred compounds (B) are preferred compounds (A) wherein

B is H, $C_1$ to $C_6$ alkyl, $C_1$ to $C_6$ haloalkyl, $C_2$ to $C_6$ alkenyl, $C_2$ to $C_6$ alkynyl, $C_2$ to $C_6$ alkoxyalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl or phenyl substituted by $(R_5)_p$;

J is H or $CH_3$;

$R_3$ is H, $C_1$ to $C_4$ alkyl, $C_1$ to $C_2$ haloalkyl, $C_3$ to $C_4$ alkenyl, $C_3$ to $C_4$ haloalkenyl, propargyl, phenyl, benzyl, or phenyl or benzyl substituted with one of F, Cl, Br, $CF_3$ or $NO_2$;

$R_6$ is H, $C_1$ to $C_4$ alkyl, allyl or propargyl;

n is 1 or 2;

P is 1 or 2;

m is 1 to 3; and

Y is H, $C_1$ to $C_4$ alkyl, $SCH_3$, $SCCl_3$, $SO_2CH_3$, $SC_6H_5$, 2—$NO_2$—$C_6H_4S$, $C(O)CH_3$, $C(O)CF_3$; $CO_2CH_3$ or $CO_2CH_2CH_3$.

Preferred compounds (C) are preferred compounds (B) wherein

B is H, $C_1$ to $C_4$ alkyl, $C_3$-$C_4$ alkoxycarbonylalkyl, $CO_2R_3$, $C(O)R_3$, phenyl or phenyl substituted by $(R_5)_p$;

J is H;

K is H;

$R_1$ is H, halogen, CN, SCN, $NO_2$, $OR_3$, $SR_3$, $SO_2R_3$, $CO_2R_3$, $C(O)R_3$ or $R_3$ with one $R_1$ substituent in the 4-position, or when m is 2 then $R_1$ can be taken together as —$CH_2C(CH_3)_2O$—, $OCH_2CH_2O$—, $OCF_2CF_2O$— or —$CF_2CF_2O$— to form a 5 or 6 membered fused ring;

$R_2$ and $R_5$ are H, $R_3$, halogen, CN, SCN, $NO_2$, $OR_3$, $SR_3$, $SO_2R_3$, $OC(O)R_3$, $OSO_2R_3$, $CO_2R_3$, $C(O)R_3$, $C(O)NR_3R_4$, $SO_2NR_3R_4$ or $NR_3R_4$;

$R_3$ is $C_1$-$C_4$ alkyl, $C_1$-$C_2$ haloalkyl $C_3$-$C_4$ alkenyl or propargyl;

$R_4$ and $R_8$ are H or $CH_3$;

X is O;

X' is O;

m is 1 or 2;

t is 1; and q is 0.

Preferred compounds (D) are preferred compounds (C) wherein $R_1$ is Cl, F, Br, $CF_3$, CN, $OCF_3$, $OCF_2H$ or $SCF_2H$;

$R_2$ is H, Cl, F, Br, CN, $CF_3$, $CH_3$, $OCF_2H$, $OCF_3$, $SCH_3$, $SCF_2H$, $SO_2CH_3$ or $NO_2$;

$R_6$ is H or $CH_3$;

B is H, $CH_3$, $CH_2CH_3$, $CO_2CH_3$, $CO_2CH_2CH_3$, phenyl or phenyl substituted by halogen, CN, $CF_3$ or $NO_2$, and;

Y is H.

Preferred compounds (E) are preferred compounds (D) wherein

Q is Q-1.

Preferred compounds (F) are preferred compounds (D) wherein

Q is Q-2;

Specifically preferred compounds are preferred compounds (E):

Methyl 3,3a,4,5-tetrahydro-2-[[4-(trifluoromethyl)-phenylamino]carbonyl]-2H-benz[g]indazole-3a-carboxylate. (G)

Methyl 7-chloro-3,3a,4,5-tetrahydro-2-[[4-trifluoromethyl)phenylamino]carbonyl]2H-benz[g]indazole-3a-carboxylate, (H)

7-Chloro-3,3a,4,5-tetrahydro-N-[4-(trifluoromethyl)-phenyl]-2H-benz[g]indazole-2-carboxamide, (I)

Methyl 6-fluoro-3,3a,4,5-tetrahydro-2-[[4-(trifluoromethyl)phenylamino]carbonyl]-2H-benz[g]indazole-3a-carboxylate, (J).

The compound of this invention, in addition to being useful as foliar and/or soil insecticides, can be combined with other pesticides for agricultural uses that will readily occur to one skilled in the art. Reference to compounds of this invention or to compounds of Formula I includes geometric and stereoisomers thereof as well as agriculturally suitable salts which, for brevity only, are not referred to specifically hereafter.

DETAILS OF THE INVENTION

For descriptive purposes, the following numbering system will be used to describe the values of Q in both the discussion and tables that follow.

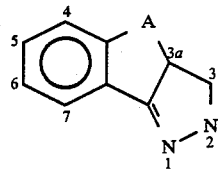

Compounds of Formula I can be prepared by the reaction of aryl isocyanates of Formula II and substituted indazoles of Formula III as shown in Scheme I. Typical reactions involve the combination of equimolar amounts of II and III in conventional organic solvents including ether, tetrahydrofuran (THF), methylene chloride, chloroform and benzene, The reaction can be run at temperatures ranging from about $-20°$ C. to 100° C. with temperatures in the range of about $-10°$ to 30° C. generally preferred.

SCHEME 1

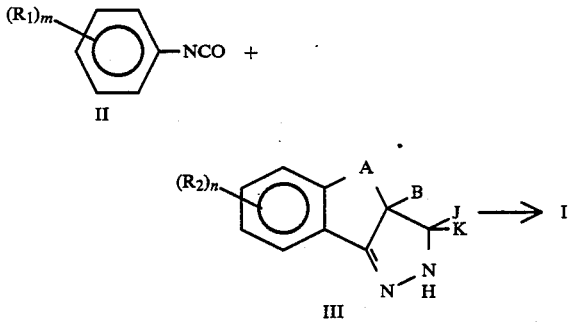

Substituted indazoles of Formula III, where B is equal to H, can be prepared by the reaction of hydrazine with an α, β-unsaturated ketone of Formula IV (or their precursors) by procedures well documented in the chemical literature (Scheme 2). For a review of pyrazoline synthesis, see El-Rayyes and Al-Awadi. Synthesis, 1028 (1985). For literature describing the synthesis of 3,4- and 3,5-disubstituted pyrazolines, which can be applied to the synthesis of compounds of Formula III, where B is H, see U.S. Pat. 3,991,073 and U.S. Pat. 4.070.365.

SCHEME 2

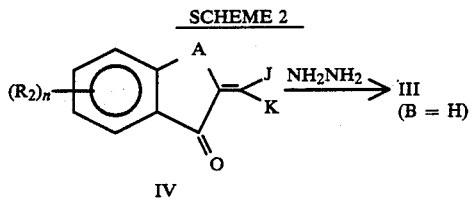

Preparation of compounds of Formula I, where B is other than H, $OR_7$ phenyl or substituted phenyl can be achieved by metallation of the 3a- position of Formula I (where B is H) followed by reaction with a suitable electrophile as depicted in Scheme 3. Procedures for the related transformation of 4-substituted pyrazolines to 4,4-disubstituted pyrazolines are reported in European patent application No. 153127 and can be applied to substituted indazoles of Formula I. Metallation can be accomplished by deprotonation with a strong base, in a suitable solvent and at temperatures ranging from $-78°$ C. to 100° C. Useful base for this reaction includes lithium dialkylamides such as lithium diisopropylamide and lithium tetramethylpiperide, alkyl lithium reagents such as n-butyllithium and metal hydrides such as sodium hydride and potassium hydride. Deprotonation of compounds of Formula I, where B is equal to hydrogen, may require two equivalents of base when Y is equal to hydrogen. The reaction can be conducted in many conventional organic solvents and in certain instances a cosolvent may be useful. Suitable solvents include diethylether, tetrahydrofuran, tetrahydropyran, dimethylformamide, hexamethylphosphoramide, benzene and the like. Suitable electrophilic reagents for reaction with the metallated Formula I compounds include alkyl and substituted alkyl halides, alkyl chloroformates, acyl halides, isocyanates, dialkyl carbamoylhalides and related electrophiles which will be known to those skilled in the art.

SCHEME 3

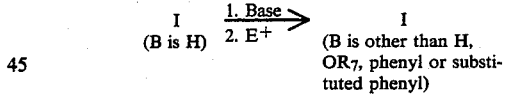

Where $E^+$ is an electrophilic reagent.

An alternative Procedure for introduction of the 3a-substituent, which in certain instances may be preferred over that of scheme 3 due to higher yields and/or greater ease of synthesis. Proceeds via the intermediacy of compound V, wherein the 2-nitrogen has been derivatized with a suitable protecting group. Deprotonation with a strong base such as lithium diisopropylamide, typically in stoichiometric quantities, followed by reaction with any of the previously described electrophiles provides compounds of Formula V where B is other than hydrogen, $OR_7$, phenyl or substituted phenyl. Removal of the nitrogen protecting group provides the required Formula III intermediate. Nitrogen-protecting groups are well documented in the chemical literature, as are procedures for their preparation and cleavage. Examples include acetyl, trifluoroacetyl, benzoyl, substituted benzoyl, alkoxycarbonyl, benzyl and substituted benzyl. For a review see Greene "Protective Groups in Organic Synthesis" New York: John Wiley and Sons, 1981) pp. 218 to 287.

SCHEME 4

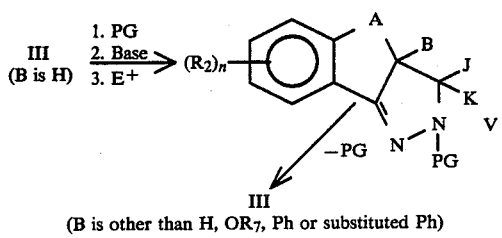

(B is other than H, OR$_7$, Ph or substituted Ph)

where E$^+$ is an electrophile and PG is representative of a suitable nitrogen-protecting group.

Formula III compounds where B is equal to hydroxy are prepared by the reaction of hydrazine with a suitably substituted epoxide of Formula VI (Scheme 5, Reaction 1). The epoxides are available from the enones of Formula IV by Procedures known in the art, the most widely employed method being epoxidation via the use of alkaline hydrogen peroxide (see, e.g., Wasson and House, Org. Syn., Coll. Vol. 4, 552 (1963)).

Compounds of Formula III where B is equal to OR$_7$ and R$_7$ is other than hydrogen, may be prepared from the Formula III compounds where B is equal to hydroxy via reaction with electrophilic reagents such as alkyl halides, acyl halides, alkyl chloroformates. chlorosulfonates, isocyanates and dialkyl carbamoylhalides (Scheme 5, Reaction 2). Those skilled in the art will recognize that conditions necessary for this transformation including solvent, catalyst, temperature, etc., will vary with the specific electrophile chosen and that protection of the 2-nitrogen may be necessary.

SCHEME 5

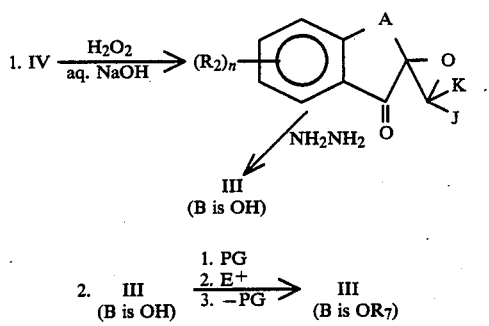

where E$^+$ and PG are as previously defined.

Compounds of Formula III where B is phenyl or substituted phenyl may be prepared by reaction of a substituted ketone of Formula VIII with hydrazine. The Formula VIII compounds are in turn prepared from compounds of Formula VII in a two-step process involving first an aldol or Mannich type reaction on the Formula VII compound followed by conversion of the hydroxyl or dialkylamino group to a leaving group L, examples of which include conversion to the chloride, bromide, tosylate or mesylate by procedures well known in the art.

SCHEME 6

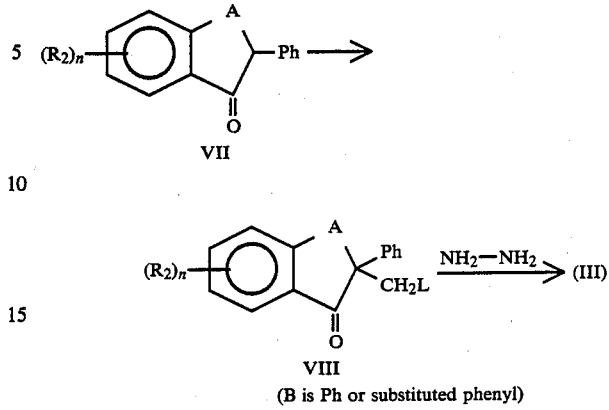

(B is Ph or substituted phenyl)

Compounds of Formula IV (or their precursors) are readily prepared from compounds of Formula IX via an aldol condensation followed by dehydration of the aldol, or when J and K are hydrogen via a Mannich reaction followed by elimination of the dialkylamino group. For a general review of these reactions, see March, "Advanced Organic Chemistry", 3rd ed., (New York: John Wiley and Sons, 1985) pp. 829 to 834, and House, "Modern Synthetic Reactions", 2nd ed., (Menlo Park. CA: N. A. Benjamine, 1972) pp. 655 to 660.

SCHEME 7

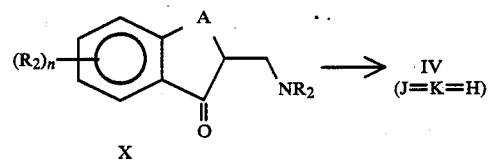

Those skilled in the ar twill recognize the intermediates of Formula IX, which include compounds such as indanones, tetralines, chromanones, thiochromanones, and the like are well documented in the chemical literature as are procedures for their preparation. Selected examples of Formula IX are available commercially as well. The following Examples further illustrate the invention.

EXAMPLE 1

3,3a, 4,5-Tetrahydro-N-[4-trifuloromethyl)phenyl]-2H-benz[z]indazole-2-carboxamide A mixture of 10.0 g of α-tetralone, 2.0 g of paraformaldehyde, 6.5 g of dimethylamine hydrochloride and 1.75 ml of conc. HCl in 20 ml of ethanol was heated at reflux for 24 h, cooled to room temperature and then partitioned between ether and water. The aqueous extracts were made basic with 1N aqueous NaOH and extracted with ether. The ether extracts were dried over magnesium sulfate and concentrated to 12.3 g of a yellow oil. The residual oil was dissolved in 40 ml of n-propyl alcohol, combined with 6.7 ml of hydrazine hydrate and heated at reflux for 1 h. The reaction mixture was then concentrated under vacuum, partitioned between 5% aqueous NaHCO₃ and methylene chloride and dried over magnesium sulfate. To the methylene chloride extracts were added 12.5 g of 4-trifluoromethylphenyl isocyanate and the mixture was then refluxed one hour, cooled to room temperature and concentrated to 26.1 g of a brown oil. Chromatography on silica gel followed by trituration with ether afforded 11.78 g of the title compound as a tan powder, m.p. 149°–151° C. $^1$H NMR (CDCl₃), δ 1.9 (m,1H), 2.4 (m,1H), 3.0 (m,2H), 4.4 (m,1H), 7.3 (m,3H), 7.58 (d,2H), 7.65 (d,2H), 8.0 (d,2H), 8.3 (bs,1H).

EXAMPLE 2

3.3a,4,5-tetrahydro-3a-methyl-N-[4-(trifluoromethyl)-phenyl]-2H-benz[q]indazole-2-carboxamide To a solution of 0.9 ml of diisopropylamine in 10 ml of THF, at −78° C., was added 2.3 ml of 2.5 M n-butyl lithium in hexane and the mixture was stirred for 5 mins. To this −78° C. solution was added a solution of 1.0 g of the title compound of Example 1 in 5 ml of THF. The reaction was warmed to 0° C. recooled to −78° C. and then 0.4 ml of methyl iodide was added. The reaction mixture was then stirred for 24 h, with gradual warming to room temperature, quenched with 0.5 ml of glacial acetic acid, and poured into a 5% solution of aqueous NaHCO₃. The mixture was extracted with chloroform, dried over magnesium sulfate and concentrated. Crystallization from 1:1 ethylacetate/hexane afforded 0.41 g of a yellow solid, m.p. 130° to 135° C. Chromatography of the filtrate on silica gel with 30% ethyl acetate hexane afforded an additional 0.17 g of a higher purity sample of the title compound, m.p. 152.5° to 153.5°C. $^1$H NMR (CDCl₃), δ 1.29 (s, 3H), 2.1 (m,2H), 2.9–3.3 (m, 2H), 3.70 (d, 1H), 4.12 (d,1H), 7.3 (m,3H), 7.57 (d,2H). 7.68 (d,2H), 7.98 (d,1H), 8.3 (bs,1H).

EXAMPLE 3

Methyl 3,3a,4,5-tetrahydro-2-[[4-(trifluoromethyl)-phenylamino]carbonyl]-2H-benz[g]indazole-3a-carboxylate Application of the procedure of Example 2 with 0.75 ml of methyl chloroformate afforded, after chromatography on silica gel, 0.25 g of the title compound as a white solid m P. 177° to 180° C. $^1$H NMR (CDCl₃), δ 2.1 (m,1H), 2.7 (m,1H), 3.0 (m,2H), 3.71 (s,3H), 3.76 (d,1H), 4.58 (d,1H), 7.3 (m,3H), 7.57 (d,2H), 7.66 (d,2H), 8.0 (d,1H), 8.22 (s,1H),

EXAMPLE 4

7-Chloro-3,3a,4,5-tetrahydro-N-[4-(trifluoromethyl)-phenyl]-2H-benz[g]indazole-2-carboxamide Step A: ((2-(3-chlorophenyl)ethyl)methanesulfonate To a 0° C. solution of 30.0 g of 3-chlorophenethyl alcohol and 15.3 ml of methane sulfonyl chloride in 150 ml of THF was added, dropwise, a solution of 28.0 ml of triethylamine in 50 ml of THF. The reaction was warmed to room temperature, stirred overnight, and then filtered. The filtrate was partitioned between aqueous sodium bicarbonate and ether. The organic extracts were then dried over magnesium sulfate, filtered concentrated under reduced pressure to afford 45.93 g of a clear, colorless oil. $^1$NMR was consistent with the structure for Step A.

Step B: 3-chlorobenzenebutanoic acid

To a mixture of 8.0 g of 60% sodium hydride in 300 ml of THF, under N₂, was added dropwise a solution of 31.0 ml of diethyl malonate in 50 ml of THF. Upon complete addition of the diethyl malonate, a pale yellow homogeneous solution was obtained. To this was added a solution of 45.93 g of the sulfonate from Step A and the mixture was then heated at reflux overnight. The reaction was then cooled to room temperature, poured into 400 ml of 1N HCl, and extracted with ether. The ether extracts were dried over magnesium sulfate, filtered and concentrated under reduced pressure to afford 68.9 g of a yellow oil. The crude oil was dissolved in 400 ml of methanol, 100 ml of H₂O and 40 ml of 50% aqueous NaOH. The reaction was stirred overnight and the methanol was then removed at reduced pressure. The crude residue was partitioned between H₂O and ether, the aqueous extracts were acidified with concentrated HCl and then extracted several times with ether. The ether extracts were dried over magnesium sulfate, filtered and concentrated to afford 51.7 g of a yellow oil. The crude residue was dissolved in 200 ml of toluene and heated at reflux for 4 days under N₂ to effect decarboxylation. After this time toluene was removed by concentration at reduced pressure to afford 35.72 g of a yellow oil. $^1$H NMR analysis of the crude product was consistent with 3-chlorobenzenebutanoic acid of purity estimated to be 80%. The crude product was used without further purification directly in the next step.

Step C: 6-chloro-3,4-dihydro-1-(2H)-naphthalenone

A mixture of 35.72 of the product from Step B and 50 ml of thionyl chloride was heated at reflux for 2 hours and then stirred at room temperature for 18 hrs. After this time thionyl chloride was removed at reduced pressure and the product was dissolved in carbon tetrachloride and concentrated at reduced pressure. The residue was dissolved in 150 ml of dichloroethane cooled to 0° C. and 28 g of aluminum chloride was added portionwise over about 1 hr in approximately 3 g portions. After stirring for 3 hrs the reaction was poured over a mixture of ice/1N HCl and extracted three times with methylene chloride. The organic extracts were dried over magnesium sulfate and concentrated to approximately 30 g of a brown oil. Chromatography on silica gel with 10% ethyl acetate/hexane afforded 17.83 g of 6-chloro-3,4-dihydro-1(2H)-naphthalenone as a brown oil. $^1$H NMR was consistent with the structure.

Step D: 7-chloro-3,3a,4,5-tetrahydro-N-[4-(trifluoromethyl)phenyl]2H-benz[g]indazole-2-carboxamide A mixture of 6-chloro-3,4-dihydro-1(2H)naphthalenone (Step C), 2.5 g of dimethylamine hydrochloride, 1.0 g of paraformaldehyde, 0.7 ml of concentrated HCl and 15 ml of ethanol was combined and heated at reflux for 18 hours. The reaction was then concentrated at reduced pressure and partitioned between H₂O and ether. The aqueous extracts were made basic with 1N NaOH and then extracted three times with ether. The ether extracts were dried over magnesium sulfate and concentrated to 4.64 g of a yellow oil. This compound was dissolved in 25 ml of ethanol and 1.5 ml of hydrazine hydrate was added followed by 5 to 6 drops of 50% solution hydroxide. The reaction was then heated at reflux, under $N_2$, for 2 to 3 hrs after which time it was cooled and most of the ethanol was removed by concentration at reduced pressure. The crude residue was partitioned between saturated aqueous sodium bicarbonate and methylene chloride. The methylene chloride extracts were dried over magnesium sulfate and filtered. The methylene chloride extracts were then combined with 3.5 g of 4-trifluoromethylphenyl isocyanate and stirred under $N_2$ overnight. The reaction was then concentrated and the crude residue triturated with ether to afford 3.35 g of the title compound as a white powder, m.p. 196° to 199° C. $^1$H NMR(CDCl$_3$) δ 1.9 (m, 1H), 2.2 (m, 1H), 3.0 (m, 2H), 3.5 (m, 2H), 4.43 (m, 1H), 7.24 (m, 2H), 7.55 (d, 2H), 7.67 (d, 2H), 7.92 (d, 1H), 8.20 (s, 1 H).

EXAMPLE 5

Methyl 7-chloro-3,3a,4,5-tetrahydro-2-[[4(trifluoromethyl)-phenylamino]carbonyl]-2H-benz[g]-indazole-3a-carboxylate A solution of 50 ml of THF and 6.7 ml of diisopropylamine was cooled under $N_2$ to −78° C. and then 17.5 ml of 2.5 M n-butyllithium in hexane was added. After 5 min. a solution of 7.8 g of the title compound of Example 4 in 15 ml of THF was added dropwise and the dark red solution that formed was stirred at −78° C. for an additional 15 min. After this time a solution of 4.6 ml of methyl chloroformate in 10 ml of THF was added dropwise and the red color dissipated rapidly. The reaction was warmed to room temperature and after 1 hr quenched with 5% aqueous sodium bicarbonate. The reaction mixture was partitioned between ether and 5% aqueous sodium bicarbonate. The ether extracts were dried over magnesium sulfate and concentrated to 14.1 g of a yellow oily solid. The crude product was triturated with ether and the resulting white precipitate was filtered and dried to afford 5.56 g of the title compound as a white solid, m.p. 234° C. to 236° C. $^1$H NMR(CDCl$_3$) δ 2.1 (m, 1H), 2.75 (m, 1H) 2.95 (m, 2H), 3.71 (s, 3H), 3.75 (d, 1H, J=6Hz), 4.59 (d, 1H, J=6Hz), 7.25 (m, 2H), 7.57 (d, 2H), 7.66 (d, 2H), 7.94 (d, 1H), 8.18 (d, 1H),

EXAMPLE 6

7-chloro-2,3,3a,4-tetrahydro-N-[4-(trifluoromethyl)-phenyl]-[1]benzothiodyrano[4.3-c]pyrazole-2-carboxamide Step A: 7-chloro-3-[(dimethylamino)methyl]-2,3-dihydro-4H-1-benzothiopyran-4-one A mixture of 15.0 g (75.7 mmol) of 7-chlorothiochroman-4-one (Chu et al., Hua Hsüeh Hsüeh Pao. 1956, 22, 371–8; Chem. Abstracts. 1958, 52, 11044a). 7.41 g 190.8 mmol) of dimethylamine hydrochloride. 3.41 g (113 mmol) of paraformaldehyde, and 1.26 ml (15 mmol) of concentrated HCl in 25 ml of ethanol under a nitrogen atmosphere was heated under reflux for 22 hrs. The reaction mixture was poured into 150 ml of water and extracted with ether (2×50 ml). The aqueous layer was made basic (pH 10) with 1N NaOH and then was extracted with ethyl acetate (3×100 ml ). After being dried (MgSO$_4$), these ethyl acetate extracts were concentrated under reduced pressure to give 14.9 g of a yellow solid. The $^1$H NMR was consistent with the structure for the title compound.

Step B: 7-chloro-2,3,3a,4-tetrahydro-N-[4-(trifluoromethyl)phenyl]-[1]benzothiopyrano[4.3-c] pyrazole-2-carboxamide To a stirred mixture of 14.0 g (54.7 mol) of the Mannich base from Step A and 6.19 ml (6.38 g, 110 mmol) of hydrazine hydrate in 36 ml of n-propanol under a nitrogen atmosphere was added 0.29 ml (5.5 mmol) of 50% aqueous NaOH and the resulting mixture was heated at 100° C. for 2 hrs. The reaction mixture was concentrated under reduced pressure, diluted with 250 ml of dichloromethane, and washed with 200 ml of dilute aqueous sodium bicarbonate. The aqueous layer was extracted with 50 ml of dichloromethane. The combined organic layers were dried (MgSO$_4$) and filtered to give 370 ml of solution. A 120 ml portion of this solution was treated under a nitrogen atmosphere with 3.75 g (20.0 mmol) of 4-(trifluoromethyl)pbenyl isocyanate and allowed to stir overnight. The reaction mixture was concentrated under reduced pressure, and the residue was triturated with 35 ml of ether and filtered to give 4.51 g (63%) of the title compound as a yellow solid melting at 188° to 192° C. $^1$H NMR (CDCl$_3$, 200 MHz) δ 3.19 (dd, 4.5 Hz, 12.6 Hz, 1H), 3.32 (t, 12.0 Hz, 1H), 3.69 (t, 10.8 Hz, 1H), 3.86 (dq, 4.5 Hz, 11Hz, 1H), 4.43 (t, 10.5 Hz, 1H), 7.13 (dd, 1.9 Hz, 8.8 Hz, 1H), 7.24 (d, 1.9 Hz, 1H) 7.58 (d, 8.8 Hz, 1H), 7.66 (d, 8.8 Hz, 2H), 7.93 (d, 8.4 Hz, 1H), 8.13 (s, 1H).

EXAMPLE 7

7-chloro2,3,3a, 4-tetrahydro-4,4-dimethyl-N-[4-(trifluoromethyl)-phenyl]-[1]benzothiopyrano[4,3-c]pyrazole2-carboxamide Step A: 3-(3-chlorophenylthio)-3-methylbutanoic acid A mixture of 20.0 g (138 mmol) of 3-chlorothiophenol, 13.85 g (138 mmol) of 3-methyl-2-butanoic acid, and 4.1 ml (3.5 g, 42 mmol) of piperidine under a nitrogen atmosphere was heated under reflux at 105° C. for 28 hrs. The reaction mixture was poured into 200 ml of ether and washed with 1N HCl (2×80 ml) and then the aqueous layers were extracted with 50 ml of ether. The combined organic layers were dried (MgSO$_4$) and concentrated under reduced pressure to give 33.1 g of a yellow oil. The 1H NMR was consistent with the structure for the title compound.

Step B: 7-chloro-2,3-dihydro-2,2-dimethyl-4H-1-benzothiopyran-4-one

To 270 g of polyphosphoric acid heated to 70° C. was added, portionwise, 31.9 g of the product from Step A over 15 min with mechanical stirring under a nitrogen atmosphere. After heating at 70° C. for an additional 45 min, the reaction mixture was cooled to 0° C. and 150 ml of water was carefully added followed by 100 ml of ether. The resulting mixture was further diluted with 170 ml of water and 110 ml of ether. The layers were separated and the aqueous layer was extracted with ether (2×200 ml). The combined ether layers were washed with 100 ml of 1N NaOH and were then dried (MgSO$_4$) and concentrated under reduced pressure to give 25.8 g of a yellow solid. The $^1$H NMR was consistent with a 68:32 mixture of the structure for Step B and its 5-chloro isomer, respectively.

Step C: 7-chloro-3-[(dimethylamino)methyl]-2,3-dihydro-2,2-dimethyl-4H-1-benzothiopyran-4-one A mixture of 10.0 g (44.1 mmol) of the isomeric thiochromanones from Step B, 1.99 g (66.2 mmol) of paraformaldehyde 4.32 g (52.9 mmol) of dimethylamine hydrochloride, and 0.74 ml of concentrated HCl in 15 ml of ethanol under a nitrogen atmosphere was heated under reflux for 49 hours. The reaction mixture was poured into 1000 ml of water and extracted with ether (5×200 ml). The aqueous layer was made basic (pH 10) with 1N NaOH and then extracted with ethyl acetate (3×200 ml). After being dried (MgSO4), these ethyl acetate extracts were concentrated under reduced pressure to give 3.59 g of an oil. The $^1$H NMR was consistent with a 80:20 mixture of the structure for the title compound of Step C and its 5-chloro isomer, respectively.

Step D: 7-chloro-2,3,3a,4-tetrahydro-4,4-dimethyl-N-[4-(trifluoromethyl)phenyl]-[1]benzothiopyrano[4,3-c]pyrazole-2-carboxamide To a stirred mixture of 3.20 g (111.3 mmol) of the Mannich bases from Step C and 1.28 ml (1.32 g, 22.6 mmol) of hydrazine hydrate in 7.5 ml of n-propanol under a nitrogen atmosphere was added 90 mg (1.1 mmol) of 50% aqueous NaOH and the resulting mixture was heated at 100° C. for 2 hrs. The reaction mixture was concentrated under reduced pressure, diluted with 50 ml of dichloromethane, and washed with 100 ml of dilute aqueous sodium bicarbonate. The aqueous layer was extracted with 20 ml of dichloromethane. The combined organic layers were dried (MgSO4) and filtered to give 93 ml of solution. A 27 ml portion of this solution was treated with 0.68 g (3.6 mmol) of 4-(trifluoromethyl)phenyl isocyanate and allowed to stir at room temperature for 2.5 hrs. The reaction mixture was concentrated under reduced pressure, and the residue was triturated with 15 ml of ether and filtered to give 1.03 g (71%) of the title compound as a yellow solid, m.p. 200° C. to 202° C. $^1$H NMR (CDCl3, 200 MHz) δ 1.35 (s, 3H), 1.45 (s, 3H), 3.83 (m, 2H), 4.21 (m, 1H), 7.14 (dd, 2.0 Hz, 8.4 Hz, 1H), 7.22 (d, 1.8 Hz, 1H), 7.58 (d, 8.8 Hz, 2H), 7.66 (d, 8.9 Hz, 2H), 7.95 (d, 8.1 Hz, 1H), 8.13 (s, 1H).

EXAMPLE 8

3a-(4-chlorophenyl)-3,3a,4,5-tetrahydro-N-[4-(trifluoromethyl)phenyl]-2H-benz[q]indazole-2-carboxamide Step A: 4-chloro-2-(2-phenylethyl)benzeneacetic acid, methyl ester To a solution of 4.35 g of 60% sodium hydride in 50 ml of DMF was added dropwise 20.0 g of methyl 4-chlorophenyl acetate in 25 ml of DMF. Once the evolution had ceased a mixture of 20.0 g of 2-bromoethyl benzene in 25 m of DMF was added and the reaction was stirred at room temPerature overnight. The reaction was then partitioned between 400 ml of ether and 200 ml of H2O. The ether extracts were washed with H2O, dried over magnesium sulfate, filtered and concentrated to 32.9 g of a yellow oil. Chromatography on silica gel with 5% ethyl acetate in hexane afforded 12.6 g of the title compound as a clear, colorless oil.

Step B: 2-(4-chlorophenyl)-3,4-dihydro-1(2H)naphthalenene

A mixture of 12.6 g of the title compound from Step A, 100 ml of methanol, 30 ml of H2O and 10 ml of 50% NaOH were refluxed under N2 overnight. The reaction was then concentrated at reduced pressure and concentrated HCl was added until acidic. The mixture was extracted three times with ether, dried over magnesium sulfate and concentrated to afford 12.14 g of a yellow oil. The residue was dissolved in 20 ml of thionyl chloride and heated at reflux under N2, overnight. Thionyl chloride was removed by concentration at reduced pressure and the residue was concentrated twice from carbon tetrachloride. The crude product was dissolved in 50 ml of dichloroethane, cooled under N2 to 0° C. and 5.9 g of aluminum trichloride was added. The reaction was stirred overnight at room temperature, poured into 50 ml of 1N HCl and extracted with methylene chloride. The organic extracts were dried over magnesium sulfate, filtered and concentrated to 12.3 g of a brown solid. Chromatography on silica gel with 10% ethyl acetate/hexane followed by trituration with methanol afforded 5.51 g of the title compound as a brown solid, m.p. 97° to 99° C.

Step C: 2-(4-chlorophenyl)-3,4-dihydro-2-(hydroxymethyl)-1(2H)-naphthalenone

To 10 ml of ethanol was added a solution of 1.0 g of the title compound from Step B in 2 ml of toluene followed by 1.5 ml of 37% formaldehyde and then 7.8 ml of 0.5 M NaOH. The reaction was stirred at room temperature, under N2, for four hours after which time TLC confirmed disappearance of the starting tetralone. The reaction was poured into a mixture of 100 ml 5% aqueous sodium bicarbonate and 100 ml of ethyl acetate. The aqueous extracts were washed twice with ethyl acetate, the organic extracts were then dried over magnesium sulfate, filtered and concentrated at reduced pressure. Chromatography on silica gel with 20% ethyl acetate/hexane afforded 1.19 g of a brown oil. $^1$H NMR was consistent with the structure of the title compound.

Step D: 2-(4-chlorophenyl)-3,4-dihydro-2-[(methylsulfonyloxy)methyl]-1(2H)-naphthalenone To a mixture of 0.99 g of the title compound of Step C and 0.6 ml of methanesulfonyl chloride in 20 ml of THF at 0° C. was added 1.05 ml of triethylamine. The reaction was stirred overnight at room temperature, partitioned between 5% aqueous sodium bicarbonate and chloroform, dried over magnesium sulfate and concentrated. The residue was chromatographed on silica gel with 30% ethyl acetate/hexane to afford 1.1 g of the title compound as a viscous yellow oil.

Step E: 3a-(4-chlorophenyl)-3,3a,4,5-tetrahydro-N-[4-(trifluoromethyl)phenyl]-2H-benz[g]indazole-2-carboxamide A mixture of 0.9 g of the title compound of Step D, 10 ml of ethanol and 0.4 ml of hyrazine hydrate was refluxed under N2 for 4 days. The reaction was cooled to room temperature and the white precipitate which formed was filtered. The filtrate was partitioned between saturated aqueous potassium bicarbonate and ethyl acetate. The organic extracts were dried over magnesium sulfate, filtered and concentrated at reduced pressure to afford 0.58 g of a gummy yellow solid. The crude residue was dissolved in 5 ml of THF and 0.4 ml of 4-trifluoromethylphenyl isocyanate was added. After 15 minutes TLC on silica gel (30% ethyl acetate/hexane) indicated formation of a fluorescent product. Concentration of the reaction mixture under reduced pressure and chromatography on silica gel with 20% ethyl acetate/hexane followed by chromatography on silica gel with 10% methylene chloride in n-butylchloride afforded after trituration with hexane 49.2 mg of a beige powder. $^1$H NMR was consistent with the structure of the title compound. $^1$ NMR (CDCl3 ) w 2.30 (dt, 1H), 2.5–2.9 (m, 3H), 3.90 (d, 1H), 4.33 (d, 1 H), 7.14 (m, 3H), 7.2–7.4 (m, 3H), 7.56 (d, 2H), 7.65 (d, 2H), 8.11 (m, 1 H), 8.28 1H).

By the general Procedures described herein, or obvious modifications thereof, the compounds of Tables 1 through 18 can be prepared.

General Structures for Tables 1-18

| Table | Q |
|---|---|
| | 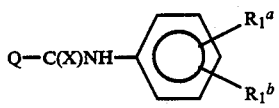 |
| 1 | Q-1 (J = K = H, $R_8$ = H) |
| 2 | Q-2 (J = K = H, $R_8$ = H) |
| 3 | Q-3 (J = K = H, $R_8$ = H) |
| 4 | Q-4 (J = K = H, X = O, $X^1$ = O) |
| 5 | Q-5 (J = K = H, X = O, $X^1$ = O) |
| | 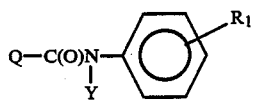 |
| 6 | Q-1 (J = K = H) |
| 7 | Q-2 (J = K = H) |
| 8 | Q-3 (J = K = H) |
| 9 | Q-4 (J = K = H, $X^1$ = O) |
| 10 | Q-5 (J = K = H, $X^1$ = O)) |
| | 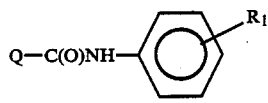 |
| 11 | Q-1 |
| 12 | Q-2 |
| 13 | Q-3 |
| 14 | Q-4 ($X^1$ = O) |
| 15 | Q-5 ($X^1$ = O) |
| 16 | 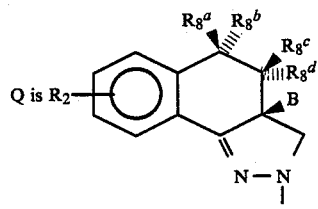 |
| 17 | 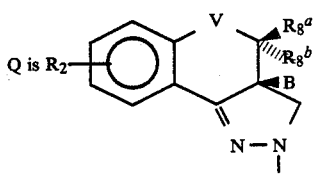 |
| 18 | 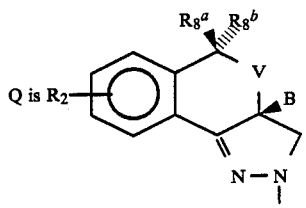 |

For the tables that follow, the values of Q will be numbered as shown:

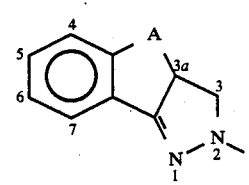

For Tables 16, 17 and 18 only one of the two possible enantiomers of Q is shown for clarity. For compounds in Tables 17 and 18, when V is SO, the α isomer represents compounds where the B substituent is cis to the oxygen of the sulfoxide. The β isomer represents those compounds where the B substituent is trans to the oxygen of the sulfoxide.

TABLE 1

| $R_1^a$ | $R_1^b$ | $R_2$ | B | x | t | Phys. Prop. (m.p. °C.) |
|---|---|---|---|---|---|---|
| H | H | H | H | O | 0 | |
| 4-Cl | H | H | H | O | 0 | |
| 4-F | H | H | H | O | 0 | |
| 4-Br | H | H | H | O | 0 | |
| 4-$CF_3$ | H | H | H | O | 0 | |
| 4-$OCF_2H$ | H | H | H | O | 0 | |
| 4-$CF_3$ | 3-Cl | H | H | O | 0 | |
| 4-$CO_2Me$ | H | H | H | O | 0 | |
| 4-$CO_2$-i-Pr | H | H | H | O | 0 | |
| 4-$NO_2$ | H | H | H | O | 0 | |
| 4-SMe | H | H | H | O | 0 | |
| 4-$SO_2Me$ | H | H | H | O | 0 | |
| 4-$CF_2Cl$ | H | H | H | O | 0 | |
| 4-$OCF_3$ | H | H | H | O | 0 | |
| 4-I | H | H | H | O | 0 | |
| 4-$OCF_2CF_2H$ | H | H | H | O | 0 | |
| 4-CN | H | H | H | O | 0 | |
| 4-Me | H | H | H | O | 0 | |
| 3,4-$CF_2CF_2O$ | | H | H | O | 0 | |
| 3,4-$OCF_2CF_2$ | | H | H | O | 0 | |
| 3,4-$(Me)_2CCH_2O$ | | H | H | O | 0 | |
| 4-Cl | H | H | Me | O | 0 | |
| 4-Br | H | H | Me | O | 0 | |
| 4-$CF_3$ | H | H | Me | O | 0 | |
| 4-SMe | H | H | Me | O | 0 | |
| 4-$OCF_2H$ | H | H | Me | O | 0 | |
| 4-$CF_2Cl$ | H | H | Me | O | 0 | |
| 4-$CO_2$i-Pr | H | H | Me | O | 0 | |

TABLE 1-continued

| $R_1{}^a$ | $R_1{}^b$ | $R_2$ | B | x | t | Phys. Prop. (m.p. °C.) |
|---|---|---|---|---|---|---|
| 4-Cl | H | H | allyl | O | 0 | |
| 4-Br | H | H | allyl | O | 0 | |
| 4-CF$_3$ | H | H | allyl | O | 0 | |
| 4-Cl | H | H | CH$_2$Ph | O | 0 | |
| 4-Br | H | H | CH$_2$Ph | O | 0 | |
| 4-CF$_3$ | H | H | CH$_2$Ph | O | 0 | |
| 4-CF$_3$ | 3-Cl | H | 4-F—CH$_2$Ph | O | 0 | |
| 4-SMe | H | H | 4-F—CH$_2$Ph | O | 0 | |
| 4-Cl | H | H | 4-F—CH$_2$Ph | O | 0 | |
| 4-F | H | H | 4-Cl—CH$_2$Ph | O | 0 | |
| 4-NO$_2$ | H | H | 4-Cl—CH$_2$Ph | O | 0 | |
| 4-OCF$_2$H | H | H | Ph | O | 0 | |
| 4-OCF$_3$ | H | H | Ph | O | 0 | |
| 4-CF$_3$ | H | H | Ph | O | 0 | |
| 4-Cl | 3-Cl | H | 4-Cl-Ph | O | 0 | |
| 4-Br | H | H | 4-Cl-Ph | O | 0 | |
| 4-OMe | H | H | 4-Cl-Ph | O | 0 | |
| 4-CF$_3$ | H | H | n-Bu | O | 0 | |
| 4-Cl | H | H | n-Bu | O | 0 | |
| 4-CF$_3$ | H | H | (CH$_2$)$_3$Cl | O | 0 | |
| 4-Cl | H | H | (CH$_2$)$_3$Cl | O | 0 | |
| 4-Br | H | H | CH$_2$CF$_3$ | O | 0 | |
| 4-OCF$_3$ | H | H | CH$_2$CF$_3$ | O | 0 | |
| 4-SCF$_2$H | H | H | CH$_2$OMe | O | 0 | |
| 4-CF$_3$ | H | H | CH$_2$OEt | O | 0 | |
| 4-Cl | H | H | CH$_2$CO$_2$Me | O | 0 | |
| 4-Br | H | H | CH$_2$CO$_2$Me | O | 0 | |
| 4-OCF$_2$H | H | H | CH$_2$CN | O | 0 | |
| 4-OCF$_2$CF$_2$H | H | H | (CH$_2$)$_2$CN | O | 0 | |
| 4-CF$_3$ | H | H | CO$_2$Me | O | 0 | |
| 4-Cl | H | H | CO$_2$Me | O | 0 | |
| 4-Br | H | H | CO$_2$Me | O | 0 | |
| 4-F | H | H | CO$_2$Me | O | 0 | |
| 4-CF$_2$Cl | H | H | CO$_2$Me | O | 0 | |
| 4-OCF$_3$ | H | H | CO$_2$Me | O | 0 | |
| 3,4-CF$_2$CF$_2$O* | | H | CO$_2$Me | O | 0 | |
| 3,4-OCF$_2$CF$_2$ | | H | CO$_2$Me | O | 0 | |
| 3,4-(Me)$_2$CCH$_2$O | | H | CO$_2$Me | O | 0 | |
| 4-CF$_3$ | H | H | CO$_2$Et | O | 0 | |
| 4-Br | H | H | CO$_2$Et | O | 0 | |
| 4-CF$_3$ | H | H | CO$_2$H | O | 0 | |
| 4-Cl | H | H | CO$_2$H | O | 0 | |
| 4-CF$_3$ | H | H | CO$_2$Ph | O | 0 | |
| 4-F | H | H | CO$_2$Ph | O | 0 | |
| 4-CF$_3$ | H | H | CO$_2$CH$_2$CF$_3$ | O | 0 | |
| 4-CF$_3$ | H | H | CO$_2$CH$_2$CF$_3$ | O | 0 | |
| 4-CF$_3$ | H | H | CO$_2$CH$_2$CN | O | 0 | |
| 4-CF$_3$ | H | H | CO$_2$CH$_2$CN | O | 0 | |
| 4-CF$_3$ | H | H | CO$_2$n-C$_6$H$_{13}$ | O | 0 | |
| 4-CF$_3$ | H | H | CO$_2$allyl | O | 0 | |
| 4-CF$_3$ | H | H | CO$_2$CH$_2$Ph | O | 0 | |
| 4-CF$_3$ | H | H | CO$_2$CH$_2$SMe | O | 0 | |
| 4-CF$_3$ | H | H | C(O)NH$_2$ | O | 0 | |
| 4-Cl | H | H | C(O)NH$_2$ | O | 0 | |
| 4-Br | H | H | C(O)NHMe | O | 0 | |
| 4-OCF$_3$ | H | H | C(O)NHMe | O | 0 | |
| 4-CF$_3$ | H | H | C(O)NMe$_2$ | O | 0 | |
| 4-Cl | H | H | C(O)NMe$_2$ | O | 0 | |
| 4-Br | H | H | C(O)NHEt | O | 0 | |
| 4-OCF$_3$ | H | H | C(S)NH$_2$ | O | 0 | |
| 4-CF$_3$ | H | H | C(S)NHMe | O | 0 | |
| 4-Cl | H | H | C(S)NMe$_2$ | O | 0 | |
| 4-Br | H | H | C(S)Me | O | 0 | |
| 4-OCF$_3$ | H | H | C(S)Et | O | 0 | |
| 4-CF$_3$ | H | H | C(S)NMe$_2$ | O | 0 | |
| 4-Cl | H | H | C(S)NHMe | O | 0 | |
| 4-OCF$_3$ | H | H | OH | O | 0 | |
| 4-CF$_3$ | H | H | OH | O | 0 | |
| 4-Cl | H | H | OH | O | 0 | |
| 4-Br | H | H | OH | O | 0 | |
| 4-OCF$_2$H | H | OH | O | 0 | 0 | |
| 4-CF$_3$ | H | H | OMe | O | 0 | |
| 4-CF$_3$ | H | H | OMe | O | 0 | |
| 4-Cl | H | H | OMe | O | 0 | |
| 4-Br | H | H | O-allyl | O | 0 | |
| 4-OCF$_2$H | H | H | O-allyl | O | 0 | |
| 4-OCF$_3$ | H | H | O-allyl | O | 0 | |
| 4-CF$_3$ | H | H | OAc | O | 0 | |
| 4-Cl | H | H | OAc | O | 0 | |
| 4-Br | H | H | OCONHMe | O | 0 | |

TABLE 1-continued

| $R_1{}^a$ | $R_1{}^b$ | $R_2$ | B | x | t | Phys. Prop. (m.p. °C.) |
|---|---|---|---|---|---|---|
| 4-OCF$_2$H | H | H | OCONMe$_2$ | O | 0 | |
| 4-OCF$_3$ | H | H | OCO$_2$Me | O | 0 | |
| 4-CF$_3$ | H | H | OCO$_2$Ph | O | 0 | |
| 4-Cl | H | H | OSO$_2$Me | O | 0 | |
| 4-Br | H | H | OSO$_2$Me | O | 0 | |
| 4-OCF$_2$H | H | H | OCH$_2$Ph | O | 0 | |
| 4-OCF$_3$ | H | H | OCH$_2$Ph | O | 0 | |
| H | H | H | H | O | 1 | |
| 4-Cl | H | H | H | O | 1 | 91.5 to 96 |
| 4-F | H | H | H | O | 1 | |
| 4-Br | H | H | H | O | 1 | 151 to 152 |
| 4-CF$_3$ | H | H | H | O | 1 | 149 to 151 |
| 4-OCF$_2$H | H | H | H | O | 1 | |
| 4-CF$_3$ | 3-Cl | H | H | O | 1 | |
| 4-CO$_2$Me | H | H | H | O | 1 | |
| 4-CO$_2$-i-Pr | H | H | H | O | 1 | |
| 4-NO$_2$ | H | H | H | O | 1 | |
| 4-SMe | H | H | H | O | 1 | |
| 4-SO$_2$Me | H | H | H | O | 1 | |
| 4-CF$_2$Cl | H | H | H | O | 1 | |
| 4-OCF$_3$ | H | H | H | O | 1 | 104 to 107 |
| 4-I | H | H | H | O | 1 | |
| 4-OCF$_2$CF$_2$H | H | H | H | O | 1 | |
| 4-CN | H | H | H | O | 1 | |
| 4-Me | H | H | H | O | 1 | |
| 3,4-CF$_2$CF$_2$O | | H | H | O | 1 | |
| 3,4-OCF$_2$CF | | H | H | O | 1 | |
| 3,4-(Me)$_2$CCH$_2$O | | H | H | O | 1 | |
| 4-Cl | H | H | Me | O | 1 | |
| 4-Br | H | H | Me | O | 1 | |
| 4-CF$_3$ | H | H | Me | O | 1 | 151.5 to 153.5 |
| 4-SMe | H | H | Me | O | 1 | |
| 4-OCF$_2$H | H | H | Me | O | 1 | |
| 4-CF$_3$ | H | H | Et | O | 1 | 120 to 123 |
| 4-CO$_2$i-Pr | H | H | Me | O | 1 | |
| 4-Cl | H | H | allyl | O | 1 | |
| 4-Br | H | H | allyl | O | 1 | |
| 4-CF$_3$ | H | H | allyl | O | 1 | 158 to 163 |
| 4-Cl | H | H | CH$_2$Ph | O | 1 | |
| 4-Br | H | H | CH$_2$Ph | O | 1 | |
| 4-CF$_3$ | H | H | CH$_2$Ph | O | 1 | 51 to 55 |
| 4-CF$_3$ | 3-Cl | H | 4-F—CH$_2$Ph | O | 1 | |
| 4-SMe | H | H | 4-F—CH$_2$Ph | O | 1 | |
| 4-CF$_3$ | H | H | 4-F—CH$_2$Ph | O | 1 | |
| 4-CF$_3$ | H | H | 4-Cl—CH$_2$Ph | O | 1 | gum |
| 4-NO$_2$ | H | H | 4-Cl—CH$_2$Ph | O | 1 | |
| 4-OCF$_2$H | H | H | Ph | O | 1 | |
| 4-OCF$_3$ | H | H | Ph | O | 1 | |
| 4-CF$_3$ | H | H | Ph | O | 1 | |
| 4-Cl | 3-Cl | H | 4-Cl-Ph | O | 1 | |
| 4-Br | H | H | 4-Cl-Ph | O | 1 | |
| 4-OMe | H | H | 4-Cl-Ph | O | 1 | |
| 4-CF$_3$ | H | H | n-Bu | O | 1 | |
| 4-Cl | H | H | n-Bu | O | 1 | |
| 4-CF$_3$ | H | H | (CH$_2$)$_3$Cl | O | 1 | |
| 4-Cl | H | H | (CH$_2$)$_3$Cl | O | 1 | |
| 4-Br | H | H | CH$_2$CF$_3$ | O | 1 | |
| 4-OCF$_3$ | H | H | CH$_2$CF$_3$ | O | 1 | |
| 4-SCF$_2$H | H | H | CH$_2$OMe | O | 1 | |
| 4-CF$_3$ | H | H | CH$_2$OEt | O | 1 | |
| 4-Cl | H | H | CH$_2$CO$_2$Me | O | 1 | |
| 4-Br | H | H | CH$_2$CO$_2$Me | O | 1 | |
| 4-OCF$_2$H | H | H | CH$_2$CN | O | 1 | |
| 4-OCF$_2$CF$_2$H | H | H | (CH$_2$)$_2$CN | O | 1 | |
| 4-CF$_3$ | H | H | (CH$_2$)$_2$CN | O | 1 | 165 to 169 |
| 4-CF$_3$ | H | H | (CH$_2$)$_3$CN | O | 1 | 186 to 188 |
| 4-CF$_3$ | H | H | CO$_2$Me | O | 1 | 177 to 180 |
| 4-Cl | H | H | CO$_2$Me | O | 1 | 175 to 177 |
| 4-Br | H | H | CO$_2$Me | O | 1 | 175 to 178 |
| 4-F | H | H | CO$_2$Me | O | 1 | |
| 4-CF$_2$Cl | H | H | CO$_2$Me | O | 1 | |
| 4-OCF$_3$ | H | H | CO$_2$Me | O | 1 | |
| 3,4-CF$_2$CF$_2$O | | H | CO$_2$Me | O | 1 | |
| 3,4-OCF$_2$CF$_2$O | | H | CO$_2$Me | O | 1 | |
| 3,4-(Me)$_2$CCH$_2$O | | H | CO$_2$Me | O | 1 | |
| 4-CF$_3$ | H | H | CO$_2$Et | O | 1 | 220 to 222 |
| 4-Br | H | H | CO$_2$Et | O | 1 | 179 to 182 |
| 4-Cl | H | H | CO$_2$Et | O | 1 | 172 to 174 |
| 4-CF$_3$ | H | H | CO$_2$H | O | 1 | 182 to 183 |
| 4-CF$_3$ | H | H | CO$_2$Na | O | 1 | 230 |

TABLE 1-continued

| $R_1{}^a$ | $R_1{}^b$ | $R_2$ | B | x | t | Phys. Prop. (m.p. °C.) |
|---|---|---|---|---|---|---|
| 4-CF$_3$ | H | H | CO$_2$Ph | O | 1 | |
| 4-F | H | H | CO$_2$Ph | O | 1 | |
| 4-CF$_3$ | H | H | CO$_2$CH$_2$CCL$_3$ | O | 1 | 194 to 196 |
| 4-CF$_3$ | H | H | CO$_2$CH$_2$CF$_3$ | O | 1 | |
| 4-CF$_3$ | H | H | CO$_2$(CH$_2$)Cl | O | 1 | 185 to 188 |
| 4-CF$_3$ | H | H | CO$_2$(CH$_2$)$_2$Br | O | 1 | 162 to 167 |
| 4-CF$_3$ | H | H | CO$_2$CH$_2$CN | O | 1 | |
| 4-CF$_3$ | H | H | CO$_2$n-C$_6$H$_{13}$ | O | 1 | |
| 4-CF$_3$ | H | H | CO$_2$allyl | O | 1 | |
| 4-CF$_3$ | H | H | CO$_2$CH$_2$Ph | O | 1 | |
| 4-CF$_3$ | H | H | CO$_2$CH$_2$SMe | O | 1 | |
| 4-CF$_3$ | H | H | C(O)NH$_2$ | O | 1 | 250 |
| 4-Cl | H | H | C(O)NH$_2$ | O | 1 | |
| 4-Br | H | H | C(O)NHMe | O | 1 | |
| 4-OCF$_3$ | H | H | C(O)NHMe | O | 1 | |
| 4-CF$_3$ | H | H | C(O)NMe$_2$ | O | 1 | 226 to 230 |
| 4-Cl | H | H | C(O)NMe$_2$ | O | 1 | |
| 4-Br | H | H | C(O)NHEt | O | 1 | |
| 4-CF$_3$ | H | H | C(O)NHMe | O | 1 | 220 |
| 4-CF$_3$ | H | H | C(O)NHallyl | O | 1 | 250 |
| 4-CF$_3$ | H | H | C(O)N(Me)allyl | O | 1 | 219 to 221 |
| 4-CF$_3$ | H | H | C(O)NHPh-4-Cl | O | 1 | 255 |
| 4-CF$_3$ | H | H | C(O)-piperidinyl | o | 1 | 235 |
| 4-OCF$_3$ | H | H | C(S)NH$_2$ | O | 1 | |
| 4-CF$_3$ | H | H | C(S)NHMe | O | 1 | |
| 4-Cl | H | H | C(S)NMe$_2$ | O | 1 | |
| 4-Br | H | H | C(S)Me | O | 1 | |
| 4-OCF$_3$ | H | H | C(S)Et | O | 1 | |
| 4-CF$_3$ | H | H | C(S)NMe$_2$ | O | 1 | |
| 4-Cl | H | H | C(S)NHMe | O | 1 | |
| 4-OCF$_3$ | H | H | OH | O | 1 | |
| 4-CF$_3$ | H | H | OH | O | 1 | |
| 4-Cl | H | H | OH | O | 1 | |
| 4-Br | H | H | OH | O | 1 | |
| 4-OCF$_2$H | H | H | OH | O | 1 | |
| 4-OCF$_3$ | H | H | OMe | O | 1 | |
| 4-CF$_3$ | H | H | OMe | O | 1 | |
| 4-Cl | H | H | OMe | O | 1 | |
| 4-Br | H | H | O-allyl | O | 1 | |
| 4-OCF$_2$H | H | H | O-allyl | O | 1 | |
| 4-OCF$_3$ | H | H | O-allyl | O | 1 | |
| 4-CF$_3$ | H | H | OAc | O | 1 | |
| 4-Cl | H | H | OAc | O | 1 | |
| 4-OCF$_3$ | H | H | OCO$_2$Me | O | 1 | |
| 4-CF$_3$ | H | H | OCO$_2$Me | O | 1 | |
| 4-Cl | H | H | OSO$_2$Me | O | 1 | |
| 4-Br | H | H | OSO$_2$Me | O | 1 | |
| 4-OCF$_2$H | H | H | OEt | O | 1 | |
| 4-OCF$_3$ | H | H | OEt | O | 1 | |
| H | H | H | H | O | 2 | |
| 4-Cl | H | H | H | O | 2 | 136.5 to 138 |
| 4-F | H | H | H | O | 2 | |
| 4-Br | H | H | H | O | 2 | |
| 4-CF$_3$ | H | H | H | O | 2 | 167 to 168.5 |
| 4-OCF$_2$H | H | H | H | O | 2 | |
| 4-CF$_3$ | 3-Cl | H | H | O | 2 | |
| 4-CO$_2$Me | H | H | H | O | 2 | |
| 4-CO$_2$-i-Pr | H | H | H | O | 2 | |
| 4-NO$_2$ | H | H | H | O | 2 | |
| 4-SMe | H | H | H | O | 2 | |
| 4-SO$_2$Me | H | H | H | O | 2 | |
| 4-CF$_2$Cl | H | H | H | O | 2 | |
| 4-OCF$_3$ | H | H | H | O | 2 | |
| 4-I | H | H | H | O | 2 | |
| 4-OCF$_2$CF$_2$H | H | H | H | O | 2 | |
| 4-CN | H | H | H | O | 2 | |
| 4-Me | H | H | H | O | 2 | |
| 4-Cl | H | H | Me | O | 2 | 137 to 141.5 |
| 4-Br | H | H | Me | O | 2 | |
| 4-CF$_3$ | H | H | Me | O | 2 | 134 to 139 |
| 4-SMe | H | H | Me | O | 2 | |
| 4-OCF$_2$H | H | H | Me | O | 2 | |
| 4-CF$_2$Cl | H | H | Me | O | 2 | |
| 4-CO$_2$i-Pr | H | H | Me | O | 2 | |
| 4-Cl | H | H | allyl | O | 2 | |
| 4-Br | H | H | allyl | O | 2 | |
| 4-CF$_3$ | H | H | allyl | O | 2 | |
| 4-Cl | H | H | CH$_2$Ph | O | 2 | |
| 4-Br | H | H | CH$_2$Ph | O | 2 | |
| 4-CF$_3$ | H | H | CH$_2$Ph | O | 2 | |

TABLE 1-continued

| $R_1{}^a$ | $R_1{}^b$ | $R_2$ | B | x | t | Phys. Prop. (m.p. °C.) |
|---|---|---|---|---|---|---|
| 4-CF$_3$ | 3-Cl | H | 4-F—CH$_2$Ph | O | 2 | |
| 4-SMe | H | H | 4-F—CH$_2$Ph | O | 2 | |
| 4-Cl | H | H | 4-F—CH$_2$Ph | O | 2 | |
| 4-F | H | H | 4-Cl—CH$_2$Ph | O | 2 | |
| 4-NO$_2$ | H | H | 4-Cl—CH$_2$Ph | O | 2 | |
| 4-OCF$_2$H | H | H | Ph | O | 2 | |
| 4-OCF$_3$ | H | H | Ph | O | 2 | |
| 4-CF$_3$ | H | H | Ph | O | 2 | |
| 4-Cl | 3-Cl | H | 4-Cl-Ph | O | 2 | |
| 4-Br | H | H | 4-Cl-Ph | O | 2 | |
| 4-OMe | H | H | 4-Cl-Ph | O | 2 | |
| 4-CF$_3$ | H | H | n-Bu | O | 2 | |
| 4-Cl | H | H | n-Bu | O | 2 | |
| 4-CF$_3$ | H | H | (CH$_2$)$_3$Cl | O | 2 | |
| 4-Cl | H | H | (CH$_2$)$_3$Cl | O | 2 | |
| 4-Br | H | H | CH$_2$CF$_3$ | O | 2 | |
| 4-OCF$_3$ | H | H | CH$_2$CF$_3$ | O | 2 | |
| 4-SCF$_2$H | H | H | CH$_2$OMe | O | 2 | |
| 4-CF$_3$ | H | H | CH$_2$OEt | O | 2 | |
| 4-Cl | H | H | CH$_2$CO$_2$Me | O | 2 | |
| 4-Br | H | H | CH$_2$CO$_2$Me | O | 2 | |
| 4-OCF$_2$H | H | H | CH$_2$CN | O | 2 | |
| 4-OCF$_2$CF$_2$H | H | H | (CH$_2$)$_2$CN | O | 2 | |
| 4-CF$_3$ | H | H | CO$_2$Me | O | 2 | |
| 4-Cl | H | H | CO$_2$Me | O | 2 | |
| 4-Br | H | H | CO$_2$Me | O | 2 | |
| 4-F | H | H | CO$_2$Me | O | 2 | |
| 4-CF$_2$Cl | H | H | CO$_2$Me | O | 2 | |
| 4-OCF$_3$ | H | H | CO$_2$Me | O | 2 | |
| 4-CF$_3$ | H | H | CO$_2$Et | O | 2 | |
| 4-Br | H | H | CO$_2$Et | O | 2 | |
| 4-CF$_3$ | H | H | CO$_2$H | O | 2 | |
| 4-Cl | H | H | CO$_2$H | O | 2 | |
| 4-CF$_3$ | H | H | CO$_2$Ph | O | 2 | |
| 4-F | H | H | CO$_2$Ph | O | 2 | |
| 4-CF$_3$ | H | H | CO$_2$CH$_2$CF$_3$ | O | 2 | |
| 4-CF$_3$ | H | H | CO$_2$CH$_2$CF$_3$ | O | 2 | |
| 4-CF$_3$ | H | H | CO$_2$CH$_2$CN | O | 2 | |
| 4-CF$_3$ | H | H | CO$_2$CH$_2$CN | O | 2 | |
| 4-CF$_3$ | H | H | CO$_2$n-C$_6$H$_{13}$ | O | 2 | |
| 4-CF$_3$ | H | H | CO$_2$allyl | O | 2 | |
| 4-CF$_3$ | H | H | CO$_2$CH$_2$Ph | O | 2 | |
| 4-CF$_3$ | H | H | CO$_2$CH$_2$SMe | O | 2 | |
| 4-CF$_3$ | H | H | C(O)NH$_2$ | O | 2 | |
| 4-Cl | H | H | C(O)NH$_2$ | O | 2 | |
| 4-Br | H | H | C(O)NHMe | O | 2 | |
| 4-OCF$_3$ | H | H | C(O)NHMe | O | 2 | |
| 4-CF$_3$ | H | H | C(O)NMe$_2$ | O | 2 | |
| 4-Cl | H | H | C(O)NMe$_2$ | O | 2 | |
| 4-Br | H | H | C(O)NHEt | O | 2 | |
| 4-OCF$_3$ | H | H | C(S)NH$_2$ | O | 2 | |
| 4-CF$_3$ | H | H | C(S)NHMe | O | 2 | |
| 4-Cl | H | H | C(S)NMe$_2$ | O | 2 | |
| 4-Br | H | H | C(S)Me | O | 2 | |
| 4-OCF$_3$ | H | H | C(S)Et | O | 2 | |
| 4-CF$_3$ | H | H | C(S)NMe$_2$ | O | 2 | |
| 4-Cl | H | H | C(S)NHMe | O | 2 | |
| 4-OCF$_3$ | H | H | OH | O | 2 | |
| 4-CF$_3$ | H | H | OH | O | 2 | |
| 4-Cl | H | H | OH | O | 2 | |
| 4-Br | H | H | OH | O | 2 | |
| 4-OCF$_2$H | H | H | OH | O | 2 | |
| 4-OCF$_3$ | H | H | OMe | O | 2 | |
| 4-CF$_3$ | H | H | OMe | O | 2 | |
| 4-Cl | H | H | OMe | O | 2 | |
| 4-Br | H | H | O-allyl | O | 2 | |
| 4-OCF$_2$H | H | H | O-allyl | O | 2 | |
| 4-OCF$_3$ | H | H | O-allyl | O | 2 | |
| 4-CF$_3$ | H | H | OAc | O | 2 | |
| 4-Cl | H | H | OAc | O | 2 | |
| 4-Br | H | H | OCONHMe | O | 2 | |
| 4-OCF$_2$H | H | H | OCONMe$_2$ | O | 2 | |
| 4-OCF$_3$ | H | H | OCO$_2$Me | O | 2 | |
| 4-CF$_3$ | H | H | OCO$_2$Me | O | 2 | |
| 4-Cl | H | H | OSO$_2$Me | O | 2 | |
| 4-Br | H | H | OSO$_2$Me | O | 2 | |
| 4-OCF$_2$H | H | H | OCH$_2$Ph | O | 2 | |
| 4-OCF$_3$ | H | H | OCH$_2$Ph | O | 2 | |
| 4-CF$_3$ | H | 5-Cl | H | O | 0 | |
| 4-OCF$_3$ | H | 4-Cl | Me | O | 0 | |

TABLE 1-continued

| $R_1{}^a$ | $R_1{}^b$ | $R_2$ | B | x | t | Phys. Prop. (m.p. °C.) |
|---|---|---|---|---|---|---|
| 4-OCF$_2$H | H | 5-Cl | CO$_2$Me | O | 0 | |
| 4-Cl | H | 5-Cl | CO$_2$CH$_2$CH$_2$Cl | O | 0 | |
| 4-Br | H | 5-Cl | H | O | 1 | 164 to 166 |
| 4-CF$_3$ | H | 5-Cl | Me | O | 1 | |
| 4-OCF$_3$ | H | 5-Cl | Et | O | 1 | |
| 4-Cl | H | 5-Cl | H | O | 1 | 155 to 157 |
| 4-SMe | H | 5-Cl | H | O | 1 | 159 to 161 |
| 4-CO$_2$Et | H | 5-Cl | H | O | 1 | 153 to 156 |
| 4-Br | H | 5-Cl | CO$_2$Me | O | 1 | 234 to 236 |
| 4-SMe | H | 5-Cl | CO$_2$Me | O | 1 | 202 to 204 |
| 4-CO$_2$Et | H | 5-Cl | CO$_2$Me | O | 1 | 197 to 199 |
| 4-OCF$_2$H | H | 5-Cl | CO$_2$Me | O | 1 | |
| 4-Cl | H | 5-Cl | CO$_2$Me | O | 1 | 222 to 233 |
| 4-Br | H | 5-Cl | C(O)Me | O | 1 | |
| 4-CF$_3$ | H | 5-Cl | C(O)Et | O | 1 | |
| 4-OCF$_3$ | H | 5-Cl | C(O)NMe$_2$ | O | 1 | |
| 4-OCF$_2$H | H | 5-Cl | OH | O | 1 | |
| 4-Cl | H | 5-Cl | OAc | O | 1 | |
| 4-Br | H | 5-Cl | H | O | 2 | |
| 4-CF$_3$ | H | 5-Cl | Me | O | 2 | |
| 4-OCF$_3$ | H | 5-Cl | CO$_2$Me | O | 2 | |
| 4-OCF$_2$H | H | 5-Cl | CO$_2$-n-Bu | O | 2 | |
| 4-Cl | H | 5-Cl | CH$_2$Ph | O | 2 | |
| 4-Br | H | 5-Cl | C(O)NHPh | O | 2 | |
| 4-CF$_3$ | H | 5-Cl | OMe | O | 2 | |
| 4-OCF$_3$ | H | 5-Cl | OC(O)NHMe | O | 2 | |
| 4-CF$_3$ | H | 5-F | CO$_2$Me | O | 0 | |
| 4-OCF$_3$ | H | 5-F | CO$_2$Me | O | 0 | |
| 4-OCF$_2$H | H | 5-F | CO$_2$Me | O | 0 | |
| 4-CF$_3$ | H | 5-F | H | O | 1 | 175 to 178 |
| 4-Cl | H | 5-F | H | O | 1 | |
| 4-Br | H | 5-F | H | O | 1 | |
| 4-OCF$_2$H | H | 5-F | H | O | 1 | |
| 4-Cl | H | 5-F | CO$_2$Me | O | 1 | |
| 4-Br | H | 5-F | CO$_2$Me | O | 1 | |
| 4-CF$_3$ | H | 5-F | CO$_2$Me | O | 1 | 223 to 225 |
| 4-OCF$_3$ | H | 5-F | CO$_2$Me | O | 2 | |
| 4-OCF$_2$H | H | 5-F | CO$_2$Me | O | 2 | |
| 4-Cl | H | 5-F | CO$_2$Me | O | 2 | |
| 4-Br | H | 5-OCF$_2$H | CO$_2$Me | O | 0 | |
| 4-CF$_3$ | H | 5-OCF$_2$H | CO$_2$Me | O | 0 | |
| 4-OCF$_3$ | H | 5-OCF$_2$H | CO$_2$Me | O | 0 | |
| 4-OCF$_2$H | H | 5-OCF$_2$H | CO$_2$Me | O | 1 | |
| 4-Cl | H | 5-OCF$_2$H | CO$_2$Me | O | 1 | |
| 4-Br | H | 5-OCF$_2$H | CO$_2$Me | O | 1 | |
| 4-CF$_3$ | H | 5-OCF$_2$H | CO$_2$Me | O | 2 | |
| 4-OCF$_3$ | H | 5-OCF$_2$H | CO$_2$Me | O | 2 | |
| 4-OCF$_2$H | H | 5-OCF$_2$H | CO$_2$Me | O | 2 | |
| 4-Cl | H | 5-Br | CO$_2$Me | O | 1 | |
| 4-Br | H | 5-NO$_2$ | CO$_2$Me | O | 1 | |
| 4-CF$_3$ | H | 5-CF$_3$ | CO$_2$Me | O | 1 | |
| 4-OCF$_3$ | H | 5-OCH$_3$ | CO$_2$Me | O | 1 | |
| 4-CF$_3$ | H | 5-OCH$_2$Ph | Me | O | 1 | |
| 4-CF$_3$ | H | 5-C(O)Me | Et | O | 1 | |
| 4-CF$_3$ | H | 5-OCF$_2$CF$_2$H | CO$_2$Me | O | 1 | |
| 4-CF$_3$ | H | 5-I | Me | O | 1 | |
| 4-CF$_3$ | H | 5-OCF$_3$ | Et | O | 1 | |
| 4-CF$_3$ | H | 5-Et | C(O)Me | O | 1 | |
| 4-CF$_3$ | H | 5-Me | C(O)CF$_3$ | O | 1 | |
| 4-CF$_3$ | H | 5-CN | Me | O | 1 | |
| 4-CF$_3$ | H | 5-OMe | CO$_2$Me | O | 1 | 180 to 186 |
| 4-CF$_3$ | H | 5-OMe | CO$_2$Et | O | 1 | 160 to 166 |
| 4-CF$_3$ | H | 5-OMe | H | O | 1 | 158 to 160 |
| 4-Cl | H | 5-OMe | H | O | 1 | 169 to 171 |
| 4-CF$_3$ | H | 5-CO$_2$Me | n-C$_6$H$_{13}$ | O | 1 | |
| 4-CF$_3$ | H | 5-SCF$_2$H | C(O)H | O | 1 | |
| 4-CF$_3$ | H | 5-SO$_2$Me | (CH$_2$)$_4$Cl | O | 1 | |
| 4-CF$_3$ | H | 5,6-di-Cl | H | O | 1 | 229 to 230 |
| 4-CF$_3$ | H | 5,6-di-Cl | CO$_2$Me | O | 1 | 238 to 241 |
| 4-CF$_3$ | H | 4-F | H | O | 1 | 183 to 184 |
| 4-Cl | H | 4-F | CO$_2$Me | O | 1 | |
| 4-Br | H | 4-F | CO$_2$Me | O | 1 | |
| 4-CF$_3$ | H | 4-Cl | H | O | 1 | 179 to 180 |
| 4-OCF$_2$H | H | 4-Cl | H | O | 1 | |
| 4-OCF$_2$H | H | 4-Cl | CO$_2$Me | O | 1 | |
| 4-CF$_3$ | H | 4-Br | H | O | 1 | |
| 4-CF$_3$ | H | 4-Br | CO$_2$Me | O | 1 | |
| 4-CF$_3$ | H | 6-Cl | CO$_2$Me | O | 1 | |
| 4-CF$_3$ | H | 6-F | CO$_2$Me | O | 1 | |
| 4-CF$_3$ | H | 6-CF$_3$ | CO$_2$Me | O | 1 | |

TABLE 1-continued

| $R_1{}^a$ | $R_1{}^b$ | $R_2$ | B | x | t | Phys. Prop. (m.p. °C.) |
|---|---|---|---|---|---|---|
| 4-CF$_3$ | H | 4-Cl | CO$_2$Me | O | 1 | |
| 4-CF$_3$ | H | 4-F | CO$_2$Me | O | 1 | 206 to 212 |
| 4-CF$_3$ | H | 6-Br | CO$_2$Me | O | 1 | |
| 4-CF$_3$ | H | 6-NO$_2$ | CO$_2$Me | O | 1 | |
| 4-CF$_3$ | H | 6-Me | CO$_2$Me | O | 1 | |
| 4-CF$_3$ | H | 4-Cl | CO$_2$Me | O | 1 | 209 to 211 |
| 4-CF$_3$ | H | 4-F | CO$_2$Me | O | 1 | |
| 4-CF$_3$ | H | 4-Br | CO$_2$Me | O | 1 | |
| 4-CF$_3$ | H | H | H | S | 0 | |
| 4-Cl | H | H | Me | S | 0 | |
| 4-CF$_3$ | H | H | CO$_2$Me | S | 0 | |
| 4-Cl | H | H | H | S | 1 | |
| 4-CF$_3$ | H | H | Me | S | 1 | |
| 4-Cl | H | H | CO$_2$Me | S | 1 | |
| 4-CF$_3$ | H | H | H | S | 2 | |
| 4-Cl | H | H | Me | S | 2 | |
| 4-CF$_3$ | H | H | CO$_2$Me | S | 2 | |
| 4-Cl | H | 5-Cl | H | S | 1 | |
| 4-CF$_3$ | H | 5-Cl | Me | S | 1 | |
| 4-Cl | H | 5-Cl | CO$_2$Me | S | 1 | |
| 4-CF$_3$ | H | 5-F | H | S | 1 | |
| 4-Cl | H | 5-F | Me | S | 1 | |
| 4-CF$_3$ | H | 5-F | CO$_2$Me | S | 1 | |

*as a representative example this substitution pattern designates

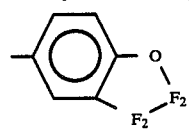

TABLE 2

| $R_1{}^a$ | $R_1{}^b$ | $R_2$ | B | x | t | v | Phys. Prop. (m.p. °C.) |
|---|---|---|---|---|---|---|---|
| 4-CF$_3$ | H | H | H | O | 0 | O | |
| 4-CF$_2$Cl | 3-Cl | H | H | O | 1 | O | |
| 4-CF$_3$ | H | H | H | O | 1 | O | 161 to 164 |
| 4-Cl | 3-Cl | H | H | O | 1 | O | 220 to 224 |
| 4-Br | H | H | H | O | 1 | O | 215 to 220 |
| 3-CF$_3$ | H | H | H | O | 1 | O | 165 to 167 |
| 4-Cl | H | H | H | O | 1 | O | 192 to 199 |
| 3-Cl | H | H | H | O | 1 | O | 162 to 171 |
| 4-CF$_3$ | H | 5-Br | H | O | 1 | O | 192 to 195 |
| 4-Cl | H | 5-Br | H | O | 1 | O | 144 to 150 |
| 4-Br | H | 5-Br | H | O | 1 | O | 218 to 221 |
| 4-Cl | H | 7-Br | H | O | 1 | O | 180 to 184 |
| 4-CF$_3$ | H | 7-Br | H | O | 1 | O | 161 to 182 |
| 4-Br | H | 7-Br | H | O | 1 | O | 179 to 202 |
| 4-CF$_3$ | H | 5-Cl | H | O | 1 | O | 152 to 182 |
| 4-Cl | H | 5-Cl | H | O | 1 | O | 193 to 207 |
| 4-Cl | H | 5-F | H | O | 1 | O | |
| 4-CO$_2$Me | H | 5-F | H | O | 2 | O | |
| 4-Br | H | 5-Cl | H | O | 1 | O | 228 to 232 |
| 4-CF$_3$ | H | 7-Cl | H | O | 1 | O | 178 to 202 |
| 4-Cl | H | 7-Cl | H | O | 1 | O | 179 to 193 |
| 4-Br | H | 7-Cl | H | O | 1 | O | 201 to 208 |
| 4-CF$_3$ | H | H | Me | O | 1 | O | |
| 4-CF$_2$Cl | 3-Cl | 5-Cl | Me | O | 2 | O | |
| 4-OCF$_3$ | H | 5-Cl | Me | O | 0 | O | |
| 4-OCF$_2$H | H | 5-F | Me | O | 1 | O | |
| 4-Cl | H | 5-F | Me | O | 2 | O | |
| 4-CO$_2$Me | H | H | Me | O | 0 | O | |
| 4-Br | H | H | Me | O | 1 | O | |
| 4-CF$_3$ | H | 5-Cl | CO$_2$Me | O | 2 | O | |
| 4-CF$_2$Cl | 3-Cl | 5-Cl | CO$_2$Me | O | 0 | O | |
| 4-OCF$_3$ | H | H | CO$_2$Me | O | 1 | O | |
| 4-OCF$_2$H | H | H | CO$_2$Me | O | 2 | O | |
| 4-Cl | H | 5-Cl | CO$_2$Me | O | 0 | O | |
| 4-CO$_2$Me | H | 5-Cl | CO$_2$Me | O | 1 | O | |
| 4-Br | H | 5-F | CO$_2$Me | O | 2 | O | |
| 4-CF$_3$ | H | H | CO$_2$Et | O | 0 | O | |
| 4-Cl | H | H | CO$_2$CH$_2$CF$_3$ | O | 1 | O | |
| 4-CF$_3$ | H | 5-Cl | CH$_2$CF$_3$ | O | 2 | O | |
| 4-Cl | H | 5-Cl | C(O)Me | O | 0 | O | |
| 4-CF$_3$ | H | 5-OCF$_2$H | Me | O | 1 | O | |
| 4-CF$_3$ | H | 5-OCF$_2$H | CO$_2$Me | O | 2 | O | |
| 4-Cl | H | 5-F | CONHMe | O | 0 | O | |

TABLE 2-continued

| $R_1{}^a$ | $R_1{}^b$ | $R_2$ | B | x | t | v | Phys. Prop. (m.p. °C.) |
|---|---|---|---|---|---|---|---|
| 4-CF$_3$ | H | 5-F | CONHPh | O | 1 | O | |
| 4-Cl | H | H | allyl | O | 2 | O | |
| 4-CF$_3$ | H | H | CH$_2$Ph | O | 0 | O | |
| 4-Cl | H | 5-Cl | n-Pr | O | 1 | O | |
| 4-CF$_3$ | H | 5-Cl | C(O)(CH$_2$)$_3$Cl | O | 2 | O | |
| 4-Cl | H | 5-OCF$_2$H | Me | O | 0 | O | |
| 4-CF$_3$ | H | 5-OCF$_2$H | CO$_2$Me | O | 1 | O | |
| 4-Cl | H | 5-F | CH$_2$CO$_2$Me | O | 2 | O | |
| 4-CF$_3$ | H | 5-F | CO$_2$H | O | 0 | O | |
| 4-Cl | H | H | 4-Cl-Ph | O | 1 | O | |
| 4-CF$_3$ | H | H | 4-Cl-Ph | O | 2 | O | |
| 4-Cl | H | 5-Cl | CO$_2$Me | S | 0 | O | |
| 4-CF$_3$ | H | 5-Cl | CO$_2$Me | S | 1 | O | |
| 4-Cl | H | 5-OCF$_2$H | CO$_2$Me | S | 2 | O | |
| 4-CF$_3$ | H | H | H | O | 0 | S | |
| 4-CF$_2$Cl | 3-Cl | H | H | O | 1 | S | |
| 4-OCF$_3$ | H | 5-Cl | H | O | 2 | S | |
| 4-OCF$_2$H | H | 5-Cl | H | O | 0 | S | |
| 4-Cl | H | 5-F | H | O | 1 | S | |
| 4-CO$_2$Me | H | 5-F | H | O | 2 | S | |
| 4-Br | H | H | H | O | 0 | S | |
| 4-CF$_3$ | H | H | H | O | 1 | S | 170 to 171 |
| 4-Cl | 3-Cl | H | H | O | 1 | S | 235 to 239 |
| 4-Br | H | H | H | O | 1 | S | 189 to 192 |
| 3-CF$_3$ | H | H | H | O | 1 | S | 203 to 204 |
| 4-Cl | H | H | H | O | 1 | S | 178 to 180 |
| 3-CF$_3$ | H | 5-Cl | H | O | 1 | S | 197 to 200 |
| 4-Cl | H | 5-Cl | H | O | 1 | S | 202 to 206 |
| 3-Cl | H | 5-Cl | H | O | 1 | S | 224 to 227 |
| 4-Br | H | 5-Cl | H | O | 1 | S | 207 to 211 |
| 4-Cl | 3-Cl | 5-Cl | H | O | 1 | S | 220 to 232 |
| 4-CF$_3$ | H | 6-Cl | H | O | 1 | S | 195 to 202 |
| 3-CF$_3$ | H | 6-Cl | H | O | 1 | S | 207 to 213 |
| 4-Cl | H | 6-Cl | H | O | 1 | S | 180 to 188 |
| 3-Cl | H | 6-Cl | H | O | 1 | S | 230 to 240 |
| 4-Br | H | 6-Cl | H | O | 1 | S | 184 to 189 |
| 4-Cl | 3-Cl | 6-Cl | H | O | 1 | S | 227 to 237 |
| 4-CF$_3$ | H | 5-Br | H | O | 1 | S | 212 to 215 |
| 3-CF$_3$ | H | 5-Br | H | O | 1 | S | 187 to 200 |
| 4-Cl | H | 5-Br | H | O | 1 | S | 192 to 209 |
| 3-Cl | H | 5-Br | H | O | 1 | S | 175 to 190 |
| 4-Br | H | 5-Br | H | O | 1 | S | 188 to 215 |
| 4-Cl | 3-Cl | 5-Br | H | O | 1 | S | 187 to 200 |
| 4-CF$_3$ | H | 4-Cl | H | O | 1 | S | 207 to 210 |
| 4-Cl | H | 4-Cl | H | O | 1 | S | 191 to 193 |
| 4-Br | H | 4-Cl | H | O | 1 | S | 188 to 190 |
| 4-CF$_3$ | H | H | Me | O | 1 | S | |
| 4-CF$_2$Cl | 3-Cl | 5-Cl | Me | O | 2 | S | |
| 4-OCF$_3$ | H | 5-Cl | Me | O | 0 | S | |
| 4-OCF$_2$H | H | 5-F | Me | O | 1 | S | |
| 4-Cl | H | 5-F | Me | O | 2 | S | |
| 4-CO$_2$Me | H | H | Me | O | 0 | S | |
| 4-Br | H | H | Me | O | 1 | S | |
| 4-CF$_3$ | H | 5-Cl | CO$_2$Me | O | 2 | S | |
| 4-CF$_2$Cl | 3-Cl | 5-Cl | CO$_2$Me | O | 0 | S | |
| 4-OCF$_3$ | H | H | CO Me | O | 1 | S | |
| 4-OCF$_2$H | H | H | CO$_2$Me | O | 2 | S | |
| 4-Cl | H | 5-Cl | CO$_2$Me | O | 0 | S | |
| 4-CO$_2$Me | H | 5-Cl | CO$_2$Me | O | 1 | S | |
| 4-Br | H | 5-F | CO$_2$Me | O | 2 | S | |
| 4-CF$_3$ | H | H | CO$_2$Et | O | 0 | S | |
| 4-Cl | H | H | CO$_2$CH$_2$CF$_3$ | O | 1 | S | |
| 4-CF$_3$ | H | 5-Cl | CH$_2$CF$_3$ | O | 2 | S | |
| 4-Cl | H | 5-Cl | C(O)Me | O | 0 | S | |
| 4-CF$_3$ | H | 5-OCF$_2$H | Me | O | 1 | S | |
| 4-CF$_3$ | H | 5-OCF$_2$H | CO$_2$Me | O | 2 | S | |
| 4-Cl | H | 5-F | CONHMe | O | 0 | S | |
| 4-CF$_3$ | H | 5-F | CONHPh | O | 1 | S | |
| 4-Cl | H | H | allyl | O | 2 | S | |
| 4-CF$_3$ | H | H | CH$_2$Ph | O | 0 | S | |
| 4-Cl | H | 5-Cl | n-Pr | O | 1 | S | |
| 4-CF$_3$ | H | 5-Cl | C(O)(CH$_2$)$_3$Cl | O | 2 | S | |
| 4-Cl | H | 5-OCF$_2$H | Me | O | 0 | S | |
| 4-CF$_3$ | H | 5-OCF$_2$H | CO$_2$Me | O | 1 | S | |
| 4-Cl | H | 5-F | CH$_2$CO$_2$Me | O | 2 | S | |
| 4-CF$_3$ | H | 5-F | CO$_2$H | O | 0 | S | |
| 4-Cl | H | H | 4-Cl-Ph | O | 1 | S | |
| 4-CF$_3$ | H | H | 4-Cl-Ph | O | 2 | S | |
| 4-Cl | H | 5-Cl | CO$_2$Me | S | 0 | S | |
| 4-CF$_3$ | H | 5-Cl | CO$_2$Me | S | 1 | S | |

TABLE 2-continued

| $R_1{}^a$ | $R_1{}^b$ | $R_2$ | B | x | t | v | Phys. Prop. (m.p. °C.) |
|---|---|---|---|---|---|---|---|
| 4-Cl | H | 5-OCF$_2$H | CO$_2$Me | S | 2 | S | |
| 4-CF$_3$ | H | H | H | O | 0 | NMe | |
| 4-CF$_2$Cl | 3-Cl | H | H | O | 1 | NMe | |
| 4-OCF$_3$ | H | 5-Cl | H | O | 2 | NMe | |
| 4-OCF$_2$H | H | 5-Cl | H | O | 0 | NMe | |
| 4-Cl | H | 5-F | H | O | 1 | NMe | |
| 4-CO$_2$Me | H | 5-F | H | O | 2 | NMe | |
| 4-Br | H | H | H | O | 0 | NMe | |
| 4-CF$_3$ | H | H | Me | O | 1 | NMe | |
| 4-CF$_2$Cl | 3-Cl | 5-Cl | Me | O | 2 | NMe | |
| 4-OCF$_3$ | H | 5-Cl | Me | O | 0 | NMe | |
| 4-OCF$_2$H | H | 5-F | Me | O | 1 | NMe | |
| 4-Cl | H | 5-F | Me | O | 2 | NMe | |
| 4-CO$_2$Me | H | H | Me | O | 0 | NMe | |
| 4-Br | H | H | Me | O | 1 | NMe | |
| 4-CF$_3$ | H | 5-Cl | CO$_2$Me | O | 2 | NMe | |
| 4-CF$_2$Cl | 3-Cl | 5-Cl | CO$_2$Me | O | 0 | NMe | |
| 4-OCF$_3$ | H | H | CO$_2$Me | O | 1 | NMe | |
| 4-OCF$_2$H | H | H | CO$_2$Me | O | 2 | NMe | |
| 4-Cl | H | 5-Cl | CO$_2$Me | O | 0 | NMe | |
| 4-CO$_2$Me | H | 5-Cl | CO$_2$Me | O | 1 | NMe | |
| 4-Br | H | 5-F | CO$_2$Me | O | 2 | NMe | |
| 4-CF$_3$ | H | H | CO$_2$Et | O | 0 | NMe | |
| 4-Cl | H | H | CO$_2$CH$_2$CF$_3$ | O | 1 | NME | |
| 4-CF$_3$ | H | 5-Cl | CH$_2$CF$_3$ | O | 2 | NMe | |
| 4-Cl | H | 5-Cl | C(O)Me | O | 0 | NMe | |
| 4-CF$_3$ | H | 5-OCF$_2$H | Me | O | 1 | NMe | |
| 4-CF$_3$ | H | 5-OCF$_2$H | CO$_2$Me | O | 2 | NMe | |
| 4-Cl | H | 5-F | CONHMe | O | 0 | NMe | |
| 4-CF$_3$ | H | 5-F | CONHPh | O | 1 | NMe | |
| 4-Cl | H | H | allyl | O | 2 | NMe | |
| 4-CF$_3$ | H | H | CH$_2$Ph | O | 0 | NMe | |
| 4-Cl | H | 5-Cl | n-Pr | O | 1 | NMe | |
| 4-CF$_3$ | H | 5-Cl | C(O)(CH$_2$)$_3$Cl | O | 2 | NMe | |
| 4-Cl | H | 5-OCF$_2$H | Me | O | 0 | NMe | |
| 4-CF$_3$ | H | 5-OCF$_2$H | CO$_2$Me | O | 1 | NMe | |
| 4-Cl | H | 5-F | CH$_2$CO$_2$Me | O | 2 | NMe | |
| 4-CF$_3$ | H | 5-F | CO$_2$H | O | 0 | NMe | |
| 4-Cl | H | H | 4-Cl-Ph | O | 1 | NMe | |
| 4-CF$_3$ | H | H | 4-Cl-Ph | O | 2 | NMe | |
| 4-Cl | H | 5-Cl | CO$_2$Me | S | 0 | NMe | |
| 4-CF$_3$ | H | 5-Cl | CO$_2$Me | S | 1 | NMe | |
| 4-Cl | H | 5-OCF$_2$H | CO$_2$Me | S | 2 | NMe | |
| 4-CF$_3$ | H | H | H | O | 1 | SO$_2$ | 255 to 260 |
| 4-Cl | 3-Cl | H | H | O | 1 | SO$_2$ | 250 to 255 |
| 4-Br | H | H | H | O | 1 | SO$_2$ | 272 to 274 |
| 3-CF$_3$ | H | H | H | O | 1 | SO$_2$ | 261 to 263 |
| 4-Cl | H | H | H | O | 1 | SO$_2$ | 247 to 250 |
| 3-Cl | H | H | H | O | 1 | SO$_2$ | 245 to 249 |
| 4-CF$_3$ | H | 5-Cl | H | O | 1 | SO$_2$ | 293 to 297 |
| 3-CF$_3$ | H | 5-Cl | H | O | 1 | SO$_2$ | 217 to 234 |
| 4-Cl | H | 5-Cl | H | O | 1 | SO$_2$ | 318 to 321 |
| 3-Cl | H | 5-Cl | H | O | 1 | SO$_2$ | 241 to 270 |
| 4-Br | H | 5-Cl | H | O | 1 | SO$_2$ | 290 to 292 |
| 4-Cl | 3-Cl | 5-Cl | H | O | 1 | SO$_2$ | 280 to 285 |
| 4-CF$_3$ | H | 6-Cl | H | O | 1 | SO$_2$ | 290 to 292 |
| 3-CF$_3$ | H | 6-Cl | H | O | 1 | SO$_2$ | 175 to 182 |
| 4-Cl | H | 6-Cl | H | O | 1 | SO$_2$ | 230 to 280 |
| 3-Cl | H | 6-Cl | H | O | 1 | SO$_2$ | 245 to 269 |
| 4-Br | H | 6-Cl | H | O | 1 | SO$_2$ | 307 to 310 |
| 4-Cl | 3-Cl | 6-Cl | H | O | 1 | SO$_2$ | 275 to 278 |
| 4-CF$_3$ | H | H | Me | O | 0 | SO$_2$ | |
| 4-Cl | H | 5-Cl | Me | O | 1 | SO$_2$ | |
| 4-OCF$_3$ | H | H | Me | O | 2 | SO$_2$ | |
| 4-CF$_3$ | H | 5-Cl | CO$_2$Me | O | 0 | SO$_2$ | |
| 4-Cl | H | H | CO$_2$Me | O | 1 | SO$_2$ | |
| 4-OCF$_3$ | H | 5-Cl | CO$_2$Me | O | 2 | SO$_2$ | |
| 3-CF$_3$ | H | H | H | O | 1 | SO($\alpha$) | 255 to 260 |
| 4-CF$_3$ | H | H | H | O | 1 | SO($\alpha$) | 250 to 255 |
| 4-Br | H | H | H | O | 1 | SO($\alpha$) | 278 to 282 |
| 4-Br | H | H | H | O | 1 | SO($\beta$) | 258 to 260 |
| 4-Cl | 3-Cl | H | H | O | 1 | SO($\alpha$) | 275 to 280 |
| 4-Cl | 3-Cl | H | H | O | 1 | SO($\beta$) | 265 to 269 |
| 4-Cl | H | H | H | O | 1 | SO($\alpha$) | 262 to 264 |
| 4-Cl | H | H | H | O | 1 | SO($\beta$) | 247 to 250 |
| 3-Cl | H | H | H | O | 1 | SO($\alpha$) | 231 to 232 |
| 3-Cl | H | H | H | O | 1 | SO($\beta$) | 255 to 258 |
| 4-CF$_3$ | H | 5-Cl | H | O | 1 | SO($\alpha$) | 271 to 275 |
| 4-CF$_3$ | H | 5-Cl | H | O | 1 | SO($\beta$) | 256 to 277 |
| 3-CF$_3$ | H | 5-Cl | H | O | 1 | SO($\alpha$) | 210 to 213 |

TABLE 2-continued

| R$_1^a$ | R$_1^b$ | R$_2$ | B | x | t | v | Phys. Prop. (m.p. °C.) |
|---|---|---|---|---|---|---|---|
| 3-CF$_3$ | H | 5-Cl | H | O | 1 | SO($\beta$) | 250 to 252 |
| 4-Cl | H | 5-Cl | H | O | 1 | SO($\alpha$) | 284 to 286 |
| 4-Cl | H | 5-Cl | H | O | 1 | SO($\beta$) | 278 to 283 |
| 3-Cl | H | 5-Cl | H | O | 1 | SO($\alpha$) | 240 to 241 |
| 3-Cl | H | 5-Cl | H | O | 1 | SO($\beta$) | 230 to 246 |
| 4-Br | H | 5-Cl | H | O | 1 | SO($\alpha$) | 285 to 287 |
| 4-Br | H | 5-Cl | H | O | 1 | SO($\beta$) | 267 to 272 |
| 4-Cl | 3-Cl | 5-Cl | H | O | 1 | SO($\alpha$) | 276 to 280 |
| 4-Cl | 3-Cl | 5-Cl | H | O | 1 | SO($\beta$) | 254 to 268 |
| 4-CF$_3$ | H | 6-Cl | H | O | 1 | SO($\alpha$) | 252 to 256 |
| 4-CF$_3$ | H | 6-Cl | H | O | 1 | SO($\beta$) | 218 to 232 |
| 3-CF$_3$ | H | 6-Cl | H | O | 1 | SO($\alpha$) | 263 to 265 |
| 3-CF$_3$ | H | 6-Cl | H | O | 1 | SO($\beta$) | |
| 4-Cl | H | 6-Cl | H | O | 1 | SO($\alpha$) | 243 to 245 |
| 4-Cl | H | 6-Cl | H | O | 1 | SO($\beta$) | 269 to 272 |
| 3-Cl | H | 6-Cl | H | O | 1 | SO($\alpha$) | 154 to 160 |
| 3-Cl | H | 6-Cl | H | O | 1 | SO($\beta$) | |
| 4-Br | H | 6-Cl | H | O | 1 | SO($\alpha$) | 248 to 250 |
| 4-Br | H | 6-Cl | H | O | 1 | SO($\beta$) | 283 to 285 |
| 4-Cl | 3-Cl | 6-Cl | H | O | 1 | SO($\alpha$) | 272 to 275 |
| 4-Cl | 3-Cl | 6-Cl | H | O | 1 | SO($\beta$) | 289 to 295 |
| 3-CF$_3$ | H | H | H | O | 1 | SO($\beta$) | 229 to 236 |
| 4-CF$_3$ | H | H | H | O | 1 | SO($\beta$) | 235 to 258 |
| 4-OCF$_3$ | H | H | Me | O | 0 | N-n-Bu | |
| 4-CF$_3$ | H | 5-Cl | CO$_2$Me | O | 1 | N-allyl | |
| 4-Cl | H | H | CO$_2$Me | O | 0 | N-Ph | |
| 4-OCF$_3$ | H | 5-Cl | CO$_2$Me | O | 1 | N—CH$_2$Ph | |
| 4-CF$_3$ | H | H | CO$_2$Me | O | 0 | N-4-F-Ph | |
| 4-CF$_3$ | H | H | H | O | 1 | NH | |
| 4-CF$_3$ | H | H | CO$_2$Me | O | 1 | NH | |
| 4-CF$_3$ | H | 5-Cl | H | O | 1 | NMe | |
| 4-CF$_3$ | H | 5-Cl | CO$_2$Me | O | 1 | NMe | |

TABLE 3

| R$_1^a$ | R$_1^b$ | R$_2$ | B | x | t | v | Phys. Prop. (m.p. °C.) |
|---|---|---|---|---|---|---|---|
| 4-CF$_3$ | H | H | H | O | 0 | O | |
| 4-CF$_2$Cl | 3-Cl | H | H | O | 1 | O | |
| 4-OCF$_3$ | H | 5-Cl | H | O | 2 | O | |
| 4-OCF$_2$H | H | 5-Cl | H | O | 2 | O | |
| 4-Cl | H | 5-F | H | O | 1 | O | |
| 4-CO$_2$Me | H | 5-F | H | O | 2 | O | |
| 4-Br | H | H | H | O | 0 | O | |
| 4-CF$_3$ | H | H | Me | O | 1 | O | |
| 4-CF$_2$Cl | 3-Cl | 5-Cl | Me | O | 2 | O | |
| 4-OCF$_3$ | H | 5-Cl | Me | O | 0 | O | |
| 4-OCF$_2$H | H | 5-F | Me | O | 1 | O | |
| 4-Cl | H | 5-F | Me | O | 2 | O | |
| 4-CO$_2$Me | H | H | Me | O | 0 | O | |
| 4-Br | H | H | Me | O | 1 | O | |
| 4-CF$_3$ | H | 5-Cl | CO$_2$Me | O | 2 | O | |
| 4-CF$_2$Cl | 3-Cl | 5-Cl | CO$_2$Me | O | 0 | O | |
| 4-OCF$_3$ | H | H | CO$_2$Me | O | 1 | O | |
| 4-OCF$_2$H | H | H | CO$_2$Me | O | 2 | O | |
| 4-Cl | H | 5-Cl | CO$_2$Me | O | 0 | O | |
| 4-CO$_2$Me | H | 5-CL | CO$_2$Me | O | 1 | O | |
| 4-Br | H | 5-F | CO$_2$Me | O | 2 | O | |
| 4-CF$_3$ | H | H | CO$_2$Et | O | 0 | O | |
| 4-Cl | H | H | CO$_2$CH$_2$CF$_3$ | O | 1 | O | |
| 4-CF$_3$ | H | 5-CL | CH$_2$CF$_3$ | O | 2 | O | |
| 4-Cl | H | 5-Cl | C(O)Me | O | 0 | O | |
| 4-CF$_3$ | H | 5-OCF$_2$H | Me | O | 1 | O | |
| 4-CF$_3$ | H | 5-OCF$_2$H | CO$_2$Me | O | 2 | O | |
| 4-Cl | H | 5-F | CONHMe | O | 0 | O | |
| 4-CF$_3$ | H | 5-F | CONHPh | O | 1 | O | |
| 4-Cl | H | H | allyl | O | 2 | O | |
| 4-CF$_3$ | H | H | CH$_2$Ph | O | 0 | O | |
| 4-Cl | H | 5-Cl | n-Pr | O | 1 | O | |
| 4-CF$_3$ | H | 5-Cl | C(O)(CH$_2$)$_3$Cl | O | 2 | O | |
| 4-Cl | H | 5-OCF$_2$H | CO$_2$Me | O | 1 | O | |
| 4-Cl | H | 5-F | CH$_2$CO$_2$Me | O | 2 | O | |
| 4-CF$_3$ | H | 5-F | CO$_2$H | O | 0 | O | |
| 4-Cl | H | H | 4-Cl-Ph | O | 1 | O | |
| 4-CF$_3$ | H | H | 4-Cl-Ph | O | 2 | O | |
| 4-Cl | H | 5-Cl | CO$_2$Me | S | 0 | O | |
| 4-CF$_3$ | H | 5-Cl | CO$_2$Me | S | 1 | O | |
| 4-Cl | H | 5-OCF$_2$H | CO$_2$Me | S | 2 | O | |

TABLE 3-continued

| $R_1{}^a$ | $R_1{}^b$ | $R_2$ | B | x | t | v | Phys. Prop. (m.p. °C.) |
|---|---|---|---|---|---|---|---|
| 4-CF$_3$ | H | H | H | O | 0 | S | |
| 4-CF$_2$Cl | 3-Cl | H | H | O | 1 | S | |
| 4-OCF$_3$ | H | 5-Cl | H | O | 2 | S | |
| 4-OCF$_2$H | H | 5-Cl | H | O | 2 | S | |
| 4-Cl | H | 5-F | H | O | 1 | S | |
| 4-CO$_2$Me | H | 5-F | H | O | 2 | S | |
| 4-Br | H | H | H | O | 0 | S | |
| 4-CF$_3$ | H | H | Me | O | 1 | S | |
| 4-CF$_2$Cl | 3-Cl | 5-Cl | Me | O | 2 | S | |
| 4-OCF$_3$ | H | 5-Cl | Me | O | 0 | S | |
| 4-OCF$_2$H | H | 5-F | Me | O | 1 | S | |
| 4-Cl | H | 5-F | Me | O | 2 | S | |
| 4-CO$_2$Me | H | H | Me | O | 0 | S | |
| 4-Br | H | H | Me | O | 1 | S | |
| 4-CF$_3$ | H | 5-Cl | CO$_2$Me | O | 2 | S | |
| 4-CF$_2$Cl | 3-Cl | 5-Cl | CO$_2$Me | O | 0 | S | |
| 4-OCF$_3$ | H | H | CO$_2$Me | O | 1 | S | |
| 4-OCF$_2$H | H | H | CO$_2$Me | O | 2 | S | |
| 4-Cl | H | 5-Cl | CO$_2$Me | O | 0 | S | |
| 4-CO$_2$Me | H | 5-Cl | CO$_2$Me | O | 1 | S | |
| 4-Br | H | 5-F | CO$_2$Me | 0 | 2 | S | |
| 4-CF$_3$ | H | H | CO$_2$Et | O | 0 | S | |
| 4-Cl | H | H | CO$_2$CH$_2$CF$_3$ | O | 1 | S | |
| 4-CF$_3$ | H | 5-Cl | CH$_2$CF$_3$ | O | 2 | S | |
| 4-Cl | H | 5-Cl | C(O)Me | O | 0 | S | |
| 4-CF$_3$ | H | 5-OCF$_2$H | Me | O | 1 | S | |
| 4-CF$_3$ | H | 5-OCF$_2$H | CO$_2$Me | O | 2 | S | |
| 4-Cl | H | 5-F | CONHMe | O | 0 | S | |
| 4-CF$_3$ | H | 5-F | CONHPh | O | 1 | S | |
| 4-Cl | H | H | allyl | O | 2 | S | |
| 4-CF$_3$ | H | H | CH$_2$Ph | O | 0 | S | |
| 4-Cl | H | 5-Cl | n-Pr | O | 1 | S | |
| 4-CF$_3$ | H | 5-Cl | C(O)(CH$_2$)$_3$Cl | O | 2 | S | |
| 4-Cl | H | 5-OCF$_2$H | CO$_2$Me | O | 1 | S | |
| 4-Cl | H | 5-F | CH$_2$CO$_2$Me | O | 2 | S | |
| 4-CF$_3$ | H | 5-F | CO$_2$H | O | 0 | S | |
| 4-Cl | H | H | 4-Cl-Ph | O | 1 | S | |
| 4-CF$_3$ | H | H | 4-Cl-Ph | O | 2 | S | |
| 4-Cl | H | 5-Cl | CO$_2$Me | S | 0 | S | |
| 4-CF$_3$ | H | 5-Cl | CO$_2$Me | S | 1 | S | |
| 4-Cl | H | 5-OCF$_2$H | CO$_2$Me | S | 2 | S | |
| 4-CF$_3$ | H | H | H | O | 0 | NMe | |
| 4-CF$_2$Cl | 3-Cl | H | H | O | 1 | NMe | |
| 4-OCF$_3$ | H | 5-Cl | H | O | 2 | NMe | |
| 4-OCF$_2$H | H | 5-Cl | H | O | 2 | NMe | |
| 4-Cl | H | 5-F | H | O | 1 | NMe | |
| 4-CO$_2$Me | H | 5-F | H | O | 2 | NMe | |
| 4-Br | H | H | H | O | 0 | NMe | |
| 4-CF$_3$ | 3-Cl | 5-Cl | Me | O | 1 | NMe | |
| 4-CF$_2$Cl | 3-Cl | 5-Cl | Me | O | 2 | NMe | |
| 4-OCF$_3$ | H | 5-Cl | Me | O | 0 | NMe | |
| 4-OCF$_2$H | H | 5-F | Me | O | 1 | NMe | |
| 4-Cl | H | 5-F | Me | O | 2 | NMe | |
| 4-CO$_2$Me | H | H | Me | O | 0 | NMe | |
| 4-Br | H | H | Me | O | 1 | NMe | |
| 4-CF$_3$ | H | 5-Cl | CO$_2$Me | O | 2 | NMe | |
| 4-CF$_2$Cl | 3-Cl | 5-Cl | CO$_2$Me | O | 0 | NMe | |
| 4-OCF$_3$ | H | H | CO$_2$Me | O | 1 | NMe | |
| 4-OCF$_2$H | H | H | CO$_2$Me | O | 2 | NMe | |
| 4-Cl | H | 5-Cl | CO$_2$Me | O | 0 | NMe | |
| 4-CO$_2$Me | H | 5-Cl | CO$_2$Me | O | 1 | NMe | |
| 4-Br | H | 5-F | CO$_2$Me | O | 2 | NMe | |
| 4-CF$_3$ | H | H | CO$_2$Et | O | 0 | NMe | |
| 4-Cl | H | H | CO$_2$CH$_2$CF$_3$ | O | 1 | NMe | |
| 4-CF$_3$ | H | 5-Cl | CH$_2$CF$_3$ | O | 2 | NMe | |
| 4-Cl | H | 5-Cl | C(O)Me | O | 0 | NMe | |
| 4-CF$_3$ | H | 5-OCF$_2$H | Me | O | 1 | NMe | |
| 4-CF$_3$ | H | 5-OCF$_2$H | CO$_2$Me | O | 2 | NMe | |
| 4-Cl | H | 5-F | CONHMe | O | 0 | NMe | |
| 4-CF$_3$ | H | 5-F | CONHPh | O | 1 | NMe | |
| 4-Cl | H | H | allyl | O | 2 | NMe | |
| 4-CF$_3$ | H | H | CH$_2$Ph | O | 0 | NMe | |
| 4-Cl | H | 5-Cl | N—Pr | O | 1 | NMe | |
| 4-CF$_3$ | H | 5-Cl | C(O)(CH$_2$)$_3$Cl | O | 2 | NMe | |
| 4-Cl | H | 5-OCF$_2$H | CO$_2$Me | O | 1 | NMe | |
| 4-Cl | H | 5-F | CH$_2$CO$_2$Me | O | 2 | NMe | |
| 4-CF$_3$ | H | 5-F | CO$_2$H | O | 0 | NMe | |
| 4-Cl | H | H | 4-Cl-Ph | O | 1 | NMe | |
| 4-CF$_3$ | H | H | 4-Cl-Ph | O | 2 | NMe | |
| 4-Cl | H | 5-Cl | CO$_2$Me | S | 0 | NMe | |

TABLE 3-continued

| $R_1{}^a$ | $R_1{}^b$ | $R_2$ | B | x | t | v | Phys. Prop. (m.p. °C.) |
|---|---|---|---|---|---|---|---|
| 4-CF$_3$ | H | 5-Cl | CO$_2$Me | S | 1 | NMe | |
| 4-Cl | H | 5-OCF$_2$H | CO$_2$Me | S | 2 | NMe | |
| 4-CF$_3$ | H | H | Me | O | 0 | SO$_2$ | |
| 4-Cl | H | 5-Cl | Me | O | 1 | SO$_2$ | |
| 4-OCF$_3$ | H | H | Me | O | 2 | SO$_2$ | |
| 4-CF$_3$ | H | 5-Cl | CO$_2$Me | O | 0 | SO$_2$ | |
| 4-Cl | H | H | CO$_2$Me | O | 1 | SO$_2$ | |
| 4-OCF$_3$ | H | 5-Cl | CO$_2$Me | O | 2 | SO$_2$ | |
| 4-CF$_3$ | H | H | Me | O | 0 | SO | |
| 4-Cl | H | 5-Cl | Me | O | 1 | SO | |
| 4-OCF$_3$ | H | H | Me | O | 2 | SO | |
| 4-CF$_3$ | H | 5-Cl | CO$_2$Me | O | 0 | SO | |
| 4-Cl | H | H | CO$_2$Me | O | 1 | SO | |
| 4-OCF$_3$ | H | 5-Cl | CO$_2$Me | O | 2 | SO | |
| 4-CF$_3$ | H | H | Me | O | 0 | SO | |
| 4-Cl | H | 5-Cl | Me | O | 1 | NH | |
| 4-OCF$_3$ | H | H | Me | O | 0 | N-n-Bu | |
| 4-CF$_3$ | H | 5-Cl | CO$_2$Me | O | 1 | N-allyl | |
| 4-Cl | H | H | CO$_2$Me | O | 0 | N-Ph | |
| 4-OCH$_3$ | H | 5-Cl | CO$_2$Me | O | 1 | N—CH$_2$Ph | |
| 4-CF$_3$ | H | H | CO$_2$Me | O | 0 | N-4-F-Ph | |

TABLE 4

| $R_1{}^a$ | $R_1{}^b$ | $R_2$ | B | x | z | Phys. Prop. (m.p. °C.) |
|---|---|---|---|---|---|---|
| 4-CF$_3$ | H | H | H | O | O | |
| 4-Cl | H | H | H | O | O | |
| 4-F | H | 5-Cl | H | O | O | |
| 4-OCF$_2$H | H | 5-Cl | Me | O | O | |
| 4-SMe | H | H | Me | O | O | |
| 4-Cl | 3-Cl | H | Me | O | O | |
| 4-CF$_3$ | H | 5-Cl | Et | O | O | |
| 4-Cl | H | 5-Cl | Et | O | O | |
| 4-F | H | H | Et | O | O | |
| 4-OCF$_2$H | H | H | allyl | O | O | |
| 4-SMe | H | 5-Cl | allyl | O | O | |
| 4-Cl | 3-Cl | 5-Cl | allyl | O | O | |
| 4-CF$_3$ | H | 5-F | CO$_2$Me | O | O | |
| 4-Cl | H | 5-F | C(O)Me | O | O | |
| 4-F | H | 5-OCF$_2$H | CH$_2$Ph | O | O | |
| 4-OCF$_2$H | H | 5-OCF$_2$H | CH$_2$Ph | O | O | |
| 4-SMe | H | 5-CF$_3$ | Ph | O | O | |
| 4-Cl | 3-Cl | 5-CF$_3$ | Ph | O | O | |
| 4-CF$_3$ | H | H | Me | S | O | |
| 4-Cl | H | H | Me | S | O | |
| 4-F | H | H | Me | S | O | |
| 4-CF$_3$ | H | H | H | O | NMe | |
| 4-Cl | H | H | H | O | NMe | |
| 4-F | H | 5-Cl | H | O | NMe | |
| 4-OCF$_2$H | H | 5-Cl | Me | O | NMe | |
| 4-SMe | H | H | Me | O | NMe | |
| 4-Cl | 3-Cl | H | Me | O | NMe | |
| 4-CF$_3$ | H | 5-Cl | Et | O | NMe | |
| 4-Cl | H | 5-Cl | Et | O | NMe | |
| 4-F | H | H | Et | O | NMe | |
| 4-OCF$_2$H | H | H | allyl | O | NMe | |
| 4-SMe | H | 5-Cl | allyl | O | NMe | |
| 4-Cl | 3-Cl | 5-Cl | allyl | O | NMe | |
| 4-CF$_3$ | H | 5-F | CO$_2$Me | O | NMe | |
| 4-Cl | H | 5-F | C(O)Me | O | NMe | |
| 4-F | H | 5-OCF$_2$H | CH$_2$Ph | O | NMe | |
| 4-OCF$_2$H | H | 5-OCF$_2$H | CH$_2$Ph | O | NMe | |
| 4-SMe | H | 5-CF$_3$ | Ph | O | NMe | |
| 4-Cl | 3-Cl | 5-CF$_3$ | Ph | O | NMe | |
| 4-CF$_3$ | H | H | Me | S | NMe | |
| 4-Cl | H | H | Me | S | NMe | |
| 4-F | H | H | Me | S | NMe | |
| 4-CF$_3$ | H | H | Me | O | NH | |
| 4-Cl | H | 5-Cl | Me | O | NH | |
| 4-Br | H | 5-F | Me | O | NH | |
| 4-OCF$_3$ | H | H | Me | O | NH | |
| 4-CF$_3$ | H | 5-Cl | Me | O | NEt | |
| 4-Cl | H | 5-F | Me | O | NEt | |
| 4-Br | H | H | Me | O | NEt | |
| 4-OCF$_3$ | H | 5-Cl | Me | O | N-n-C$_4$H$_9$ | |
| 4-CF$_3$ | H | 5-F | Me | O | N-n-C$_4$H$_9$ | |
| 4-Cl | H | H | Me | O | N-allyl | |
| 4-Br | H | 5-Cl | Me | O | N-allyl | |
| 4-OCF$_3$ | H | 5-F | Me | O | N-4-Cl—Ph | |
| 4-CF$_3$ | H | H | Me | O | N-4-F—Ph | |
| 4-Cl | H | 5-Cl | Me | O | NPh | |
| 4-Br | H | 5-F | Me | O | NCH$_2$Ph | |
| 4-OCF$_3$ | H | H | Me | O | NCH$_2$Ph | |
| 4-CF$_3$ | H | 5-Cl | Me | O | N—CH$_2$C(Cl)=CH$_2$ | |

TABLE 5

| $R_1{}^a$ | $R_1{}^b$ | $R_2$ | B | x | z | Phys. Prop. (m.p. °C.) |
|---|---|---|---|---|---|---|
| 4-CF$_3$ | H | H | H | O | O | |
| 4-OCF$_3$ | H | 5-Cl | H | O | O | |
| 4-OCF$_2$H | H | H | H | O | O | |
| 4-Cl | H | 5-Cl | CO$_2$Me | O | O | |
| 4-F | H | H | CO$_2$Me | O | O | |
| 4-Br | H | 5-Cl | CO$_2$Me | O | O | |
| 4-CF$_3$ | H | H | CO$_2$Me | O | O | |
| 4-OCF$_3$ | H | 5-Cl | CO$_2$Me | O | O | |
| 4-OCF$_2$H | H | H | CO$_2$Me | O | O | |
| 4-Cl | H | 5-Cl | Me | O | O | |
| 4-F | H | H | Me | O | O | |
| 4-Br | H | 5-Cl | Me | O | O | |
| 4-CF$_3$ | H | H | Et | O | O | |
| 4-OCF$_3$ | H | 5-Cl | n-Pr | O | O | |
| 4-OCF$_2$H | H | H | allyl | O | O | |
| 4-Cl | H | 5-Cl | allyl | O | O | |
| 4-F | H | H | CH$_2$-4-F—Ph | O | O | |
| 4-Br | H | 5-Cl | CH$_2$-4-Cl—Ph | O | O | |
| 4-CF$_3$ | H | H | CH$_2$CF$_3$ | O | O | |
| 4-OCF$_3$ | H | 5-Cl | (CH$_2$)$_4$Cl | O | O | |
| 4-OCF$_2$H | H | H | i-Pr | O | O | |
| 4-CF$_3$ | H | 5-Cl | OH | O | O | |
| 4-OCF$_3$ | H | 5-Cl | OAc | O | O | |
| 4-OCF$_2$H | 3-Cl | 5-Cl | OMe | O | O | |
| 4-Cl | H | 5-Cl | C(O)CH$_3$ | O | O | |
| 4-F | H | 5-Cl | C(O)NHMe | O | O | |
| 4-Br | H | 5-Cl | C(S)NMe$_2$ | O | O | |
| 4-CF$_3$ | H | 5-F | Me | O | O | |
| 4-OCF$_3$ | H | 5-F | n-Bu | O | O | |
| 4-OCF$_2$H | 3-Cl | 5-F | alkyl | O | O | |
| 4-Cl | H | 5-F | i-Pr | O | O | |
| 4-F | H | 5-F | CH$_2$Ph | O | O | |
| 4-Br | H | 5-F | Ph | O | O | |
| 4-CF$_3$ | H | 5-CF$_3$ | CH$_2$CH$_2$F | O | O | |
| 4-OCF$_3$ | H | 5-CF$_3$ | CH$_2$SCH$_3$ | O | O | |

TABLE 5-continued

| $R_1{}^a$ | $R_1{}^b$ | $R_2$ | B | x | z | Phys. Prop. (m.p. °C.) |
|---|---|---|---|---|---|---|
| 4-OCF$_2$H | 3-Cl | 5-CF$_3$ | CH$_2$OCH$_3$ | O | O | |
| 4-Cl | H | 5-CF$_3$ | CH$_2$CN | O | O | |
| 4-F | H | 5-CF$_3$ | CH$_2$CO$_2$Me | O | O | |
| 4-Br | H | 5-CF$_3$ | CS$_2$Me | O | O | |
| 4-CF$_3$ | H | H | Me | S | O | |
| 4-OCF$_3$ | H | H | Me | S | O | |
| 4-OCF$_2$H | 3-Cl | H | Me | S | O | |
| 4-CF$_3$ | H | H | H | O | NMe | |
| 4-OCF$_3$ | H | 5-Cl | H | O | NMe | |
| 4-OCF$_2$H | H | H | H | O | NMe | |
| 4-Cl | H | 5-Cl | CO$_2$Me | O | NMe | |
| 4-F | H | H | CO$_2$Me | O | NMe | |
| 4-Br | H | 5-Cl | CO$_2$Me | O | NMe | |
| 4-CF$_3$ | H | H | CO$_2$Me | O | NMe | |
| 4-OCF$_3$ | H | 5-Cl | CO$_2$Me | O | NMe | |
| 4-OCF$_2$H | H | H | CO$_2$Me | O | NMe | |
| 4-Cl | H | 5-Cl | Me | O | NMe | |
| 4-F | H | H | Me | O | NMe | |
| 4-Br | H | 5-Cl | Me | O | NMe | |
| 4-CF$_3$ | H | H | Et | O | NMe | |
| 4-OCF$_2$H | H | H | allyl | O | NMe | |
| 4-Cl | H | 5-Cl | allyl | O | NMe | |
| 4-F | H | H | CH$_2$-4-F—Ph | O | NMe | |
| 4-Br | H | 5-Cl | CH$_2$-4-Cl—Ph | O | NMe | |
| 4-CF$_3$ | H | H | CH$_2$CF$_3$ | O | NMe | |
| 4-OCF$_3$ | H | 5-Cl | (CH$_2$)$_4$Cl | O | NMe | |
| 4-OCF$_2$H | H | H | i-Pr | O | NMe | |
| 4-CF$_3$ | H | 5-Cl | OH | O | NMe | |
| 4-OCF$_3$ | H | H | OAc | O | NMe | |
| 4-OCF$_2$H | 3-Cl | 5-Cl | OMe | O | NMe | |
| 4-Cl | H | 5-Cl | C(O)CH$_3$ | O | NMe | |
| 4-F | H | 5-Cl | C(O)NHMe | O | NMe | |
| 4-Br | H | 5-Cl | C(S)NMe$_2$ | O | NMe | |
| 4-CF$_3$ | H | 5-F | Me | O | NMe | |
| 4-OCF$_3$ | H | 5-F | n-Bu | O | NMe | |
| 4-OCF$_2$H | 3-Cl | 5-F | allyl | O | NMe | |
| 4-Cl | H | 5-F | i-Pr | O | NMe | |
| 4-F | H | 5-F | CH$_2$Ph | O | NMe | |
| 4-Br | H | 5-F | Ph | O | NMe | |
| 4-CF$_3$ | H | 5-CF$_3$ | CH$_2$CH$_2$F | O | NMe | |
| 4-OCF$_3$ | H | 5-CF$_3$ | CH$_2$OCH$_3$ | O | NMe | |
| 4-OCF$_2$H | 3-Cl | 5-CF$_3$ | CH$_2$OCH$_3$ | O | NMe | |
| 4-Cl | H | 5-CF$_3$ | CH$_2$CN | O | NMe | |
| 4-F | H | 5-CF$_3$ | CH$_2$CO$_2$Me | O | NMe | |
| 4-Br | H | 5-CF$_3$ | CS$_2$Me | O | NMe | |
| 4-CF$_3$ | H | H | Me | S | NMe | |
| 4-OCF$_3$ | H | H | Me | S | NMe | |
| 4-OCF$_2$H | 3-Cl | H | Me | S | NMe | |
| 4-CF$_3$ | H | H | Me | O | NEt | |
| 4-CF$_3$ | H | 5-F | CO$_2$Me | O | NEt | |
| 4-CF$_3$ | H | 5-Cl | Me | O | N-n-Bu | |
| 4-CF$_3$ | H | H | CO$_2$Me | O | N-n-Bu | |
| 4-CF$_3$ | H | 5-F | Me | O | N-allyl | |
| 4-CF$_3$ | H | 5-Cl | CO$_2$Me | O | N-allyl | |
| 4-CF$_3$ | H | H | Me | O | N—Ph | |
| 4-CF$_3$ | H | 5-F | CO$_2$Me | O | N—Ph | |
| 4-CF$_3$ | H | 5-Cl | Me | O | N-4-Cl—Ph | |
| 4-CF$_3$ | H | H | CO$_2$Me | O | N-4-Cl—Ph | |

TABLE 6

| $R_1$ | $R_2$ | B | t | y | Phys. Prop. (m.p. °C.) |
|---|---|---|---|---|---|
| 4-CF$_3$ | H | H | 0 | Me | |
| 4-Cl | H | Me | 0 | C(O)Me | |
| 4-OCF$_2$H | H | CO$_2$Me | 0 | n-Bu | |
| 4-CF$_3$ | H | C(O)Me | 0 | SMe | |
| 4-Cl | H | CO$_2$Et | 0 | SCCl$_3$ | |
| 4-OCF$_3$ | H | H | 1 | Me | |
| 4-CF$_3$ | H | H | 1 | C(O)Me | oil |
| 4-F | H | CO$_2$Me | 1 | Me | |
| 4-OCF$_2$H | H | CO$_2$Me | 1 | C(O)Me | |
| 4-CF$_3$ | H | Me | 1 | C(O)CF$_3$ | |
| 4-Cl | H | Me | 1 | CO$_2$Et | |
| 4-CF$_3$ | H | CO$_2$CH$_2$CF$_3$ | 1 | Me | |
| 4-OCF$_2$H | H | CO$_2$Et | 1 | Me | |
| 4-OCF$_2$H | H | CO$_2$CH$_2$CH$_2$Cl | 1 | Me | |
| 4-Br | H | CONHMe | 1 | Me | |
| 4-SCF$_2$H | H | H | 2 | 2-NO$_2$PhS | |
| 4-CF$_3$ | H | Me | 2 | CO$_2$Me | |
| 4-Cl | H | Me | 2 | C(O)Me | |
| 4-CF$_3$ | H | CO$_2$Me | 2 | C(O)Me | |
| 4-Cl | H | CO$_2$Me | 2 | Me | |
| 4-CF$_3$ | H | CO$_2$Me | 1 | C(O)Me | 110 to 115 |
| 4-CF$_3$ | H | CO$_2$Me | 1 | Me | glass |
| 4-CF$_3$ | H | CO$_2$Me | 1 | CO$_2$Me | glass |
| 4-CF$_3$ | 5-Cl | CO$_2$Me | 1 | C(O)Me | |
| 4-CF$_3$ | 5-Cl | CO$_2$Me | 1 | Me | |
| 4-CF$_3$ | 5-Cl | CO$_2$Me | 1 | CO$_2$Me | |
| 4-CF$_3$ | 4-F | CO$_2$Me | 1 | C(O)Me | |
| 4-CF$_3$ | 5-F | CO$_2$Me | 1 | C(O)Me | |
| 4-CF$_3$ | 4-F | CO$_2$Me | 1 | CO$_2$Me | |
| 4-CF$_3$ | 5-F | CO$_2$Me | 1 | CO$_2$Me | |
| 4-CF$_3$ | H | H | 1 | CO$_2$-t-Bu | 178 to 179 |

TABLE 7

| $R_1$ | $R_2$ | B | t | y | v | Phys. Prop. (m.p. °C.) |
|---|---|---|---|---|---|---|
| 4-CF$_3$ | H | Me | 0 | Me | O | |
| 4-CF$_3$ | H | Me | 1 | Me | NMe | |
| 4-CF$_3$ | 5-Cl | CO$_2$Me | 2 | Me | S | |
| 4-CF$_3$ | 5-Cl | CO$_2$Me | 0 | Me | O | |
| 4-CF$_3$ | 5-Cl | Me | 1 | Me | NMe | |
| 4-CF$_3$ | 5-Cl | Me | 2 | C(O)Me | S | |
| 4-CF$_3$ | 5-F | CO$_2$Me | 0 | C(O)Me | O | |
| 4-CF$_3$ | 5-F | CO$_2$Me | 1 | C(O)Me | NMe | |
| 4-CF$_3$ | 5-F | Me | 2 | C(O)Me | SO | |
| 4-CF$_3$ | 5-F | Me | 0 | C(O)Me | SO$_2$ | |
| 4-CF$_3$ | H | CO$_2$Me | 1 | SCCl$_3$ | O | |
| 4-CF$_3$ | H | CO$_2$Me | 2 | SCCl$_3$ | NMe | |
| 4-CF$_3$ | H | Me | 0 | CO$_2$Me | S | |
| 4-CF$_3$ | H | Me | 1 | CO$_2$Me | O | |
| 4-CF$_3$ | 5-OCF$_2$H | CO$_2$Me | 2 | n-Pr | NMe | |
| 4-CF$_3$ | 5-OCF$_2$H | CO$_2$Me | 0 | n-Pr | S | |
| 4-CF$_3$ | 5-CF$_3$ | Me | 1 | C(O)CF$_3$ | O | |
| 4-CF$_3$ | 5-CF$_3$ | Me | 2 | C(O)CF$_3$ | NMe | |
| 4-CF$_3$ | 5-Cl | CO$_2$Me | 0 | SMe | S | |
| 4-CF$_3$ | 5-Cl | CO$_2$Me | 1 | SMe | O | |
| 4-CF$_3$ | H | H | 1 | Me | S | 151 to 152 |
| 4-CF$_3$ | H | H | 1 | CO$_2$Me | S | 150 to 158 |
| 4-CF$_3$ | H | H | 1 | C(O)Me | S | 80 to 85 |
| 4-CF$_3$ | 5-Cl | H | 1 | C(O)Me | S | 97 to 99 |
| 4-CF$_3$ | 5-CL | H | 1 | CO$_2$Me | S | 170 to 172 |
| 4-CF$_3$ | 5-Cl | H | 1 | Me | S | 180 to 183 |
| 4-Cl | H | H | 1 | C(O)Me | S | 140 to 150 |
| 4-Cl | H | H | 1 | Me | S | 125 to 127 |
| 4-Cl | 5-Cl | H | 1 | C(O)Me | S | 127 to 142 |
| 4-Cl | 5-Cl | H | 1 | Me | S | 160 to 165 |

TABLE 8

| $R_1$ | $R_2$ | B | t | y | v | Phys. Prop. (m.p. °C.) |
|---|---|---|---|---|---|---|
| 4-CF$_3$ | H | Me | 0 | Me | O | |
| 4-CF$_3$ | H | Me | 1 | Me | NMe | |
| 4-CF$_3$ | 5-Cl | CO$_2$Me | 2 | Me | S | |
| 4-CF$_3$ | 5-Cl | CO$_2$Me | 0 | Me | O | |
| 4-CF$_3$ | 5-Cl | Me | 1 | Me | NMe | |
| 4-CF$_3$ | 5-Cl | Me | 2 | C(O)Me | S | |
| 4-CF$_3$ | 5-F | CO$_2$Me | 0 | C(O)Me | O | |
| 4-CF$_3$ | 5-F | CO$_2$Me | 1 | C(O)Me | NMe | |
| 4-CF$_3$ | 5-F | Me | 2 | C(O)Me | SO | |
| 4-CF$_3$ | 5-F | Me | 0 | C(O)Me | SO$_2$ | |
| 4-CF$_3$ | H | CO$_2$Me | 1 | SCCl$_3$ | O | |
| 4-CF$_3$ | H | CO$_2$Me | 2 | SCCl$_3$ | NMe | |
| 4-CF$_3$ | H | Me | 0 | CO$_2$Me | S | |
| 4-CF$_3$ | H | Me | 1 | CO$_2$Me | O | |
| 4-CF$_3$ | 5-OCF$_2$H | CO$_2$Me | 2 | n-Pr | NMe | |

TABLE 8-continued

| R₁ | R₂ | B | t | y | v | Phys. Prop. (m.p. °C.) |
|---|---|---|---|---|---|---|
| 4-CF₃ | 5-OCF₂H | CO₂Me | 0 | n-Pr | S | |
| 4-CF₃ | 5-CF₃ | Me | 1 | C(O)CF₃ | O | |
| 4-CF₃ | 5-CF₃ | Me | 2 | C(O)CF₃ | NMe | |
| 4-CF₃ | 5-Cl | CO₂Me | 0 | SMe | S | |
| 4-CF₃ | 5-Cl | CO₂Me | 1 | SMe | O | |

TABLE 9

| R₁ | R₂ | B | y | z | Phys. Prop. (m.p. °C.) |
|---|---|---|---|---|---|
| 4-CF₃ | H | Me | Me | O | |
| 4-Cl | H | Me | C(O)Me | NMe | |
| 4-CF₃ | H | Me | Et | O | |
| 4-Cl | 5-Cl | Me | CO₂Me | NMe | |
| 4-CF₃ | 5-Cl | Et | n-Pr | O | |
| 4-Cl | 5-F | Et | CO₂Et | NMe | |
| 4-CF₃ | 5-F | Et | C(O)Me | O | |
| 4-Cl | 5-Cl | Et | S—CCl₃ | NMe | |
| 4-CF₃ | 5-Cl | (CH₂)₃Cl | SPh | O | |
| 4-Cl | H | (CH₂)₃Cl | Me | NMe | |
| 4-CF₃ | H | CH₂Ph | Me | O | |
| 4-Cl | H | CH₂Ph | C(O)Me | NMe | |
| 4-CF₃ | 5-OCF₃ | Ph | C(O)CF₃ | O | |
| 4-Cl | 5-OMe | Ph | 2-NO₂PhS | NMe | |
| 4-CF₃ | 5-Cl | 4-Cl—Ph | Me | O | |
| 4-Cl | 5-F | 4-Cl—Ph | Et | NMe | |
| 4-CF₃ | H | allyl | C(O)Me | O | |
| 4-Cl | H | allyl | CO₂Et | NMe | |
| 4-CF₃ | 5-Cl | OH | SCCl₃ | O | |
| 4-Cl | H | OH | Me | NMe | |
| 4-CF₃ | H | OAc | C(O)Me | O | |
| 4-Cl | H | OAc | Me | NMe | |

TABLE 10

| R₁ | R₂ | B | y | z | Phys. Prop. (m.p. °C.) |
|---|---|---|---|---|---|
| 4-CF₃ | H | Me | Me | O | |
| 4-Cl | H | Me | C(O)Me | NMe | |
| 4-CF₃ | H | Me | Et | O | |
| 4-Cl | 5-Cl | Me | CO₂Me | NMe | |
| 4-CF₃ | 5-Cl | Et | n-Pr | O | |
| 4-Cl | 5-F | Et | CO₂Et | NMe | |
| 4-CF₃ | 5-F | Et | C(O)Me | O | |
| 4-Cl | 5-Cl | Et | S—CCl₃ | NMe | |
| 4-CF₃ | 5-Cl | (CH₂)₃Cl | SPh | O | |
| 4-Cl | H | (CH₂)₃Cl | Me | NMe | |
| 4-CF₃ | H | CH₂Ph | Me | O | |
| 4-Cl | H | CH₂Ph | C(O)Me | NMe | |
| 4-CF₃ | 5-OCF₃ | Ph | C(O)CF₃ | O | |
| 4-Cl | 5-OMe | Ph | 2-NO₂PhS | NMe | |
| 4-CF₃ | 5-Cl | 4-Cl—Ph | Me | O | |
| 4-Cl | 5-F | 4-Cl—Ph | Et | NMe | |
| 4-CF₃ | H | allyl | C(O)Me | O | |
| 4-Cl | H | allyl | CO₂Et | NMe | |
| 4-CF₃ | 5-Cl | OH | SCCl₃ | O | |
| 4-Cl | H | OH | Me | NMe | |
| 4-CF₃ | H | OAc | C(O)Me | O | |
| 4-Cl | H | OAc | Me | NMe | |

TABLE 11

| R₁ | R₂ | B | t | J | K | Prop. Prop. (m.p. °C.) |
|---|---|---|---|---|---|---|
| 4-CF₃ | H | H | 0 | Me | H | |
| 4-Cl | H | H | 1 | Me | H | |
| 4-CF₃ | H | Me | 2 | Me | H | |
| 4-Cl | 5-Cl | Me | 0 | Ph | H | |
| 4-CF₃ | 5-Cl | CO₂Me | 1 | Ph | H | |
| 4-Cl | 5-Cl | CO₂Me | 2 | 4-Cl—Ph | H | |
| 4-CF₃ | H | H | 0 | 4-F—Ph | H | |
| 4-Cl | H | H | 1 | 4-CF₃—Ph | H | |
| 4-CF₃ | H | Me | 2 | Et | H | |

TABLE 11-continued

| R₁ | R₂ | B | t | J | K | Prop. Prop. (m.p. °C.) |
|---|---|---|---|---|---|---|
| 4-Cl | 5-F | Me | 0 | n-Pr | H | |
| 4-CF₃ | 5-F | CO₂Me | 1 | n-Bu | H | |
| 4-Cl | 5-F | CO₂Me | 2 | Me | Me | |
| 4-CF₃ | H | H | 0 | Me | Me | |
| 4-Cl | H | H | 1 | Me | Me | |
| 4-CF₃ | H | Me | 2 | Me | Me | |
| 4-Cl | 5-Cl | Me | 0 | Ph | Me | |
| 4-CF₃ | 5-Cl | CO₂Me | 1 | Ph | Me | |
| 4-Cl | 5-Cl | CO₂Me | 2 | Ph | Me | |
| 4-CF₃ | H | H | 0 | Ph | Me | |
| 4-Cl | H | H | 1 | Et | Me | |
| 4-CF₃ | H | Me | 2 | n-Pr | Me | |
| 4-Cl | H | Me | 0 | n-Bu | Me | |
| 4-CF₃ | H | H | 1 | 4-F—Ph | H | 199 to 201 |
| 4-CF₃ | H | H | 1 | 4-Cl—Ph | H | 187 to 188 |
| 4-CF₃ | 5-Cl | H | 1 | 4-F—Ph | H | |
| 4-CF₃ | 5-Cl | H | 1 | 4-Cl—Ph | H | |
| 4-CF₃ | 4-F | H | 1 | 4-F—Ph | H | |
| 4-CF₃ | 4-F | H | 1 | 4-Cl—Ph | H | |
| 4-CF₃ | 5-OCF₂H | H | 1 | 4-F—Ph | H | |
| 4-CF₃ | 5-OCF₂H | H | 1 | 4-Cl—Ph | H | |
| 4-Cl | H | H | 1 | 4-F—Ph | H | 208 to 209 |
| 4-Cl | H | H | 1 | 4-Cl—Ph | H | 179 to 181 |

TABLE 12

| R₁ | R₂ | B | t | J | K | V | Phys. Prop. (m.p. °C.) |
|---|---|---|---|---|---|---|---|
| 4-CF₃ | H | H | 0 | Me | H | O | |
| 4-CF₃ | H | Me | 1 | Me | H | O | |
| 4-CF₃ | 4-F | Et | 2 | Ph | H | O | |
| 4-CF₃ | H | CO₂Me | 0 | Ph | Me | O | |
| 4-CF₃ | H | CO₂Et | 1 | Me | Me | O | |
| 4-CF₃ | H | H | 2 | Me | Me | O | |
| 4-CF₃ | 4-Cl | Me | 0 | 4-Cl—Ph | Me | O | |
| 4-CF₃ | H | Et | 1 | Me | H | S | |
| 4-CF₃ | H | CO₂Me | 2 | Me | H | S | |
| 4-CF₃ | 4-Br | CO₂Et | 0 | Ph | H | S | |
| 4-CF₃ | H | H | 1 | Ph | Me | S | |
| 4-CF₃ | H | Me | 2 | Me | Me | S | |
| 4-CF₃ | H | Et | 0 | Me | Me | S | |
| 4-CF₃ | H | CO₂Me | 1 | 4-F—Ph | Me | S | |
| 4-CF₃ | H | CO₂Et | 2 | Me | H | NMe | |
| 4-CF₃ | H | H | 0 | Me | H | NMe | |
| 4-CF₃ | 5-Cl | Me | 1 | Ph | H | NMe | |
| 4-CF₃ | H | Et | 2 | Ph | Me | NMe | |
| 4-CF₃ | 5-Me | CO₂Me | 0 | Me | Me | NMe | |
| 4-CF₃ | H | CO₂Et | 1 | Me | Me | NMe | |
| 4-CF₃ | H | H | 2 | 4-Cl—Ph | Me | NMe | |

TABLE 13

| R₁ | R₂ | B | t | J | K | V | Phys. Prop. (m.p. °C.) |
|---|---|---|---|---|---|---|---|
| 4-CF₃ | H | H | 0 | Me | H | O | |
| 4-CF₃ | H | Me | 1 | Me | H | O | |
| 4-CF₃ | 4-F | Et | 2 | Ph | H | O | |
| 4-CF₃ | H | CO₂Me | 0 | Ph | Me | O | |
| 4-CF₃ | H | CO₂Et | 1 | Me | Me | O | |
| 4-CF₃ | H | H | 2 | Me | Me | O | |
| 4-CF₃ | 4-Cl | Me | 0 | 4-Cl—Ph | Me | O | |
| 4-CF₃ | H | Et | 1 | Me | H | S | |
| 4-CF₃ | H | CO₂Me | 2 | Me | H | S | |
| 4-CF₃ | 4-Br | CO₂Et | 0 | Ph | H | S | |
| 4-CF₃ | H | H | 1 | Ph | Me | S | |
| 4-CF₃ | H | Me | 2 | Me | Me | S | |
| 4-CF₃ | H | Et | 0 | Me | Me | S | |
| 4-CF₃ | H | CO₂Me | 1 | 4-F—Ph | Me | S | |
| 4-CF₃ | H | CO₂Et | 2 | Me | H | NMe | |
| 4-CF₃ | H | H | 0 | Me | H | NMe | |
| 4-CF₃ | 5-Cl | Me | 1 | Ph | H | NMe | |
| 4-CF₃ | H | Et | 2 | Ph | Me | NMe | |
| 4-CF₃ | 5-Me | CO₂Me | 0 | Me | Me | NMe | |
| 4-CF₃ | H | CO₂Et | 1 | Me | Me | NMe | |

TABLE 13-continued

| R1 | R2 | B | t | J | K | V | Phys. Prop. (m.p. °C.) |
|---|---|---|---|---|---|---|---|
| 4-CF3 | H | H | 2 | 4-Cl—Ph | Me | NMe | |

TABLE 14

| R1 | R2 | B | J | K | Z | Phys. Prop. (m.p. °C.) |
|---|---|---|---|---|---|---|
| 4-CF3 | H | H | Me | H | O | |
| 4-Cl | H | Me | Me | Me | O | |
| 4-OCF2H | H | Me | Ph | H | O | |
| 4-CF3 | H | allyl | 4-Cl—Ph | Me | NMe | |
| 4-Cl | H | allyl | Me | H | NMe | |
| 4-OCF2H | 5-F | CH2Ph | 4-F—Ph | Me | NMe | |
| 4-CF3 | H | CH2Ph | Me | H | O | |
| 4-Cl | H | Ph | Me | Me | O | |
| 4-OCF2H | H | Ph | Ph | H | O | |
| 4-CF3 | H | 4-F—Ph | Ph | Me | NMe | |
| 4-Cl | H | 4-F—Ph | Me | H | NMe | |
| 4-OCF2H | 5-Cl | OH | Me | Me | NMe | |
| 4-CF3 | H | OH | Me | H | O | |
| 4-Cl | H | OMe | Et | Me | O | |
| 4-OCF2H | H | OMe | Ph | H | O | |
| 4-CF3 | H | CO2Et | 4-Cl—Ph | Me | NMe | |
| 4-Cl | H | CO2Et | Me | H | NMe | |
| 4-OCF2H | 5-Cl | CONHMe | Ph | Me | NMe | |
| 4-CF3 | H | CONHMe | Me | H | O | |
| 4-Cl | H | n-Bu | Ph | Me | H | O |
| 4-OCF2H | H | n-Bu | Me | H | O | |

TABLE 15

| R1 | R2 | B | J | K | Z | Phys. Prop. (m.p. °C.) |
|---|---|---|---|---|---|---|
| 4-CF3 | H | Me | Me | H | O | |
| 4-Cl | H | CO2Me | Me | H | O | |
| 4-OCF2H | H | H | Me | H | O | |
| 4-CF3 | H | Me | Ph | H | O | |
| 4-Cl | H | CO2Me | Ph | H | O | |
| 4-OCF2H | H | H | Ph | H | O | |
| 4-CF3 | 5-Cl | Et | 4-Cl—Ph | H | NMe | |
| 4-Cl | H | CO2Et | 4-Cl—Ph | H | NMe | |
| 4-OCF2H | H | (CH2)3Cl | 4-Cl—Ph | H | NMe | |
| 4-CF3 | H | Me | Me | H | NMe | |
| 4-Cl | H | H | Me | H | NMe | |
| 4-OCF2H | H | CO2Me | Me | Me | O | |
| 4-CF3 | H | H | Me | Me | O | |
| 4-Cl | H | Me | Me | Me | O | |
| 4-OCF2H | 5-F | C(O)Me | Ph | Me | O | |
| 4-CH3 | H | C(O)Et | Ph | Me | O | |
| 4-Cl | H | Me | Me | Me | NMe | |
| 4-OCF2H | H | Et | Me | Me | NMe | |
| 4-CF3 | H | n-Pr | Ph | Me | NMe | |
| 4-Cl | H | CO2Me | Ph | Me | NMe | |
| 4-OCF2H | H | Me | 4-Cl—Ph | Me | NMe | |
| 4-CF3 | H | Et | 4-Cl—Ph | Me | NMe | |

TABLE 16

| R1 | R2 | B | $R_8^a$ | $R_8^b$ | $R_8^c$ | $R_8^d$ | Phys. Prop. (m.p. °C.) |
|---|---|---|---|---|---|---|---|
| 4-CF3 | H | H | Me | H | H | H | |
| 4-Cl | H | H | Me | H | H | H | |
| 4-Br | H | H | Me | H | H | H | |
| 4-OCF2H | H | H | Me | H | H | H | |
| 4-CF3 | H | CO2Me | Me | H | H | H | |
| 4-Cl | H | CO2Me | Me | H | H | H | |
| 4-Br | H | CO2Me | Me | H | H | H | |
| 4-OCF2H | H | CO2Me | Me | H | H | H | |
| 4-CF3 | 5-Cl | H | Me | H | H | H | |
| 4-Cl | 5-Cl | H | Me | H | H | H | |
| 4-Br | 5-Cl | H | Me | H | H | H | |
| 4-OCF2H | 5-Cl | H | Me | H | H | H | |
| 4-CF3 | 5-Cl | CO2Me | Me | H | H | H | |
| 4-Cl | 5-Cl | CO2Me | Me | H | H | H | |
| 4-Br | 5-Cl | CO2Me | Me | H | H | H | |
| 4-OCF2H | 5-Cl | CO2Me | Me | H | H | H | |
| 4-CF3 | 4-F | H | Me | H | H | H | |
| 4-Cl | 4-F | H | Me | H | H | H | |
| 4-Br | 4-F | H | Me | H | H | H | |
| 4-OCF2H | 4-F | H | Me | H | H | H | |
| 4-CF3 | 4-F | CO2Me | Me | H | H | H | |
| 4-Cl | 4-F | CO2Me | Me | H | H | H | |
| 4-Br | 4-F | CO2Me | Me | H | H | H | |
| 4-OCF2H | 4-F | CO2Me | Me | H | H | H | |
| 4-CF3 | H | H | Me | Me | H | H | |
| 4-Cl | H | H | Me | Me | H | H | |
| 4-Br | H | H | Me | Me | H | H | |
| 4-OCF3 | H | H | Me | Me | H | H | |
| 4-CF3 | H | CO2Me | Me | Me | H | H | |
| 4-Cl | H | CO2Me | Me | Me | H | H | |
| 4-Br | H | CO2Me | Me | Me | H | H | |
| 4-OCF3 | H | CO2Me | Me | Me | H | H | |
| 4-CF3 | 5-OCF2H | H | Me | Me | H | H | |
| 4-Cl | 5-OCF2H | H | Me | Me | H | H | |
| 4-Br | 5-OCF2H | H | Me | Me | H | H | |
| 4-OCF3 | 5-OCF2H | H | Me | Me | H | H | |
| 4-CF3 | 5-OCF2H | CO2Me | Me | Me | H | H | |
| 4-Cl | 5-OCF2H | CO2Me | Me | Me | H | H | |
| 4-Br | 5-OCF2H | CO2Me | Me | Me | H | H | |
| 4-OCF3 | 5-OCF2H | CO2Me | Me | Me | H | H | |
| 4-CF3 | 5-Cl | H | Me | Me | H | H | |
| 4-Cl | 5-Cl | H | Me | Me | H | H | |
| 4-Br | 5-Cl | H | Me | Me | H | H | |

TABLE 16-continued

| $R_1$ | $R_2$ | B | $R_8{}^a$ | $R_8{}^b$ | $R_8{}^c$ | $R_8{}^d$ | Phys. Prop. (m.p. °C.) |
|---|---|---|---|---|---|---|---|
| 4-OCF$_3$ | 5-Cl | H | Me | Me | H | H | |
| 4-CF$_3$ | 5-Cl | CO$_2$Me | Me | Me | H | H | |
| 4-Cl | 5-Cl | CO$_2$Me | Me | Me | H | H | |
| 4-Br | 5-Cl | CO$_2$Me | Me | Me | H | H | |
| 4-OCF$_3$ | 5-Cl | CO$_2$Me | Me | Me | H | H | |
| 4-CF$_3$ | H | H | H | Me | H | H | |
| 4-Cl | H | H | H | Me | H | H | |
| 4-CF$_3$ | H | CO$_2$Me | H | Me | H | H | |
| 4-Cl | H | CO$_2$Me | H | Me | H | H | |
| 4-CF$_3$ | 5-Cl | H | H | Me | H | H | |
| 4-Cl | 5-Cl | H | H | Me | H | H | |
| 4-CF$_3$ | 5-Cl | CO$_2$Me | H | Me | H | H | |
| 4-Cl | 5-Cl | CO$_2$Me | H | Me | H | H | |
| 4-CF$_3$ | H | H | H | H | Me | H | |
| 4-Cl | H | H | H | H | Me | H | |
| 4-CF$_3$ | H | CO$_2$Me | H | H | Me | H | |
| 4-Cl | H | CO$_2$Me | H | H | Me | H | |
| 4-CF$_3$ | 5-Cl | H | H | H | Me | H | |
| 4-Cl | 5-Cl | H | H | H | Me | H | |
| 4-CF$_3$ | 5-Cl | CO$_2$Me | H | H | Me | H | |
| 4-Cl | 5-Cl | CO$_2$Me | H | H | Me | H | |
| 4-CF$_3$ | H | H | H | H | H | Me | |
| 4-Cl | H | H | H | H | H | Me | |
| 4-CF$_3$ | H | CO$_2$Me | H | H | H | Me | |
| 4-Cl | H | CO$_2$Me | H | H | H | Me | |
| 4-CF$_3$ | 5-Cl | H | H | H | H | Me | |
| 4-Cl | 5-Cl | H | H | H | H | Me | |
| 4-CF$_3$ | 5-Cl | CO$_2$Me | H | H | H | Me | |
| 4-Cl | 5-Cl | CO$_2$Me | H | H | H | Me | |
| CF$_3$ | H | H | H | H | Me | Me | |
| Cl | H | H | H | H | Me | Me | |
| Br | H | H | H | H | Me | Me | |
| CF$_3$ | H | CO$_2$Me | H | H | Me | Me | |
| Cl | H | CO$_2$Me | H | H | Me | Me | |
| Br | H | CO$_2$Me | H | H | Me | Me | |
| CF$_3$ | 5-Cl | H | H | H | Me | Me | |
| Cl | 5-Cl | H | H | H | Me | Me | |
| Br | 5-Cl | H | H | H | Me | Me | |
| CF$_3$ | 5-Cl | CO$_2$Me | H | H | Me | Me | |
| Cl | 5-Cl | CO$_2$Me | H | H | Me | Me | |
| Br | 5-Cl | CO$_2$Me | H | H | Me | Me | |
| CF$_3$ | 5-OCF$_2$H | H | H | H | Me | Me | |
| Cl | 5-OCF$_2$H | H | H | H | Me | Me | |
| Br | 5-OCF$_2$H | H | H | H | Me | Me | |
| CF$_3$ | 5-OCF$_2$H | CO$_2$Me | H | H | Me | Me | |
| Cl | 5-OCF$_2$H | CO$_2$Me | H | H | Me | Me | |
| Br | 5-OCF$_2$H | CO$_2$Me | H | H | Me | Me | |
| CF$_3$ | 4-F | H | H | H | Me | Me | |
| Cl | 4-F | H | H | H | Me | Me | |
| Br | 4-F | H | H | H | Me | Me | |
| CF$_3$ | 4-F | CO$_2$Me | H | H | Me | Me | |
| Cl | 4-F | CO$_2$Me | H | H | Me | Me | |
| Br | 4-F | CO$_2$Me | H | H | Me | Me | |
| 4-CF$_3$ | H | CO$_2$Me | i-Pr | H | H | H | |
| 4-CF$_3$ | H | CO$_2$Me | H | i-Pr | H | H | |
| 4-CF$_3$ | H | CO$_2$Me | H | H | Ph | H | |
| 4-CF$_3$ | H | CO$_2$Me | H | H | H | Ph | |
| 4-CF$_3$ | 5-Cl | CO$_2$Me | Cl | H | H | H | |
| 4-CF$_3$ | 5-Cl | CO$_2$Me | H | Cl | H | H | |
| 4-CF$_3$ | 5-Cl | CO$_2$Me | F | H | H | H | |
| 4-CF$_3$ | 5-Cl | CO$_2$Me | H | F | H | H | |
| 4-CF$_3$ | 5-F | CO$_2$Me | H | H | CO$_2$Me | H | |
| 4-CF$_3$ | 5-F | CO$_2$Me | H | H | H | CO$_2$Me | |
| 4-CF$_3$ | 5-F | CO$_2$Me | Et | H | H | H | |
| 4-CF$_3$ | 5-F | CO$_2$Me | H | Et | H | H | |
| 4-CF$_3$ | 5-OCF$_2$H | CO$_2$Me | Ph | H | H | H | |
| 4-CF$_3$ | 5-OCF$_2$H | CO$_2$Me | H | Ph | H | H | |
| 4-CF$_3$ | 5-OCF$_2$H | CO$_2$Me | H | Me | Me | H | |
| 4-CF$_3$ | 5-OCF$_2$H | CO$_2$Me | Me | H | H | Me | |
| 4-CF$_3$ | 4-Cl | CO$_2$Me | i-Pr | H | H | H | |
| 4-CF$_3$ | 4-Cl | CO$_2$Me | H | i-Pr | H | H | |
| 4-CF$_3$ | 4-Cl | CO$_2$Me | Et | Et | H | H | |
| 4-CF$_3$ | 4-Cl | CO$_2$Me | Et | Me | H | H | |
| 4-CF$_3$ | 4-F | CO$_2$Me | Br | H | H | H | |
| 4-CF$_3$ | 4-F | CO$_2$Me | H | Br | H | H | |
| 4-CF$_3$ | 4-F | CO$_2$Me | i-Pr | H | H | H | |
| 4-CF$_3$ | 4-F | CO$_2$Me | H | i-Pr | H | H | |

TABLE 17

| $R_1$ | $R_2$ | B | V | $R_8^a$ | $R_8^b$ | Phys. Prop. (m.p. °C.) |
|---|---|---|---|---|---|---|
| 4-CF$_3$ | H | H | O | Me | H | |
| 4-Cl | H | H | O | Me | H | |
| 4-Br | H | H | O | Me | H | |
| 4-OCF$_2$H | H | H | O | Me | H | |
| 4-CF$_3$ | H | H | O | H | Me | |
| 4-Cl | H | H | O | H | Me | |
| 4-Br | H | H | O | H | Me | |
| 4-OCF$_2$H | H | H | O | H | Me | |
| 4-CF$_3$ | H | H | O | Me | Me | |
| 4-Cl | H | H | O | Me | Me | |
| 4-Br | H | H | O | Me | Me | |
| 4-OCF$_2$H | H | H | O | Me | Me | |
| 4-CF$_3$ | H | H | O | Ph | H | |
| 4-Cl | H | H | O | Ph | H | |
| 4-Br | H | H | O | Ph | H | |
| 4-OCF$_2$H | H | H | O | Ph | H | |
| 4-CF$_3$ | H | H | O | H | Ph | |
| 4-Cl | H | H | O | H | Ph | |
| 4-Br | H | H | O | H | Ph | |
| 4-OCF$_2$H | H | H | O | H | Ph | |
| 4-CF$_3$ | H | H | O | CO$_2$Me | H | |
| 4-Cl | H | H | O | CO$_2$Me | H | |
| 4-Br | H | H | O | H | CO$_2$Me | |
| 4-OCF$_2$H | H | H | O | H | CO$_2$Me | |
| 4-CF$_3$ | 5-Cl | H | O | Me | H | |
| 4-Cl | 5-Cl | H | O | Me | H | |
| 4-Br | 5-Cl | H | O | Me | H | |
| 4-OCF$_2$H | 5-Cl | H | O | Me | H | |
| 4-CF$_3$ | 5-Cl | H | O | H | Me | |
| 4-Cl | 5-Cl | H | O | H | Me | |
| 4-Br | 5-Cl | H | O | H | Me | |
| 4-OCF$_2$H | 5-Cl | H | O | H | Me | |
| 4-CF$_3$ | 5-Cl | H | O | Me | Me | |
| 4-Cl | 5-Cl | H | O | Me | Me | |
| 4-Br | 5-Cl | H | O | Me | Me | |
| 4-OCF$_2$H | 5-Cl | H | O | Me | Me | |
| 4-CF$_3$ | 5-Cl | H | O | Ph | H | |
| 4-Cl | 5-Cl | H | O | Ph | H | |
| 4-Br | 5-Cl | H | O | Ph | H | |
| 4-OCF$_2$H | 5-Cl | H | O | Ph | H | |
| 4-CF$_3$ | 5-Cl | H | O | H | Ph | |
| 4-Cl | 5-Cl | H | O | H | Ph | |
| 4-Br | 5-Cl | H | O | H | Ph | |
| 4-OCF$_2$H | 5-Cl | H | O | H | Ph | |
| 4-CF$_3$ | 5-Cl | H | O | CO$_2$Me | H | |
| 4-Cl | 5-Cl | H | O | CO$_2$Me | H | |
| 4-Br | 5-Cl | H | O | H | CO$_2$Me | |
| 4-OCF$_2$H | 5-Cl | H | O | H | CO$_2$Me | |
| 4-CF$_3$ | H | H | S | Me | H | 208 to 210 |
| 4-Cl | H | H | S | Me | H | 172 to 178 |
| 4-Br | H | H | S | Me | H | 185 to 187 |
| 4-OCF$_2$H | H | H | S | Me | H | |
| 4-CF$_3$ | H | H | S | H | Me | 168 to 170 |
| 4-Cl | H | H | S | H | Me | 155 to 156 |
| 4-Br | H | H | S | H | Me | 172 to 180 |
| 4-OCF$_2$H | H | H | S | H | Me | |
| 4-CF$_3$ | H | H | S | Me | Me | 183 to 184 |
| 4-Cl | H | H | S | Me | Me | 181 to 186 |
| 4-Br | H | H | S | Me | Me | 182 to 185 |
| 4-OCF$_2$H | H | H | S | Me | Me | |
| 4-CF$_3$ | H | H | S | Ph | H | |
| 4-Cl | H | H | S | Ph | H | |
| 4-Br | H | H | S | Ph | H | |
| 4-OCF$_2$H | H | H | S | Ph | H | |
| 4-CF$_3$ | H | H | S | H | Ph | |
| 4-Cl | H | H | S | H | Ph | |
| 4-Br | H | H | S | H | Ph | |
| 4-OCF$_2$H | H | H | S | H | Ph | |
| 4-CF$_3$ | H | H | S | CO$_2$Me | H | |
| 4-Cl | H | H | S | CO$_2$Me | H | |
| 4-Br | H | H | S | H | CO$_2$Me | |
| 4-OCF$_2$H | H | H | S | H | CO$_2$Me | |
| 4-CF$_3$ | 5-Cl | H | S | Me | H | 251 to 255 |
| 4-Cl | 5-Cl | H | S | Me | H | 222 to 226 |
| 4-Br | 5-Cl | H | S | Me | H | 228 to 230 |
| 4-OCF$_2$H | 5-Cl | H | S | Me | H | |
| 4-CF$_3$ | 5-Cl | H | S | H | Me | 171 to 173 |
| 4-Cl | 5-Cl | H | S | H | Me | 170 to 176 |
| 4-Br | 5-Cl | H | S | H | Me | 120 to 125 |
| 4-OCF$_2$H | 5-Cl | H | S | H | Me | |
| 4-CF$_3$ | 5-Cl | H | S | Me | Me | 200 to 202 |
| 4-Cl | 5-Cl | H | S | Me | Me | 190 to 193 |
| 4-Br | 5-Cl | H | S | Me | Me | 204 to 207 |
| 4-OCF$_2$H | 5-Cl | H | S | Me | Me | |
| 4-CF$_3$ | 5-Cl | H | S | Ph | H | |
| 4-Cl | 5-Cl | H | S | Ph | H | |
| 4-Br | 5-Cl | H | S | Ph | H | |
| 4-OCF$_2$H | 5-Cl | H | S | Ph | H | |
| 4-CF$_3$ | 5-Cl | H | S | H | PH | |
| 4-Cl | 5-Cl | H | S | H | Ph | |
| 4-Br | 5-Cl | H | S | H | Ph | |
| 4-OCF$_2$H | 5-Cl | H | S | H | Ph | |
| 4-CF$_3$ | 5-Cl | H | S | CO$_2$Me | H | |
| 4-Cl | 5-Cl | H | S | CO$_2$Me | H | |
| 4-Br | 5-Cl | H | S | H | CO$_2$Me | |
| 4-OCF$_2$H | 5-Cl | H | S | H | CO$_2$Me | |
| 4-CF$_3$ | 5-Br | H | S | Me | H | |
| 4-Cl | 5-Br | H | S | Me | H | |
| 4-Br | 5-Br | H | S | Me | H | |
| 4-CF$_3$ | 5-F | H | S | Me | H | |
| 4-Cl | 5-F | H | S | Me | H | |
| 4-Br | 5-F | H | S. | Me | H | |
| 4-CF$_3$ | 4-F | H | S | Me | H | |
| 4-Cl | 4-F | H | S | Me | H | |
| 4-Br | 4-F | H | S | Me | H | |
| 4-CF$_3$ | 5-Br | H | S | H | Me | |
| 4-Cl | 5-Br | H | S | H | Me | |
| 4-Br | 5-Br | H | S | H | Me | |
| 4-CF$_3$ | 5-F | H | S | H | Me | |
| 4-Cl | 5-F | H | S | H | Me | |
| 4-Br | 5-F | H | S. | H | Me | |
| 4-CF$_3$ | 4-F | H | S | H | Me | |
| 4-Cl | 4-F | H | S | H | Me | |
| 4-Br | 4-F | H | S | H | Me | |
| 4-CF$_3$ | 5-Br | H | S | Me | Me | 190 to 196 |
| 4-Cl | 5-Br | H | S | Me | Me | 165 to 186 |
| 4-Br | 5-Br | H | S | Me | Me | 208 to 211 |
| 4-CF$_3$ | 5-F | H | S | Me | Me | |
| 4-Cl | 5-F | H | S | Me | Me | |
| 4-Br | 5-F | H | S | Me | Me | |
| 4-CF$_3$ | 4-F | H | S | Me | Me | |
| 4-Cl | 4-F | H | S | Me | Me | |
| 4-Br | 4-F | H | S | Me | Me | |
| 4-CF$_3$ | 4-Cl | H | S | Me | Me | 170 to 173 |
| 4-Cl | 4-Cl | H | S | Me | Me | 150 to 168 |
| 4-Br | 4-Cl | H | S | Me | Me | 158 to 170 |

TABLE 18

| $R_1$ | $R_2$ | B | V | $R_8^a$ | $R_8^b$ | Phys. Prop. (m.p. °C.) |
|---|---|---|---|---|---|---|
| 4-CF$_3$ | H | H | O | Me | H | |
| 4-CF$_3$ | H | CO$_2$Me | O | Me | H | |
| 4-CF$_3$ | 5-Cl | H | S | Me | H | |
| 4-CF$_3$ | 5-Cl | CO$_2$Me | S | H | Me | |
| 4-CF$_3$ | 5-Cl | H | O | H | Me | |
| 4-CF$_3$ | 5-Cl | CO$_2$Me | O | H | Me | |
| 4-CF$_3$ | 5-F | H | S | Me | Me | |
| 4-CF$_3$ | 5-F | CO$_2$Me | S | Me | Me | |
| 4-CF$_3$ | 5-OCF$_2$H | H | O | Me | Me | |
| 4-CF$_3$ | 5-OCF$_2$H | CO$_2$Me | O | H | Me | |
| 4-CF$_3$ | 4-Cl | H | S | H | Me | |
| 4-CF$_3$ | 4-Cl | CO$_2$Me | S | H | Me | |
| 4-Cl | H | H | O | Me | Me | |
| 4-Cl | H | CO$_2$Me | O | Me | Me | |
| 4-Cl | 5-Cl | H | S | Me | Me | |
| 4-Cl | 5-Cl | CO$_2$Me | S | H | Me | |
| 4-Cl | 5-Cl | H | O | H | Me | |
| 4-Cl | 5-Cl | CO$_2$Me | O | H | Me | |
| 4-Cl | 5-OCF$_2$H | H | S | Me | Me | |
| 4-Cl | 5-OCF$_2$H | CO$_2$Me | S | Me | Me | |
| 4-Cl | 5-OCF$_2$H | H | O | Me | Me | |
| 4-Cl | 5-OCF$_2$H | CO$_2$Me | O | H | Me | |
| 4-Cl | 4-F | H | S | H | Me | |
| 4-Cl | 4-F | CO$_2$Me | S | H | Me | |

Formulation and Use

The compounds of this invention will generally be used in formulation with an agriculturally suitable carrier comprising a liquid or solid diluent or an organic solvent. Useful formulations of the compounds of Formula I can be prepared in conventional ways. They include dusts, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain effective amounts of these ingredients in the following approximate proportions:

| | Active Ingredient | Percent by Weight Diluent (s) | Surfactant (s) |
|---|---|---|---|
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by rank mixing.

Typical solid diluents are described in Watkins, et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Examples of useful formulations of compounds of the present invention are as follows:

EXAMPLE A

Emulsifiable Concentrate

| | |
|---|---|
| 3,3a,4,5-tetrahydro-3a-methyl-N-[4-(triflluoromethyl)-phenyl]-2H-benz[g]indazole-2-carboxamide | 5% |
| blend of oil soluble sulfonates and polyoxyethylene ethers | 4% |
| xylene | 91% |

The ingredients are combined and stirred with gentle warming to speed solution. A fine screen filter is included in packaging operation to insure the absence of any extraneous undissolved material in the product.

EXAMPLE B

Wettable Powder

| | |
|---|---|
| Methyl 3,3a,4,5-tetrahydro-2-[[4-(trifluoromethyl)-phenylamino]carbonyl]-2H-benz[g]indazole-3a-carboxylate | 30% |
| sodium alkylnaphthalenesulfonate | 2% |
| sodium ligninsulfonate | 2% |
| synthetic amorphous silica | 3% |
| kaolinite | 63% |

The active ingredient, warmed to reduce viscosity, is sprayed onto the inert materials in a blender. After grinding in a hammer-mill, the material is reblended and sifted through a 50 mesh screen.

EXAMPLE C

Dust

| | |
|---|---|
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

Granule

| | |
|---|---|
| 3,3a,4,5-tetrahydro-3a-methyl-N-[4-(trifluoromethyl)-phenyl]-2H-benz[g]indazole-2-carboxamide | 10% |
| attapulgite granules (low volative matter, 0.71/0.30 mm; U.S.S. No. 25–50 sieves) | 90% |

The active ingredient is dissolved in a suitable solvent and sprayed onto dedusted attapulgite granules in a double cone blender. The granules are warmed to drive off solvent, cooled and packaged.

EXAMPLE E

Granule

| | |
|---|---|
| Wettable powder of Example D | 15% |
| gypsum | 69% |

-continued

| | |
|---|---|
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE F

Solution

| | |
|---|---|
| Methyl 3,3a,4,5-tetrahydro-2-[[4-(trifluoromethyl)-phenylamino]carbonyl]-2H-benz[g]indazole-3a-carboxylate | 10% |
| isophrone | 90% |

The ingredients are combined and stirred to produce a solution suitable for direct, low volume application.

Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of the present invention can be mixed or formulated are:

Insecticides:
3-hydroxy-N-methylcrotonamide(dimethylphosphate)ester (monocrotophos)
methylcarbamic acid, ester with 2,3-dihydro-2,2dimethyl-7-benzofuranol (carbofuran)
O-[2,4,5-trichloro-α-(chloromethyl)benzyl]phosphoric acid, O', O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidyl)phosphorothioate (diazinon)
octachlorocamphene (toxaphene)
O-ethyl O-p-nitrophenyl phenylphosphonothioate (EPN)
(S)-α-cyano-m-phenoxybenzyl(1R,3R)-3-(2,2-dibromovinyl)-2,2-dimethylcyclopropanecarboxylate (deltamethrin)
Methyl N',N'-dimethyl-N-[(methylcarbamoyl)oxy]-1-thiooxamimidate (oxamyl)
cyano(3-phenoxyphenyl)-methyl-4-chloro-α-(1-methylethyl)benzeneacetate (fenvalerate)
(3-phenoxyphenyl)methyl(+)-cis,trans-3-(2,2-dichloroethenyl)-2,2-dimethylcyclopropanecarboxylate (permethrin)
α-cyano-3-phenoxybenzyl 3-(2,2-dichlorovinyl)-2,2dimethylcyclopropane carboxylate (cypermethrin)
O-ethyl-S-(p-chlorophenyl)ethylphosphonodithioate (profenofos)
phosphorothiolothionic acid, O-ethyl-O-[4-(methylthio)phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotophos, phosmet, phosphamidon, phosalone, pirimicarb, phorate, profenofos, terbufos, trichlorfon, methoxychlor bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl)methyl]-1H1,2,4-triazole.

Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O''-[4-(methylthio)-m-tolyl]diester (fenamiphos).

Bactericides:
tribasic copper sulfate
streptomycin sulfate.

Acaricides:
senecioic acid, ester with 2-sec-butyl-4,6-dinitrophenol (binapacryl)
6-methyl-1,3-dithiolo[4,5-β]quinoxalin-2-one (oxythioquinox)
ethyl 4,4'-dichlorobenzilate (chlorobenzilate)
1,1-bis(p-chlorophenyl)-2,2,2-trichlcroethanol (dicoiol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
bisclofentezin.

Biological
*Bacillus t huringiensis*
Avermectin B.

Utility

The compounds of the present invention exhibit activity against a wide spectrum of foliar and soil inhabiting insects. Those skilled in the art will recognize that not all compounds are equally effective against all insects, but compounds of this invention display control of many of the economically important pest species of the insect orders Lepidoptera, Homoptera, and Coleoptera among many others. The specific species for which control is exemplified below are: fall armyworm, *Spodoptera frugiperda;* boll weevil, *Anthonomus grandis;*

European corn borer, *Ostrinia nubilalis;* southern corn rootworm, *Diabrotica undecimpunctata howardi;* aster leafhopper, *Macrosteles fascifrons;* Tobacco budworm, *Heliothis virescens.* The pest control afforded by the compounds of the present invention is not limited, however, to these species.

Application

Insects are controlled and agricultural crops are protected by applying one or more of the Formula I compounds of this invention, in an effective amount, to the locus of infestation, to the area to be protected, or directly on the pests to be controlled. A preferred method of application is by spraying with spray equipment that distributes the compound on the foliage, in the soil, or to the plant part that is infested or needs to be protected. Alternatively, granular formulations of these compounds can be applied to soil or foliage or, optionally, incorporated into the soil. Either aerial or ground application can be used.

The substituted indazole(s) of this invention can be applied in its(their) pure state, but most often application will be of a formulation comprising one or more compounds of this invention, in an agriculturally suitable carrier or diluent. A most preferred method of application involves spraying a water dispersion or refined oil solution of the compounds.

The rate of application of the Formula I compounds required for effective control will depend on such factors as the species of insect to be controlled, the pest's life stage, its size, its location, the host crop, time of year of application, ambient moisture, temperature conditions, and the like. In general, application rates of 0.05 to 2 kg of active ingredient per hectare are sufficient to provide effective control in large scale field operations under normal circumstances, but as little as 0.01 kg/hectare may be sufficient or as much as 8 kg/hectare may be required, depending upon the factors listed above.

The following Examples demonstrate the control efficacy of compounds of Formula I on specific insect pests wherein Compounds 1 through 8 are those of Examples I to B and Compounds 9 through 181 are as depicted in Tables 19 and 20. Compounds not listed were either not tested or did not effect at least 80% mortality in that screen.

TABLE 19

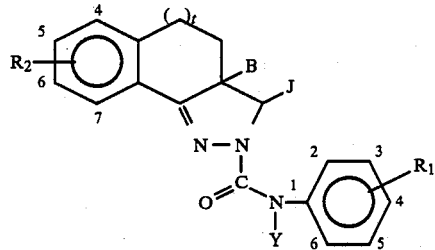

| CMPD | $R_1$ | $R_2$ | J | Y | t | B |
|---|---|---|---|---|---|---|
| 9 | 4-Cl | H | H | H | 1 | H |
| 10 | 4-Br | H | H | H | 1 | H |
| 11 | 4-OCF$_3$ | H | H | H | 1 | H |
| 12 | 4-Cl | 5-Cl | H | H | 1 | H |
| 13 | 4-Br | 5-Cl | H | H | 1 | H |
| 14 | 4-CF$_3$ | 5-OMe | H | H | 1 | H |
| 15 | 4-CF$_3$ | 5-OCF$_2$H | H | H | 1 | H |
| 16 | 4-CF$_3$ | 5-F | H | H | 1 | H |
| 17 | 4-CF$_3$ | 4-Cl | H | H | 1 | H |
| 18 | 4-CF$_3$ | 4-F | H | H | 1 | H |
| 19 | 4-CF$_3$ | 5,6-di-Cl | H | H | 1 | H |
| 20 | 4-CF$_3$ | 5-F | H | H | 1 | CO$_2$Me |
| 21 | 4-CF$_3$ | 5-OMe | H | H | 1 | CO$_2$Me |
| 22 | 4-CF$_3$ | 4-Cl | H | H | 1 | CO$_2$Me |
| 23 | 4-CF$_3$ | 4-F | H | H | 1 | CO$_2$Me |
| 24 | 4-CF$_3$ | 5,6-di-Cl | H | H | 1 | CO$_2$Me |
| 25 | 4-CF$_3$ | H | H | H | 1 | Et |
| 26 | 4-CF$_3$ | H | H | H | 1 | CH$_2$—Ph-4-F |
| 27 | 4-CF$_3$ | H | H | H | 1 | (CH$_2$)$_2$CN |
| 28 | 4-CF$_3$ | H | H | H | 1 | (CH$_2$)$_3$CN |
| 29 | 4-CF$_3$ | H | H | H | 1 | CO$_2$Et |
| 30 | 4-CF$_3$ | H | H | H | 1 | CO$_2$(CH$_2$)$_2$Cl |
| 31 | 4-CF$_3$ | H | H | H | 1 | CO$_2$(CH$_2$)$_2$Br |
| 32 | 4-CF$_3$ | H | H | H | 1 | CO$_2$CH$_2$CF$_3$ |
| 33 | 4-CF$_3$ | H | H | H | 1 | CO$_2$CH$_2$CCl$_3$ |
| 34 | 4-CF$_3$ | H | H | H | 1 | CONH$_2$ |
| 35 | 4-CF$_3$ | H | H | H | 1 | CONHMe |
| 36 | 4-CF$_3$ | H | H | H | 1 | CONMe$_2$ |
| 37 | 4-CF$_3$ | H | H | H | 1 | COH(H)CH$_2$CH=CH$_2$ |
| 38 | 4-CF$_3$ | H | H | H | 1 | CON(Me)CH$_2$CH=CH$_2$ |
| 39 | 4-CF$_3$ | H | H | H | 1 | CONH(4-Cl—Ph) |
| 40 | 4-Cl | 5-Cl | H | H | 1 | CO$_2$Me |
| 41 | 4-Br | 5-Cl | H | H | 1 | CO$_2$Me |
| 42 | 4-CF$_3$ | H | H | H | 1 | CO-piperidinyl |
| 43 | 4-CF$_3$ | H | H | H | 1 | CO$_2$H |
| 44 | 4-CF$_3$ | H | H | H | 1 | CO$_2$Na |
| 45 | 4-CF$_3$ | H | H | C(O)Me | 1 | CO$_2$Me |
| 46 | 4-CF$_3$ | H | H | Me | 1 | CO$_2$Me |
| 47 | 4-CF$_3$ | H | H | CO$_2$Me | 1 | CO$_2$Me |
| 48 | 4-CF$_3$ | H | H | C(O)Me | 1 | H |

TABLE 19-continued

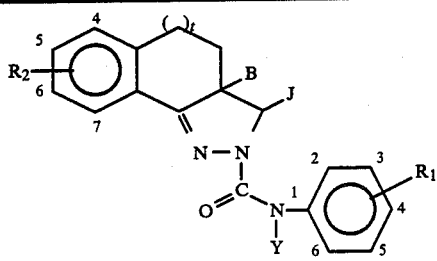

| CMPD | R₁ | R₂ | J | Y | t | B |
|---|---|---|---|---|---|---|
| 49 | 4-CF₃ | H | 4-F—Ph | H | 1 | H |
| 50 | 4-Cl | H | 4-F—Ph | H | 1 | H |
| 51 | 4-CF₃ | H | 4-Cl—Ph | H | 1 | H |
| 52 | 4-Cl | H | 4-Cl—Ph | H | 1 | H |
| 53 | 4-CF₃ | H | H | H | 1 | CH₂CH=CH₂ |
| 54 | 4-CF₃ | H | H | H | 1 | CH₂Ph |
| 55 | 4-CF₃ | H | H | H | 1 | CO₂Et |
| 56 | 4-Cl | H | H | H | 1 | CO₂Et |
| 57 | 4-Br | H | H | H | 1 | CO₂Me |
| 58 | 4-Br | H | H | H | 1 | CO₂Et |
| 59 | 4-Cl | H | H | H | 1 | CO₂Me |
| 60 | 4-Cl | 5-OMe | H | H | 1 | H |
| 61 | 4-CF₃ | H | H | H | 1 | CO₂Ph |
| 62 | 4-CF₃ | H | H | CO₂-t-Bu | 1 | H |
| 63 | 4-SMe | 5-Cl | H | H | 1 | H |
| 64 | 4-CO₂Et | 5-Cl | H | H | 1 | H |
| 65 | 4-SMe | 5-Cl | H | H | 1 | CO₂Me |
| 66 | 4-CO₂Et | 5-Cl | H | H | 1 | CO₂Me |
| 67 | 4-CF₃ | H | H | H | 2 | H |
| 68 | 4-CF₃ | H | H | H | 2 | Me |
| 69 | 4-Cl | H | H | H | 2 | H |
| 70 | 4-Cl | H | H | H | 2 | Me |

TABLE 20

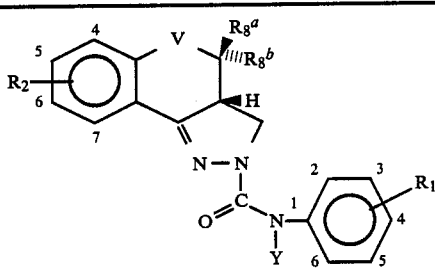

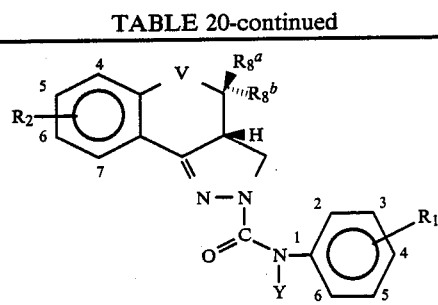

| CMPD | R₁ | R₂ | Y | V | R₈ᵃ | R₈ᵇ |
|---|---|---|---|---|---|---|
| 71 | 4-CF₃ | H | H | O | H | H |
| 72 | 4-CF₃ | H | H | S | H | H |
| 73 | 3,4-di-Cl | H | H | O | H | H |
| 74 | 4-Br | H | H | O | H | H |
| 75 | 3-CF₃ | H | H | O | H | H |
| 76 | 4-Cl | H | H | O | H | H |
| 77 | 3-Cl | H | H | O | H | H |
| 78 | 3,4-di-Cl | H | H | S | H | H |
| 79 | 4-Br | H | H | S | H | H |
| 80 | 3-CF₃ | H | H | S | H | H |
| 81 | 4-Cl | H | H | S | H | H |
| 82 | 3-Cl | H | H | S | H | H |
| 83 | 3-CF₃ | H | H | SO(α) | H | H |
| 84 | 4-CF₃ | H | H | SO₂ | H | H |
| 85 | 4-CF₃ | H | H | SO(α) | H | H |
| 86 | 3,4-di-Cl | H | H | SO₂ | H | H |
| 87 | 4-Br | H | H | SO(α) | H | H |
| 88 | 4-Br | H | H | SO(β) | H | H |
| 89 | 3,4-di-Cl | H | H | SO(α) | H | H |
| 90 | 3,4-di-Cl | H | H | SO(β) | H | H |
| 91 | 4-Cl | H | H | SO(α) | H | H |
| 92 | 4-Cl | H | H | SO(β) | H | H |
| 93 | 3-Cl | H | H | SO(α) | H | H |
| 94 | 3-Cl | H | H | SO(β) | H | H |
| 95 | 4-Br | H | H | SO₂ | H | H |
| 96 | 3-CF₃ | H | H | SO₂ | H | H |
| 97 | 4-Cl | H | H | SO₂ | H | H |
| 98 | 3-Cl | H | H | SO₂ | H | H |
| 99 | 3-CF₃ | H | H | SO(β) | H | H |
| 100 | 4-CF₃ | 5-Cl | H | S | H | H |
| 101 | 3-CF₃ | 5-Cl | H | S | H | H |
| 102 | 4-Cl | 5-Cl | H | S | H | H |
| 103 | 3-Cl | 5-Cl | H | S | H | H |
| 104 | 4-Br | 5-Cl | H | S | H | H |
| 105 | 3,4-di-Cl | 5-Cl | H | S | H | H |
| 106 | 4-CF₃ | 6-Cl | H | S | H | H |
| 107 | 3-CF₃ | 6-Cl | H | S | H | H |
| 108 | 4-Cl | 6-Cl | H | S | H | H |
| 109 | 3-Cl | 6-Cl | H | S | H | H |
| 110 | 4-Br | 6-Cl | H | S | H | H |
| 111 | 3,4-di-Cl | 6-Cl | H | S | H | H |
| 112 | 4-CF₃ | 5-Cl | H | SO₂ | H | H |
| 113 | 3-CF₃ | 5-Cl | H | SO₂ | H | H |
| 114 | 4-Cl | 5-Cl | H | SO₂ | H | H |
| 115 | 3-Cl | 5-Cl | H | SO₂ | H | H |
| 116 | 4-Br | 5-Cl | H | SO₂ | H | H |
| 117 | 3,4-di-Cl | 5-Cl | H | SO₂ | H | H |
| 118 | 4-CF₃ | 6-Cl | H | SO₂ | H | H |
| 119 | 3-CF₃ | 6-Cl | H | SO₂ | H | H |
| 120 | 4-Cl | 6-Cl | H | SO₂ | H | H |
| 121 | 3-Cl | 6-Cl | H | SO₂ | H | H |
| 122 | 4-Br | 6-Cl | H | SO₂ | H | H |
| 123 | 3,4-di-Cl | 6-Cl | H | SO₂ | H | H |
| 124 | 4-CF₃ | 5-Cl | H | SO(α) | H | H |

TABLE 20-continued

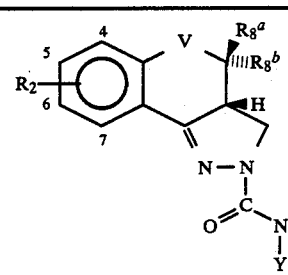

| CMPD | R1 | R2 | Y | V | R8a | R8b |
|---|---|---|---|---|---|---|
| 125 | 4-CF3 | 5-Cl | H | SO(β) | H | H |
| 126 | 3-CF3 | 5-Cl | H | SO(α) | H | H |
| 127 | 3-CF3 | 5-Cl | H | SO(β) | H | H |
| 128 | 4-Cl | 5-Cl | H | SO(α) | H | H |
| 129 | 4-Cl | 5-Cl | H | SO(β) | H | H |
| 130 | 3-Cl | 5-Cl | H | SO(α) | H | H |
| 131 | 3-Cl | 5-Cl | H | SO(β) | H | H |
| 132 | 4-Br | 5-Cl | H | SO(α) | H | H |
| 133 | 4-Br | 5-Cl | H | SO(β) | H | H |
| 134 | 3,4-di-Cl | 5-Cl | H | SO(α) | H | H |
| 135 | 3,4-di-Cl | 5-Cl | H | SO(β) | H | H |
| 136 | 4-CF3 | 6-Cl | H | SO(α) | H | H |
| 137 | 4-CF3 | 6-Cl | H | SO(β) | H | H |
| 138 | 3-CF3 | 6-Cl | H | SO(α) | H | H |
| 139 | 3-CF3 | 6-Cl | H | SO(β) | H | H |
| 140 | 4-Cl | 6-Cl | H | SO(α) | H | H |
| 141 | 4-Cl | 6-Cl | H | SO(β) | H | H |
| 142 | 3-Cl | 6-Cl | H | SO(α) | H | H |
| 143 | 3-Cl | 6-Cl | H | SO(β) | H | H |
| 144 | 4-Br | 6-Cl | H | SO(α) | H | H |
| 145 | 4-Br | 6-Cl | H | SO(β) | H | H |
| 146 | 3,4-di-Cl | 6-Cl | H | SO(α) | H | H |
| 147 | 3,4-di-Cl | 6-Cl | H | SO(β) | H | H |
| 148 | 4-CF3 | 5-Br | H | S | H | H |
| 149 | 3-CF3 | 5-Br | H | S | H | H |
| 150 | 4-Cl | 5-Br | H | S | H | H |
| 151 | 3-Cl | 5-Br | H | S | H | H |
| 152 | 4-Br | 5-Br | H | S | H | H |
| 153 | 3,4-di-Cl | 5-Br | H | S | H | H |
| 154 | 4-CF3 | H | H | SO(β) | H | H |
| 155 | 4-CF3 | H | H | S | H | H |
| 156 | 4-CF3 | H | H | S | H | H |
| 157 | 4-CF3 | H | H | S | H | H |
| 158 | 4-CF3 | 5-Cl | C(O)Me | S | H | H |
| 159 | 4-CF3 | 5-Cl | CO2Me | S | H | H |
| 160 | 4-CF3 | 5-Cl | Me | S | H | H |
| 161 | 4-Cl | H | C(O)Me | S | H | H |
| 162 | 4-Cl | H | Me | S | H | H |
| 163 | 4-Cl | 5-Cl | C(O)Me | S | H | H |
| 164 | 4-Cl | 5-Cl | Me | S | H | H |
| 165 | 4-CF3 | H | H | S | Me | Me |
| 166 | 4-Cl | H | H | S | Me | Me |
| 167 | 4-Br | H | H | S | Me | Me |
| 168 | 4-Cl | 5-Cl | H | S | Me | Me |
| 169 | 4-Br | 5-Cl | H | S | Me | Me |
| 170 | 4-CF3 | H | H | S | Me | H |
| 171 | 4-CF3 | H | H | S | H | Me |
| 172 | 4-Cl | H | H | S | Me | H |
| 173 | 4-Cl | H | H | S | H | Me |
| 174 | 4-Br | H | H | S | Me | H |
| 175 | 4-Br | H | H | S | H | Me |
| 176 | 4-CF3 | 5-Cl | H | S | Me | H |
| 177 | 4-CF3 | 5-Cl | H | S | H | Me |
| 178 | 4-Cl | 5-Cl | H | S | Me | H |
| 179 | 4-Cl | 5-Cl | H | S | H | Me |
| 180 | 4-Br | 5-Cl | H | S | Me | H |
| 181 | 4-Br | 5-Cl | H | S | H | Me |

EXAMPLE 9

Fall Armyworm

Test units, each consisting of an 8-ounce plastic cup containing a layer of wheat germ diet, approximately 0.5 cm thick, were prepared. Ten third-instar larvae of fall armyworm (*Spodoptera fruqiperda*) were placed into each cup. Solutions of each of the belowlisted test compounds (acetone/distilled water 75/25 solvent) were sprayed onto the cups, a single solution per cup. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time mortality readings were taken. Of the compounds tested on fall armyworm, the following resulted in greater than or equal to 80% mortality: 3, 4, 5, 7, 15, 17, 20, 22, 23, 25, 45, 59, 72, 100, 125, 148, 158, 159. 160, 165, 166, 168, 169, 170, 173, 177, 179, 181.

EXAMPLE 10

European Corn Borer

Test units, each consisting of an 8-ounce plastic cup containing a one-inch square of wheat germ/soyflour diet were prepared. Five third-instar larvae of the European corn borer (*Ostrinia nubilalis*) were placed into each cup. The test units were sprayed as described in Example 9 with individual solutions of the below-listed compounds. The cups were then covered and held at 27° C. and 50% relative humidity for 48 hours, after which time mortality readings were taken. Of the compounds tested on European corn borer, the following resulted in greater than or equal to 80% mortality: 2, 3, 4, 5, 15, 22, 23, 29, 45, 47, 53, 54, 55, 56, 58, 59, 71, 72, 81 84, 91, 95, 97, 100, 165, 177.

EXAMPLE 11

Southern Corn Rootworm

Test units, each consisting of an 8-ounce plastic cup containing 1 sprouted corn seed, were prepared. Sets of three test units were sprayed as described in Example 9 with individual solutions of the test compounds. After the spray on the cups had dried, five third-instar larvae of the southern corn rootworm (*Diabrotica undecimounctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested on Southern rootworm, the following resulted in greater than or equal to 80% mortality: 1, 2, 3, 4, 5, 7, 15, 16, 17, 20, 21, 22, 23, 25, 27, 29, 35, 36, 45, 47; 53, 54; 56, 58, 59, 72, 76, 79, 81, 84, 91, 95, 97, 100, 124, 125, 132, 133, 148, 154, 157, 158, 160, 162, 165, 166, 168, 169, 170, 172, 173, 174, 175, 180.

EXAMPLE 12

Boll Weevil

Five adult boll weevils (*Anthonomus orandis*) were placed into each of a series of 9-ounce cups. The test procedure employed was then otherwise the same as in Example 9. Mortality readings were taken 48 hours after treatment. Of the compounds tested on boll weevil, the following resulted in greater than or equal to 80% mortality: 1, 2, 3, 4, 5, 7, 14, 15, 22, 23, 35, 45, 47, 53, 58, 59, 61, 67, 71, 72, 76, 81, 84, 91, 97, 104, 165. 177.

EXAMPLE 13

Aster Leafhopper

Test units were prepared from a series of 12-ounce cups, each containing oat (*Avena sativa*) seedlings in a 1-inch layer of sterilized soil. The test units were sprayed as described in Example 9 with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested on aster leafhopper, the following resulted in greater than or equal to 80% mortality: 2, 3, 4, 5, 7, 15, 16, 20, 22, 23, 25, 45, 47, 53, 59, 72, 79, 100, 104, 157, 158, 159, 160, 162, 165, 166, 168, 169, 171, 172, 173, 174, 175, 177, 179, 181.

EXAMPLE 14

Tobacco Budworm

The test procedure of Example 9 was repeated on third-instar larvae of the tobacco budworm (*Heliothis virescens*) except that mortality was assessed at 48 hours. Of the compounds tested on tobacco budworm, the following resulted in greater than or equal to 80% mortality: 5, 7, 15, 23, 25, 39, 100, 160, 165, 168, 177.

EXAMPLE 15

Soil Control of Southern Corn Rootworm

Test units, each consisting of a three inch cylindrical pot containing 200 grams of moist sassafras loam soil and 2 kernels of Dekalb T1100 corn were prepared. Spraying was accomplished by passing the pots, on a conveyer belt, directly beneath a flat fan hydraulic nozzle which discharged the spray at a rate of 0.25 pounds of active ingredient per acre (about 2 ppm soil concentration) at 30 p.s.i. After the test units had been sprayed, the corn seed was covered with soil and ten third-instar southern corn rootworm larvae (*Diabrotica undecimpunctata howardi*) were added to each unit. Test units were held at 24 degree C., 70% relative humidity and under a photo cycle of 16 hours of light/8 hours of darkness for 7 days, after which time control readings were taken. Control was measured by root injury ratings of 1 to 5, where 1 was no injury and 5 was complete destruction of the root system. Percent of corn seedlings that emerged also was utilized to measure control. The results are tabulated below.

| Compound | Root Rating | % Emergence |
|---|---|---|
| 2 | 1.5 | 100 |
| 3 | 1.0 | 88 |
| 5 | 1.0 | 100 |
| 15 | 1.3 | 88 |
| 20 | 1.6 | 75 |
| 22 | 2.0 | 75 |
| 23 | 1.0 | 75 |
| 29 | 1.0 | 100 |
| 59 | 1.1 | 100 |

What is claimed is:

1. A compound of the formula

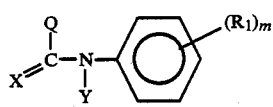

wherein

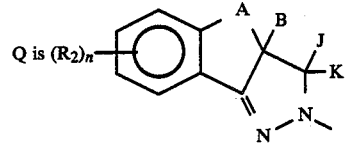

A is a 1, 2 or 3-atom bridge having 0 to 3 carbon atoms and 0 to 1 oxygen atom $NR_6$ group, or $S(O)_q$ group, wherein each carbon individual be substituted with 1 to 2 substituents selected from 1 to 2 halogen, $C_1$ to $C_6$ alkyl, $C_2$ to $C_4$ alkoxycarbonyl or phenyl optionally substituted with 1 to 3 substituents selected from W and one of the carbon atoms can be C(O) or C(S);

B is H $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $OR_7$, $C_2$ to $C_6$ alkoxyalkyl, $C_2$ to $C_6$ cyanoalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl, phenyl substituted by $(R_5)_p$, benzyl, or benzyl substituted with 1 to 3 substituents independently selected from W;

J is H, $C_1$ to $C_4$ alkyl or phenyl optionally substituted with W;

K is H or $CH_3$;

W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;

$R_1$, $R_2$ and $R_5$ are independently $R_3$, halogen, CN, $N_3$, SCN, $NO_2$, $OR_3$, $SR_3$, $SOR_3$, $SO_2R_3$, $OC(O)R_3$, $OSO_2R_3$, $CO_2R_3$, $C(O)R_3$, $C(O)NR_3R_4$, $SO_2NR_3R_4$, $NR_3R_4$, $NR_4C(O)R_3$, $OC(O)NHR_3$, $NR_4C(O)NHR_3$, $NR_4SO_2R_3$, or when m, n or p is 2, $R_1$, $R_2$ or $R_5$ can be taken together to form a 5 or 6 membered fused ring as $-OCH_2O-$, $-OCH_2CH_2O-$, or $-CH_2CH_2O-$, each of which can be substituted with 1 to 4 halogen atoms or 1 to 2 methyl groups;

$R_3$ is H, $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $C_2$ to $C_6$ haloalkynyl, $C_2$ to $C_6$ alkoxyalkyl, $C_2$ to $C_6$ alkylthioalkyl, $C_1$ to $C_6$ nitroalkyl, $C_2$ to $C_6$ cyanoalkyl, $C_3$ to $C_8$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H, $C_1$ to $C_4$ alkyl or $R_3$ and $R_4$ can be taken together as $(CH_2)_4$, $(CH_2)_5$ or $(CH_2CH_2OCH_2CH_2)$;

$R_6$ is H, $C_1$ to $C_4$ alkyl, $C_1$ to $C_4$ haloalkyl, $C_2$ to $C_4$ alkenyl, $C_2$ to $C_4$ haloalkenyl, phenyl, benzyl, phenyl optionally substituted with W or benzyl optionally substituted with W;

$R_7$ is H, $C_1$ to $C_4$ alkyl, $C_2$ to $C_4$ alkenyl, $C_2$ to $C_4$ alkynyl, $C_2$ to $C_4$ alkylcarbonyl, $C_2$ to $C_4$ alkoxycarbonyl, $C_1$ to $C_4$ alkylsulfonyl;

X is O or S;

n is 1 to 4;

m is 1 to 5;

p is 1 to 3;

q is 0 to 2; and

Y i H, $C_1$ to $C_6$ alkyl, benzyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, or phenylthio substituted with 1 to 3 substituents independently selected from W.

2. A compound according to claim 1 wherein Q is

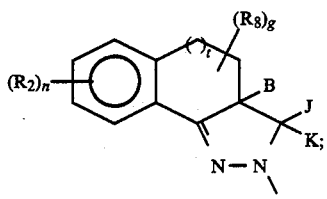
Q-1

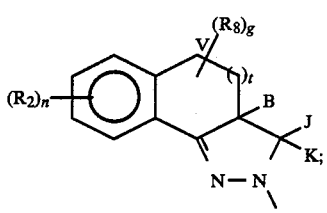
Q-2

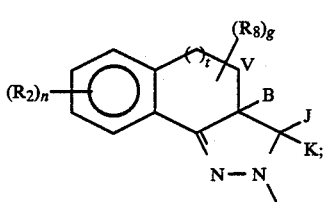
Q-3

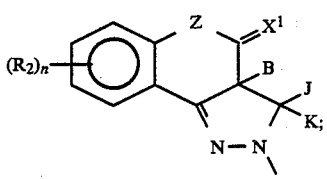
Q-4 or

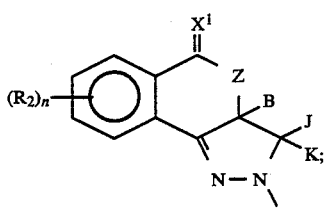
Q-5

X is O or S;
$X^1$ is O or S;
t is 0, 1 or 2;
V is O, $S(O)_q$, or $NR_6$;
Z is O or $NR_6$;
$R_8$ is H, halogen, $C_1-C_6$ alkyl, $C_2-C_4$ alkoxycarbonyl, phenyl or phenyl substituted by 1—3 substituents selected from W; and
g is 0, 1 or 2.

3. A compound according to claim 2 wherein B is H, $C_1$ to $C_6$ alkyl, $C_1$ to $C_6$ haloalkyl, $C_2$ to $C_6$ alkenyl, $C_2$ to $C_6$ alkynyl, $C_2$ to $C_6$ alkoxyalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl or phenyl substituted by $(R_5)_p$;
J is H or $CH_3$;
$R_3$ is H, $C_1$ to $C_4$ alkyl, $C_1$ to $C_2$ haloalkyl, $C_3$ to $C_4$ alkenyl, $C_3$ to $C_4$ haloalkenyl, propargyl, phenyl, benzyl, or phenyl or benzyl substituted with one of F, Cl, Br, $CF_3$ or $NO_2$;
$R_6$ is H, $C_1$ to $C_4$ alkyl, allyl or propargyl;
n is 1 or 2;
p is 1 or 2;
m is 1 to 3; and
Y is H, $C_1$ to $C_4$ alkyl, $SCH_3$, $SCCL_3$, $SO_2CH_3$, $SC_6H_5$, $2-NO_2-C_6H_4S$, $C(O)CH_3$, $C(O)CF_3$, $CO_2CH_3$ or $CO_2CH_2CH_3$.

4. A compound according to claim 3 wherein B is H, $C_1$ to $C_4$ alkyl, $C_3-C_4$ alkoxycarbonylalkyl, $CO_2R_3$, $C(O)R_3$, phenyl or phenyl substituted by $(R_5)_p$;
J is H;
K is H;
$R_1$ is H, halogen, CN, SCN, $NO_2$, $OR_3$, $SR_3$, $SO_2R_3$, $CO_2R_3$, $C(O)R_3$ or $R_3$ with one $R_1$ substituent in the 4-position, or when m is 2 then $R_1$ can be taken together as $-CH_2C(CH_3)_2O-$, $OCH_2CH_2O-$, $OCF_2CF_2O-$ or $-CF_2CF_2O-$ to form a 5 or 6 membered fused ring;
$R_2$ and $R_5$ are H, $R_3$, halogen, CN, SCN, $NO_2$, $OR_3$, $SR_3$, $SO_2R_3$, $OC(O)R_3$, $OSO_2R_3$, $CO_2R_3$, $C(O)R_3$, $C(O)NR_3R_4$, $SO_2NR_3R_4$ or $NR_3R_4$;
$R_3$ is $C_1-C_4$ alkyl, $C_1-C_2$ haloalkyl, $C_3-C_4$ alkenyl or propargyl;
$R_4$ and $R_8$ are H or $CH_3$;
X is O;
X' is 0;
m is 1 or 2;
t is 1; and
q is 0.

5. A compound according to claim 4 wherein $R_1$ is Cl, F, Br, $CF_3$, CN, $OCF_3$, $OCF_2H$ or $SCF_2H$; $R_2$ is H, Cl, F, Br, CN, $CF_3$, $CH_3$, $OCF_2H$, $OCF_3$, $SCH_3$, $SCF_2H$, $SO_2CH_3$ or $NO_2$;
$R_6$ is H or $CH_3$;
B is H, $CH_3$, $CH_2CH_3$, $CO_2CH_3$, $CO_2CH_2CH_3$, phenyl or phenyl substituted by halogen, CN, $CF_3$ or $NO_2$, and;
Y is H.

6. A compound according to claim 5 wherein Q is Q-1.

7. A compound according to claim 5 wherein Q is Q-'.

8. A compound according to claim 6: methyl 3,3a,4,5-tetrahydro-2-[[4(trifluoromethyl)phenylamino]carbonyl]2H-benz[g]indazole-3a-carboxylate.

9. A compound according to claim 6: methyl 7-chloro-3,3a,4,5-tetrahydro-2-[[4trifluoromethyl)-phenylamino]carbonyl]2H-benz[g]indazole-3a-carboxylate.

10. A compound according to claim 6: 7-chloro-3,3a,4,-tetrahydro-N-[4-(trifluoromethyl)phenyl]-2H-benz[g]indazole-2carboxamide.

11. A compound according to claim 6: methyl 6-fluoro-3,3a,4,5-tetrahydro-2-[[4(trifluoromethyl)-phenylamino]carbonyl]-2Hbenz[g]indazole-3a-carboxylate.

12. A composition comprising an insecticidally effective amount of a compound according to any one of claims 1 to 11 and an agriculturally suitable carrier therefor.

13. A method for controlling insects comprising contacting them with an insecticidally effective amount of a compound according to any one of claims 1 to 11.

* * * * *

UNITED STATES PATENT AND TRADEMARK OFFICE
CERTIFICATE OF CORRECTION

PATENT NO. : 4,960,784

DATED : October 2, 1990

INVENTOR(S) : George Philip Lahm

It is certified that error appears in the above-identified patent and that said Letters Patent is hereby corrected as shown below:

In Claim 1, Column 60, line 10, after "0 to 1 oxygen atom", insert a comma.

In Claim 1, Column 60, line 11, "individual be" should read --individually can be--.

In Claim 1, Column 60, line 16, after "B is H", insert a comma.

In Claim 1, Column 60, line 65, correct to read --Y is H--.

In Claim 2, Column 61, correct the structures at lines 14 to 30 to read:

--

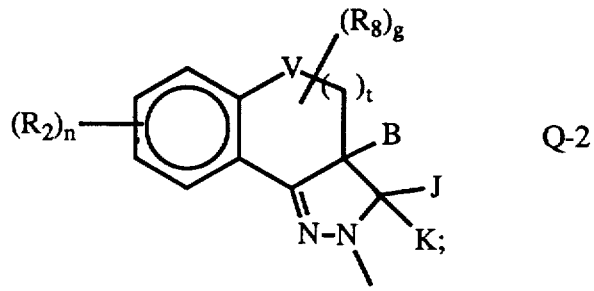

Q-2

UNITED STATES PATENT AND TRADEMARK OFFICE
CERTIFICATE OF CORRECTION

PATENT NO. : 4,960,784

DATED : October 2, 1990

INVENTOR(S) : George Philip Lahm

It is certified that error appears in the above-identified patent and that said Letters Patent is hereby corrected as shown below:

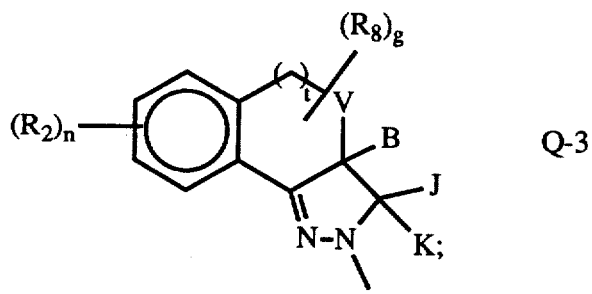

Q-3

--.

In Claim 2, Column 62, line 7, correct "SCCL3" to read --SCCl3--.

In Claim 4, Column 62, line 29, correct "X' is 0" to read --$X^1$ is O--.

In Claim 7, Column 62, lines 44 and 45, correct to read --Q is Q-2--.

In Claim 8, Column 62, lines 46 to 48, correct compound name to read --methyl 3,3a,4,5-tetrahydro-2-[[4-(trifluoromethyl)phenylamino]carbonyl]-2H-benz[g]indazole-3a-carboxylate--.

UNITED STATES PATENT AND TRADEMARK OFFICE
CERTIFICATE OF CORRECTION

PATENT NO. : 4,960,784

DATED : October 2, 1990

INVENTOR(S) : George Philip Lahm

It is certified that error appears in the above-identified patent and that said Letters Patent is hereby corrected as shown below:

In Claim 9, Column 62, lines 49 to 52, correct compound name to read --methyl 7-chloro-3,3a,4,5-tetrahydro-2-[[4-(trifluoromethyl)phenylamino]carbonyl]-2H-benz[g]indazole-3a-carboxylate--.

In Claim 10, Column 62, lines 53 to 55, correct compound name to read --7-chloro-3,3a,4-tetrahydro-N-[4-(trifluoromethyl)phenyl]-2H-benz[g]indazole-2-carboxamide--.

In Claim 11, Column 62, lines 56 to 59, correct compound name to read "-- 7-chloro-3,3a,4,5-tetrahydro-N-[4-(trifluoromethyl)phenyl]-2H-benz[g]indazole-2 carboxamide --."

Signed and Sealed this

Ninth Day of February, 1993

Attest:

STEPHEN G. KUNIN

Attesting Officer

Acting Commissioner of Patents and Trademarks